(12) United States Patent
Richardson

(10) Patent No.: US 10,124,275 B2
(45) Date of Patent: Nov. 13, 2018

(54) MICROSTRUCTURE SEPARATION FILTERS

(71) Applicant: Imagine TF, LLC, Los Gatos, CA (US)

(72) Inventor: Brian Edward Richardson, Los Gatos, CA (US)

(73) Assignee: Imagine TF, LLC, Menlo Park, CA (US)

( * ) Notice: Subject to any disclaimer, the term of this patent is extended or adjusted under 35 U.S.C. 154(b) by 300 days.

(21) Appl. No.: 14/846,154

(22) Filed: Sep. 4, 2015

(65) Prior Publication Data

US 2016/0067634 A1    Mar. 10, 2016

Related U.S. Application Data

(60) Provisional application No. 62/070,778, filed on Sep. 5, 2014, provisional application No. 62/123,717, filed
(Continued)

(51) Int. Cl.
*B01D 15/22* (2006.01)
*B01D 67/00* (2006.01)
(Continued)

(52) U.S. Cl.
CPC .......... *B01D 15/22* (2013.01); *B01D 67/006* (2013.01); *B01D 67/0062* (2013.01);
(Continued)

(58) Field of Classification Search
CPC ...... B01D 15/22; B01D 15/34; B01D 15/125; B01D 67/006; B01D 67/0062;
(Continued)

(56) References Cited

U.S. PATENT DOCUMENTS 1,977,174 A   10/1934  Crawford
3,250,396 A   5/1966   Armstrong et al.
(Continued)

FOREIGN PATENT DOCUMENTS

CN   203139755 U   8/2013
CN   106029202 A   10/2016
(Continued)

OTHER PUBLICATIONS

Chen, X., et al, "Microfluidic chip for blood cell separation and collection based on crossflow filtration", Sensors and Actuators B, 130, pp. 216-221 (2008).*
(Continued)

*Primary Examiner* — Katherine Zalasky
*Assistant Examiner* — Benjamin L Lebron
(74) *Attorney, Agent, or Firm* — Keith Kline; The Kline Law Firm PC

(57) ABSTRACT

Microstructure separation filters are provided herein, as well as chromatography and other separation devices. An exemplary filter device includes a microstructure filter has a plurality of layers of alternating sacrificial and/or structural material which have been etched to create inlet channels and outlet channels. Adjacent ones of the inlet channels and the outlet channels are spaced apart from one another by cross channels that filter a fluid from the inlet channels to the outlet channels. The cross channels include filter features formed by etching away of a portion of the layers. The device also includes a housing configured to receive the microstructure filter.

12 Claims, 65 Drawing Sheets

Related U.S. Application Data on Nov. 25, 2014, provisional application No. 62/176,125, filed on Feb. 9, 2015, provisional application No. 62/179,582, filed on May 11, 2015.

(51) Int. Cl.

| | |
|---|---|
| *B01L 9/00* | (2006.01) |
| *B01L 3/00* | (2006.01) |
| *B01D 69/02* | (2006.01) |
| *B01D 15/12* | (2006.01) |
| *G01N 30/60* | (2006.01) |
| *B01D 71/02* | (2006.01) |

(52) U.S. Cl.
CPC .......... *B01D 69/02* (2013.01); *B01L 3/5027* (2013.01); *B01L 3/502707* (2013.01); *B01L 3/502753* (2013.01); *B01L 9/527* (2013.01); *B01D 15/125* (2013.01); *B01D 71/02* (2013.01); *B01D 71/022* (2013.01); *B01D 2325/028* (2013.01); *G01N 30/603* (2013.01)

(58) Field of Classification Search
CPC ...... B01D 69/02; B01D 71/02; B01D 71/022; B01D 2325/028; B01F 15/0264; B01F 15/0601; B01J 19/0046; B01J 19/0093; B01J 2219/0059; B01J 2219/00722; B01L 7/52; B01L 7/525; B01L 9/527; B01L 2200/10; B01L 2200/146; B01L 2200/0487; B01L 2200/12; B01L 3/5027; B01L 3/502707; B01L 3/502753; B01L 3/00; C40B 40/06; G01N 2021/058; G01N 2021/062; G01N 2021/068; G01N 30/603; G01N 30/02; H01L 21/00; C12Q 1/686

See application file for complete search history.

(56) References Cited

U.S. PATENT DOCUMENTS

| | | | |
|---|---|---|---|
| 3,335,946 A | 8/1967 | Putterlik | |
| 3,884,805 A | 5/1975 | Bagdasarian et al. | |
| 3,948,779 A | 4/1976 | Jackson | |
| 4,267,045 A | 5/1981 | Hoof | |
| 4,410,430 A | 10/1983 | Hagler, Jr. | |
| 4,423,090 A | 12/1983 | Hammond, Jr. et al. | |
| 4,430,232 A | 2/1984 | Doucet | |
| 4,478,769 A | 10/1984 | Pricone et al. | |
| 4,486,363 A | 12/1984 | Pricone et al. | |
| 4,601,861 A | 7/1986 | Pricone et al. | |
| 4,620,917 A | 11/1986 | Nozawa et al. | |
| 4,668,558 A | 5/1987 | Barber | |
| 4,797,175 A | 1/1989 | Ellion et al. | |
| 4,842,739 A | 6/1989 | Tang | |
| 4,842,794 A | 6/1989 | Hovis et al. | |
| 4,882,047 A * | 11/1989 | Shalon ............ | B01D 15/14 210/198.2 |
| 4,891,120 A | 1/1990 | Sethi et al. | |
| 4,902,420 A | 2/1990 | Pall et al. | |
| 4,960,449 A | 10/1990 | Yonushonis | |
| 4,971,769 A | 11/1990 | Haerle | |
| 5,009,857 A | 4/1991 | Haerle | |
| 5,100,551 A | 3/1992 | Pall et al. | |
| 5,200,073 A | 4/1993 | Steere et al. | |
| 5,204,690 A | 4/1993 | Lorenze, Jr. et al. | |
| 5,207,962 A | 5/1993 | Hovis et al. | |
| 5,262,107 A | 11/1993 | Hovis et al. | |
| 5,290,447 A | 3/1994 | Lippold | |
| 5,298,226 A * | 3/1994 | Nowobilski ....... | B01D 53/0446 422/171 |
| 5,505,852 A | 4/1996 | van Rossen | |
| 5,552,046 A | 9/1996 | Johnston et al. | |
| 5,568,819 A | 10/1996 | Gentry et al. | |
| 5,645,704 A | 7/1997 | Axtman | |
| 5,726,026 A * | 3/1998 | Wilding ............ | B01D 67/0062 366/DIG. 3 |
| 5,985,164 A | 11/1999 | Chu et al. | |
| 6,273,938 B1 | 8/2001 | Fanselow et al. | |
| 6,274,035 B1 | 8/2001 | Yuan et al. | |
| 6,284,072 B1 | 9/2001 | Ryan et al. | |
| 6,306,300 B1 | 10/2001 | Harding et al. | |
| 6,346,192 B2 | 2/2002 | Buhr et al. | |
| 6,375,870 B1 | 4/2002 | Visovsky et al. | |
| 6,391,097 B1 | 5/2002 | Rosenberg | |
| 6,471,746 B2 | 10/2002 | Hagglund et al. | |
| 6,524,488 B1 | 2/2003 | Insley et al. | |
| 6,589,317 B2 | 7/2003 | Zhang et al. | |
| 6,632,357 B1 | 10/2003 | Barger et al. | |
| 6,685,833 B2 | 2/2004 | Lippold | |
| 6,685,841 B2 | 2/2004 | Lopez et al. | |
| 6,746,890 B2 | 6/2004 | Gupta et al. | |
| 6,748,978 B2 | 6/2004 | Pezzuto et al. | |
| 6,752,889 B2 | 6/2004 | Insley et al. | |
| 6,761,962 B2 | 7/2004 | Bentsen et al. | |
| 6,827,906 B1 | 12/2004 | Bjornson et al. | |
| 6,872,302 B2 | 3/2005 | Aste | |
| 6,915,566 B2 | 7/2005 | Abbott et al. | |
| 6,936,086 B2 | 8/2005 | Harkonen et al. | |
| 7,032,426 B2 | 4/2006 | Durney et al. | |
| 7,048,848 B2 | 5/2006 | Assion | |
| 7,081,208 B2 | 7/2006 | McCullough et al. | |
| 7,104,406 B2 | 9/2006 | Chen et al. | |
| 7,122,068 B2 | 10/2006 | Tate et al. | |
| 7,163,733 B2 | 1/2007 | Bourdelais et al. | |
| 7,217,562 B2 | 5/2007 | Cao et al. | |
| 7,223,364 B1 | 5/2007 | Johnston et al. | |
| 7,238,255 B2 | 7/2007 | Derand et al. | |
| 7,282,148 B2 | 10/2007 | Dalton et al. | |
| 7,323,105 B1 | 1/2008 | Janikowski et al. | |
| 7,425,227 B1 | 9/2008 | Hutchison et al. | |
| 7,442,303 B2 | 10/2008 | Jacobson | |
| 7,531,120 B2 | 5/2009 | Van Rijn et al. | |
| 7,569,139 B2 | 8/2009 | Mihlbauer et al. | |
| 7,588,619 B2 | 9/2009 | Chilton et al. | |
| 7,645,383 B2 | 1/2010 | Kadel et al. | |
| 7,784,619 B2 | 8/2010 | Jacobson | |
| 7,857,978 B2 | 12/2010 | Jensen et al. | |
| 7,901,758 B2 | 3/2011 | Rasmussen | |
| 7,922,795 B2 | 4/2011 | Striemer et al. | |
| 7,959,780 B2 | 6/2011 | Hawkins et al. | |
| 7,988,840 B2 | 8/2011 | Huang et al. | |
| 7,994,592 B2 * | 8/2011 | Tai .................... | B01L 3/502707 257/414 |
| 8,025,854 B2 | 9/2011 | Ohman et al. | |
| 8,083,941 B2 | 12/2011 | Chien | |
| 8,179,381 B2 | 5/2012 | Frey et al. | |
| 8,186,913 B2 | 5/2012 | Toner et al. | |
| 8,197,775 B2 | 6/2012 | Johnston et al. | |
| 8,273,245 B2 | 9/2012 | Jovanovic et al. | |
| 8,277,759 B2 | 10/2012 | Sundberg et al. | |
| 8,282,799 B2 | 10/2012 | Huang et al. | |
| 8,297,449 B2 | 10/2012 | Afzali-Ardakani et al. | |
| 8,304,230 B2 | 11/2012 | Toner et al. | |
| 8,328,022 B2 | 12/2012 | Mbadinga-Mouanda et al. | |
| 8,679,336 B2 | 3/2014 | Hongo et al. | |
| 2002/0060183 A1 | 5/2002 | Paul et al. | |
| 2002/0125192 A1 | 9/2002 | Lopez et al. | |
| 2002/0185003 A1 | 12/2002 | Potter | |
| 2003/0104170 A1 | 6/2003 | Johnston et al. | |
| 2003/0118781 A1 | 6/2003 | Insley et al. | |
| 2003/0134416 A1 * | 7/2003 | Yamanishi ............ | A61M 1/36 435/372 |
| 2004/0000519 A1 * | 1/2004 | Jiang .................. | G01N 30/0005 210/634 |
| 2004/0159319 A1 | 8/2004 | Kadel et al. | |
| 2005/0179150 A1 | 8/2005 | Bharadwaj et al. | |
| 2006/0219627 A1 | 10/2006 | Rodgers et al. | |
| 2006/0254972 A1 * | 11/2006 | Tai .......... | B01D 61/14 210/321.6 |
| 2006/0266692 A1 * | 11/2006 | Foster ........... | B01D 61/14 210/321.84 |
| 2007/0020772 A1 | 1/2007 | Cao et al. | |

(56) References Cited

U.S. PATENT DOCUMENTS

| | | |
|---|---|---|
| 2007/0151920 A1 | 7/2007 | Kay |
| 2007/0246433 A1 | 10/2007 | Zuberi |
| 2007/0251867 A1 | 11/2007 | Mihlbauer et al. |
| 2008/0012151 A1 | 1/2008 | Kemppainen et al. |
| 2008/0014410 A1 | 1/2008 | Johnston et al. |
| 2008/0296238 A1 | 12/2008 | Haldopoulos et al. |
| 2009/0102094 A1 | 4/2009 | Golden et al. |
| 2009/0120874 A1 | 5/2009 | Jensen et al. |
| 2009/0149345 A1 | 6/2009 | Nishi et al. |
| 2010/0028604 A1 | 2/2010 | Bhushan et al. |
| 2010/0216126 A1 | 8/2010 | Balachandran et al. |
| 2010/0317132 A1 | 12/2010 | Rogers et al. |
| 2011/0100900 A1 | 5/2011 | Drury et al. |
| 2011/0108522 A1* | 5/2011 | Rozing ............. B01L 3/502753 216/54 |
| 2011/0240476 A1 | 10/2011 | Wang et al. |
| 2012/0003711 A1* | 1/2012 | Tseng ................ B01L 3/502707 435/177 |
| 2012/0006760 A1 | 1/2012 | Toner et al. |
| 2012/0037544 A1 | 2/2012 | Lane et al. |
| 2012/0244311 A1 | 9/2012 | Manninen |
| 2012/0244314 A1 | 9/2012 | Scheibner et al. |
| 2012/0258459 A1* | 10/2012 | Huang .................. B01L 3/5021 435/6.11 |
| 2012/0261331 A1 | 10/2012 | Ter Horst et al. |
| 2012/0261333 A1 | 10/2012 | Moran et al. |
| 2012/0267249 A1 | 10/2012 | Cotte et al. |
| 2012/0273990 A1 | 11/2012 | O'Donnell et al. |
| 2013/0008848 A1 | 1/2013 | Jonsson et al. |
| 2013/0078163 A1 | 3/2013 | Chung et al. |
| 2014/0221544 A1 | 8/2014 | Lichtenhan et al. |
| 2014/0224658 A1 | 8/2014 | Richardson |
| 2015/0367257 A1 | 12/2015 | Richardson |
| 2016/0236120 A1 | 8/2016 | Richardson |
| 2017/0008781 A1 | 1/2017 | Richardson |
| 2017/0050407 A1 | 2/2017 | Richardson |

FOREIGN PATENT DOCUMENTS

| | | |
|---|---|---|
| EP | 0639223 B1 | 2/1995 |
| EP | 1196242 A1 | 4/2002 |
| EP | 1197255 A1 | 4/2002 |
| EP | 1254689 B1 | 11/2002 |
| EP | 1449585 A1 | 8/2004 |
| EP | 2505047 A2 | 10/2012 |
| WO | WO2011066055 A2 | 6/2011 |
| WO | WO2014116183 A1 | 7/2014 |
| WO | WO2015105524 A1 | 7/2015 |
| WO | WO2015199663 A1 | 12/2015 |
| WO | WO2016037150 A1 | 3/2016 |
| WO | WO2016133929 A1 | 8/2016 |
| WO | WO2017007734 A1 | 1/2017 |

OTHER PUBLICATIONS

Non-Final Office Action, dated Mar. 11, 2016, U.S. Appl. No. 14/149,620, filed Jan. 7, 2014.
Brown, R.C., "Electrically Charged Filter Materials," Engineering Science and Education Journal 1.2 (1992): 71-79.
Patent Cooperation Treaty Application No. PCT/US2016040878, "International Search Report" and "Written Opinion of he International Searching Authority," Sep. 19, 2016, 11 pages.
International Search Report and Written Opinion dated May 19, 2016 in Application No. PCT/US2016/018119, filed Feb. 16, 2016, 10 pages.
International Search Report and Written Opinion dated Aug. 28, 2014 in Application No. PCT/US2014/036439, filed May 1, 2014.
International Search Report and Written Opinion dated Dec. 1, 2014 in Application No. PCT/US2014/043942, filed Jun. 24, 2014.
International Search Report and Written Opinion dated Dec. 17, 2015 in Application No. PCT/US2015/048723, filed Sep. 4, 2015.
Non-Final Office Action, dated Dec. 21, 2016, U.S. Appl. No. 14/701,528, filed May 1, 2015.
Non-Final Office Action, dated Jan. 12, 2017, U.S. Appl. No. 15/045,119, filed Feb. 16, 2016.
Non-Final Office Action, dated Jan. 12, 2017, U.S. Appl. No. 14/313,924, filed Jun. 24, 2014.
Non-Final Office Action, dated Jan. 25, 2017, U.S. Appl. No. 15/233,701, filed Aug. 10, 2016.

* cited by examiner

Microstructure area

Layered microstructure

Layered Microstructure Fabrication Process

Substrate

Apply sacrificial layer

Apply structural layers

Repeat sacrificial and structural layers many times

Etch main channels in both sacrificial and structural layers

Partially etch away the sacrificial layers

MICROSTRUCTURE SEPARATION FILTERS

CROSS REFERENCE TO RELATED APPLICATIONS

This application claims the priority benefit of U.S. Provisional Application Ser. No. 62/070,778, filed Sep. 5, 2014; U.S. Provisional Application Ser. No. 62/123,717, filed Nov. 25, 2014; U.S. Provisional Application Ser. No. 62/176,125, filed on Feb. 9, 2015; and U.S. Provisional Application Ser. No. 62/179,582, filed May 11, 2015, all of which are hereby incorporated by reference herein in their entireties, including all references cited therein. This application is also related to U.S. patent application Ser. No. 14/701,528, filed on May 1, 2015, which is hereby incorporated by reference here in its entirety, including all references cited therein.

FIELD OF THE PRESENT TECHNOLOGY

The present technology relates generally to separation filters and chromatography, and more specifically, but not by limitation, to microstructure substrates that comprise microstructured panels, complex flow orifices, and various types of filtering systems configured from these substrates, such as chromatography devices.

SUMMARY OF THE PRESENT TECHNOLOGY

According to some embodiments, the present technology may be directed to a chromatography or other type of separation device, comprising: (a) a microstructure filter comprising a plurality of layers of structural material which are spaced apart to create inlet channels and outlet channels, wherein adjacent ones of the inlet channels and the outlet channels are spaced apart from one another by cross channels that filter a fluid from the inlet channels to the outlet channels, the cross channels comprising filter features formed by removing a portion of the plurality of layers of the structural material; and (b) a housing configured to receive the microstructure filter, the housing being configured to connect to a device to test the fluid.

The present technology may be directed to a filter device, comprising: (a) a microstructure filter comprising a plurality of layers of sacrificial material and an outer layer of structural material, which have been etched to create inlet channels and outlet channels, wherein adjacent ones of the inlet channels and the outlet channels are spaced apart from one another by cross channels that filter a fluid from the inlet channels to the outlet channels, the cross channels comprising filter features formed by etching away of a portion of the sacrificial layers, wherein the plurality of layers of sacrificial material comprise: (i) a base material; (ii) a first of sections of sacrificial material are spaced apart from one another equidistantly, the first layer disposed on the base material; (iii) second layer deposited on the first layer, the second layer comprising pairs of sections of sacrificial offset from the sections of the first layer so as to cover spaces between the sections of the first layer; (iv) a third layer deposited on the second layer, the second layer comprising triplets of sections of sacrificial offset from the sections of the second layer; (v) a fourth layer deposited on the third layer, wherein sections are contiguous and extend across half of the microstructure filter length; and (vi) the outer layer of structural material being disposed on the fourth layer; and (b) a housing configured to receive the microstructure filter, the housing being configured to connect to a chromatograph device to test the fluid.

According to still other embodiments, the present technology may be directed to a filter device, comprising: (a) a microstructure filter comprising cross channels that filter a fluid from inlet channels to outlet channels, the cross channels comprising microstructure filter features formed by etching away of a portion of the sacrificial layers, the microstructure filter features comprising nanostructures that increase a surface area of the filter features to attract particles present in the fluid as the fluid passes through the filter features from the inlet channels to the outlet channels; and (b) a housing configured to receive the microstructure filter, the housing being configured to connect to a chromatograph device to test the fluid.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

DESCRIPTION OF EXEMPLARY EMBODIMENTS

Figure 1:
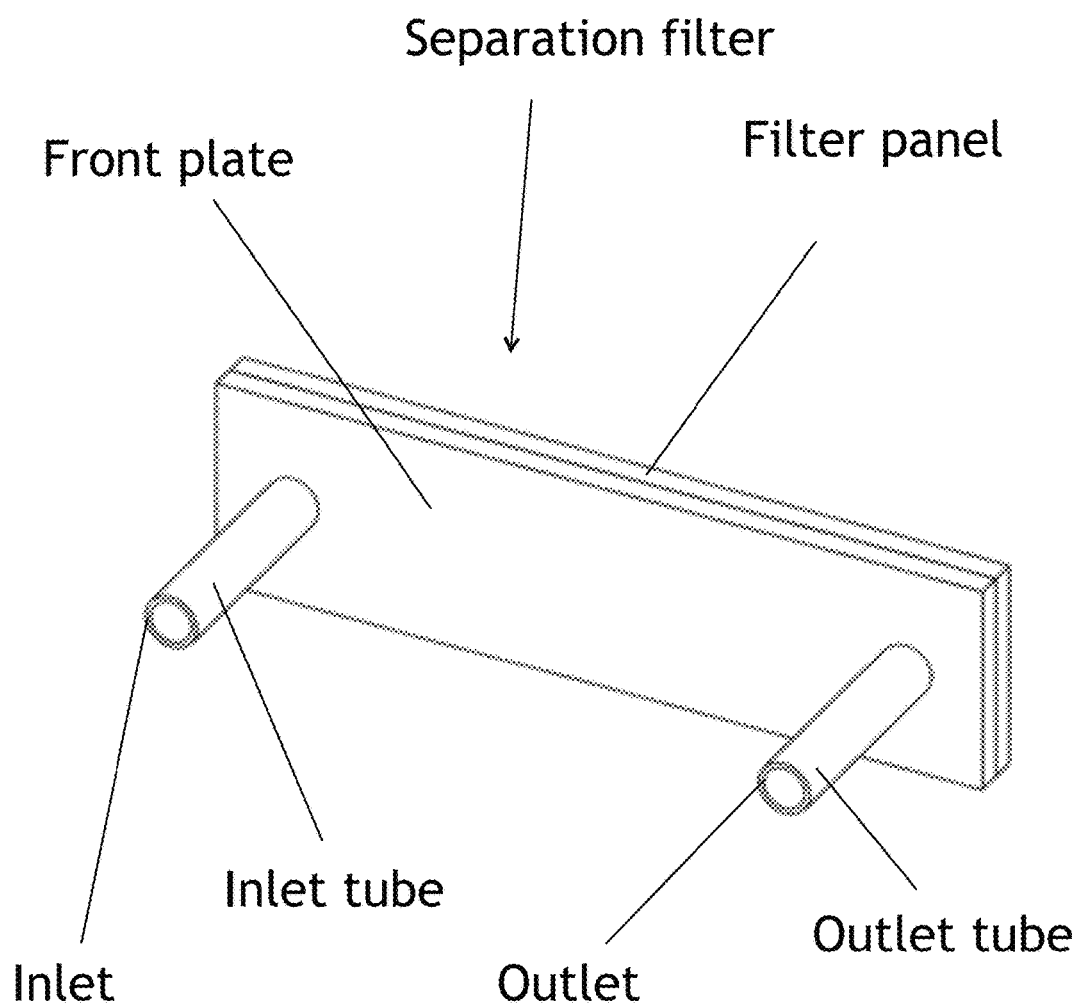
FIG. 1 is an isometric view of the separation filter, constructed in accordance with the present technology.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the present technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

FIGS. 1-22 collectively illustrate separation filters with microstructured panels. The microstructured panels are precisely replicated on a film from tooling made with semiconductor processing techniques. The separation panels can be covered with a front cover or layered on top of one another to form enclosed panels. The flow of liquids through the microstructured panels can be affected by coating the surfaces of the panels with materials or be constructed of materials that attract or repel particles or molecules in the fluid. Alternately separation panels can be made from semiconductor materials rather than being replicated from a semiconductor master.

Referring first to FIG. 1, the separation filter is shown. Fluids flow into the separation filter at the inlet tube. The opening in the inlet tube extends through the front plate. Fluids exiting the separation filter do so via the outlet tube. The opening in the outlet tube also extends through the front plate. The filter panel is sealed to the back side of the front plate. The back side of the front panel would be generally a flat surface and is not shown.

Figure 2:
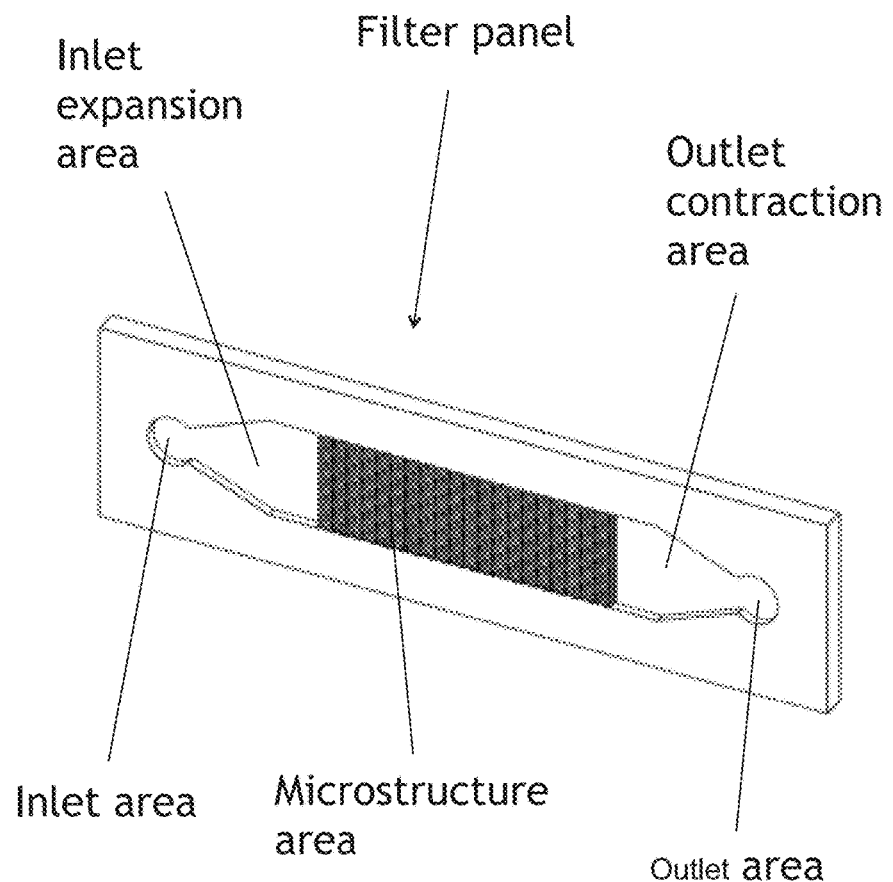
FIG. 2 is an isometric view of the filter panel of FIG. 1.
Figure 3:
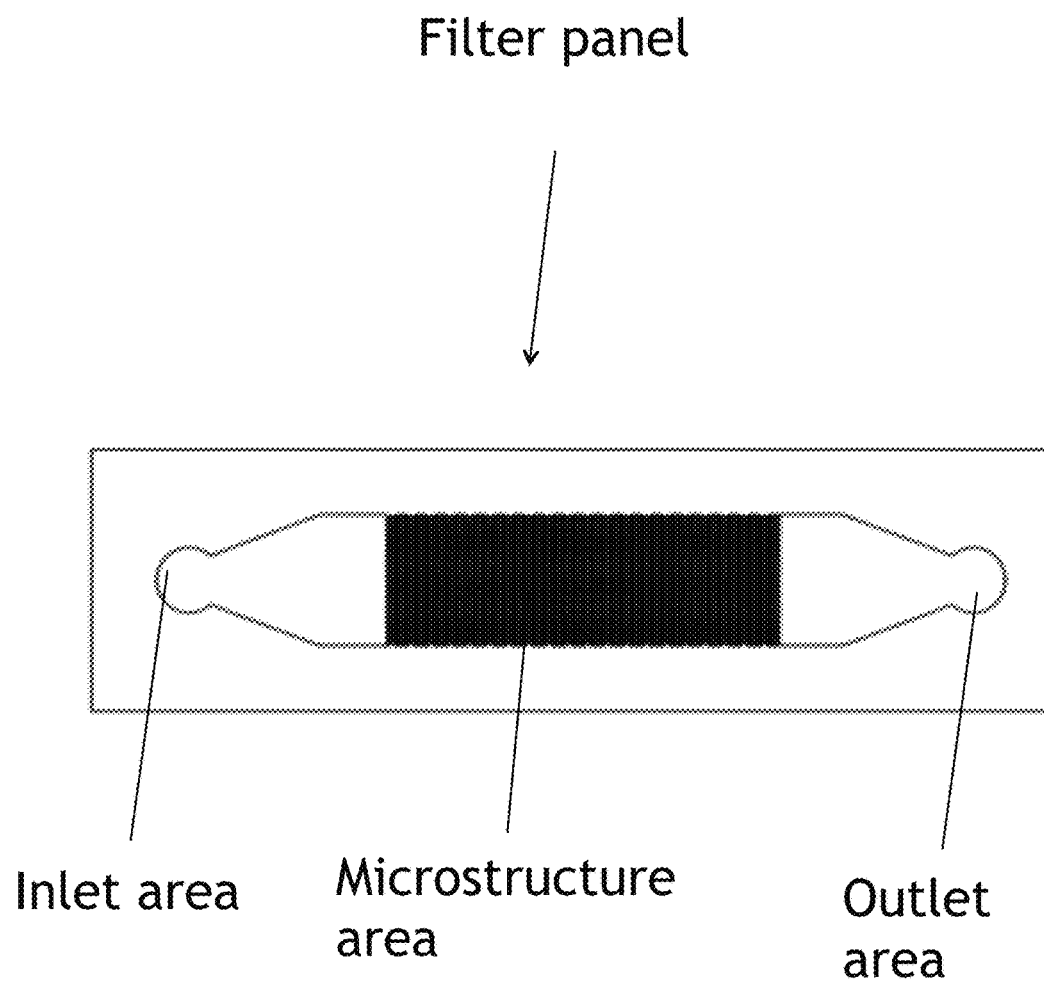
FIG. 3 is a front view of the filter panel shown in FIG. 2.
Figure 4:
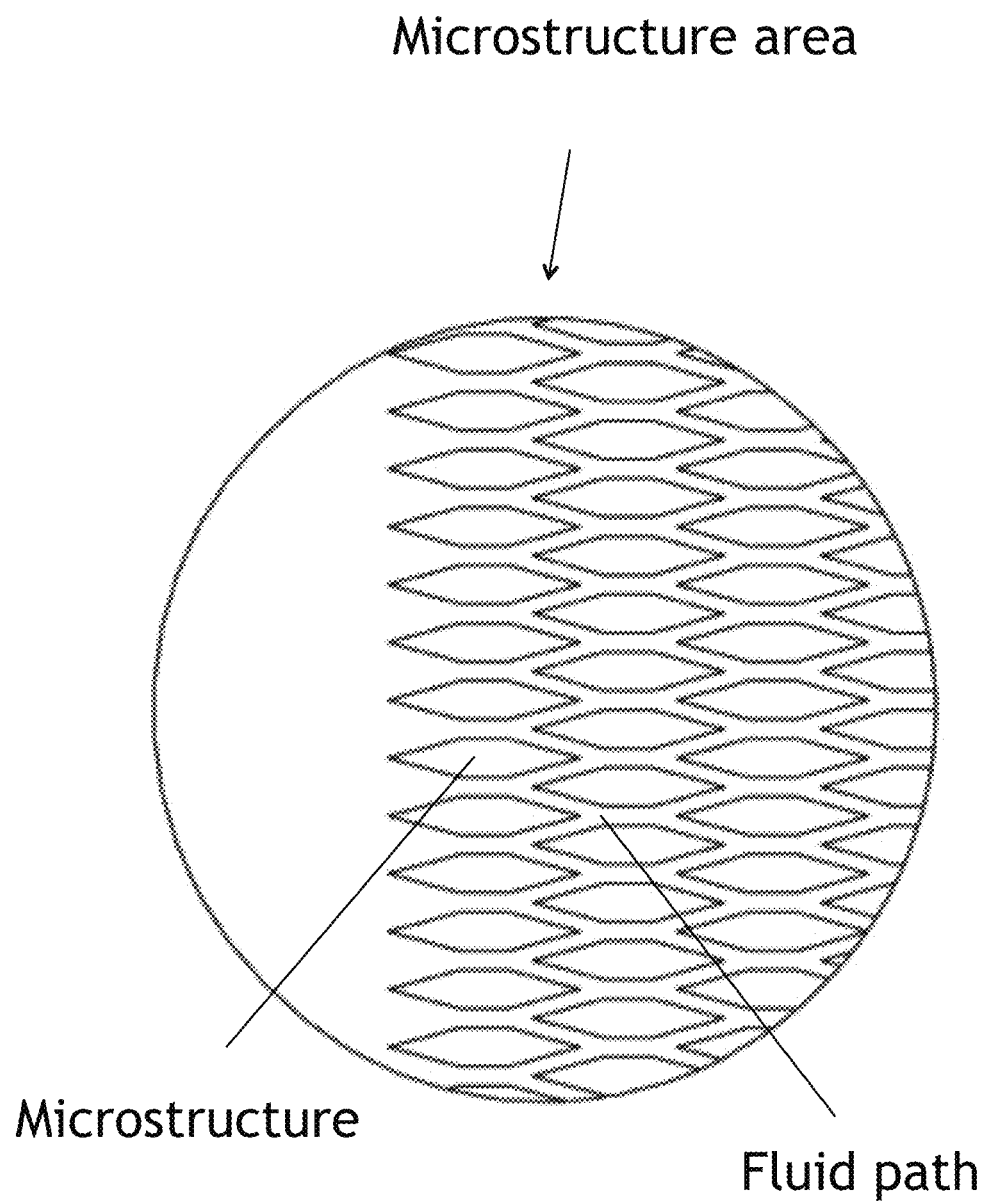
FIG. 4 is a close-up front view of the microstructure area shown in FIG. 3.

Referring to FIG. 2 the filter panel is shown without the inlet tube, the outlet tube and the front cover. The inlet area is coincident with the opening in the inlet tube. Similarly the outlet area is coincident with the opening in the outlet tube. The inlet area is a recessed pocket in the filter panel. Fluids flow from the inlet area to the inlet expansion area. The inlet expansion area is also a recessed pocket in the separation panel.

The cross section of the inlet expansion area is shown to increase along the flow path. The amount of expansion, or contraction would be a parameter that would be engineered for the specific application of the separation filter. The depth of the expansion is shown to be constant. This does not necessarily need to be the case.

The inlet expansion area is connected to the microstructure area. FIGS. 2, 3, 4 and 5 show the microstructure area at various angles and level of detail. The microstructure area shares the same depth as the inlet area and the inlet expansion area. Microstructures are generally as tall as the depth of the pocket.

As mentioned above the surface coating of the microstructure panel or the material composition of the microstructure panel would be of a type that interacts with compounds in the fluid. The removal of chemicals and or particles from drinking water is one applications of the disclosed separation filter. With this type of filter it is desirable to retain chemicals or particles from the fluid.

Another application of the separation panel is chromatography. When used in chromatography different compounds are usually separated from one another at different rates as fluid flows through the separation filter.

It should be noted that the coating and or materials deployed with the filter used for the specific separation task of the filter is not part of this invention. One skilled in the art of separation filters and the materials used for the specific application could engineer a material for a specific fluid.

Figure 5:
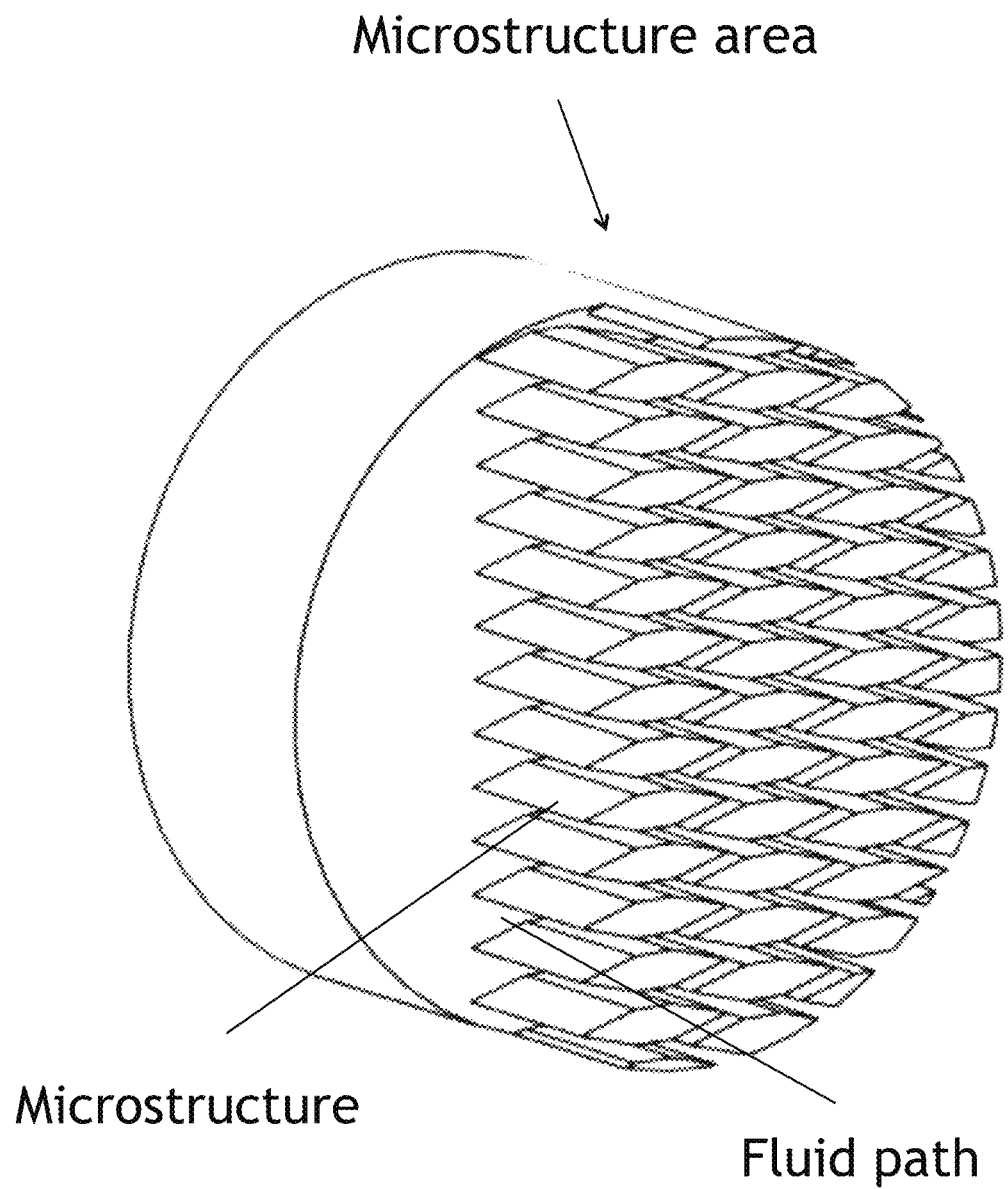
FIG. 5 is an isometric view of the microstructure area shown in FIG. 4.

Referring to FIG. 5 the microstructures can be seen in a magnified isometric view. The microstructures are generally a diamond shaped cross section and extend from the pocketed surface of the separation panel to the front face of the separation panel. This particular embodiment has a constant cross section from the base to the front face. The diamond microstructure geometry generally results in a constant cross section of the fluid path through the microstructure area.

Figure 6:
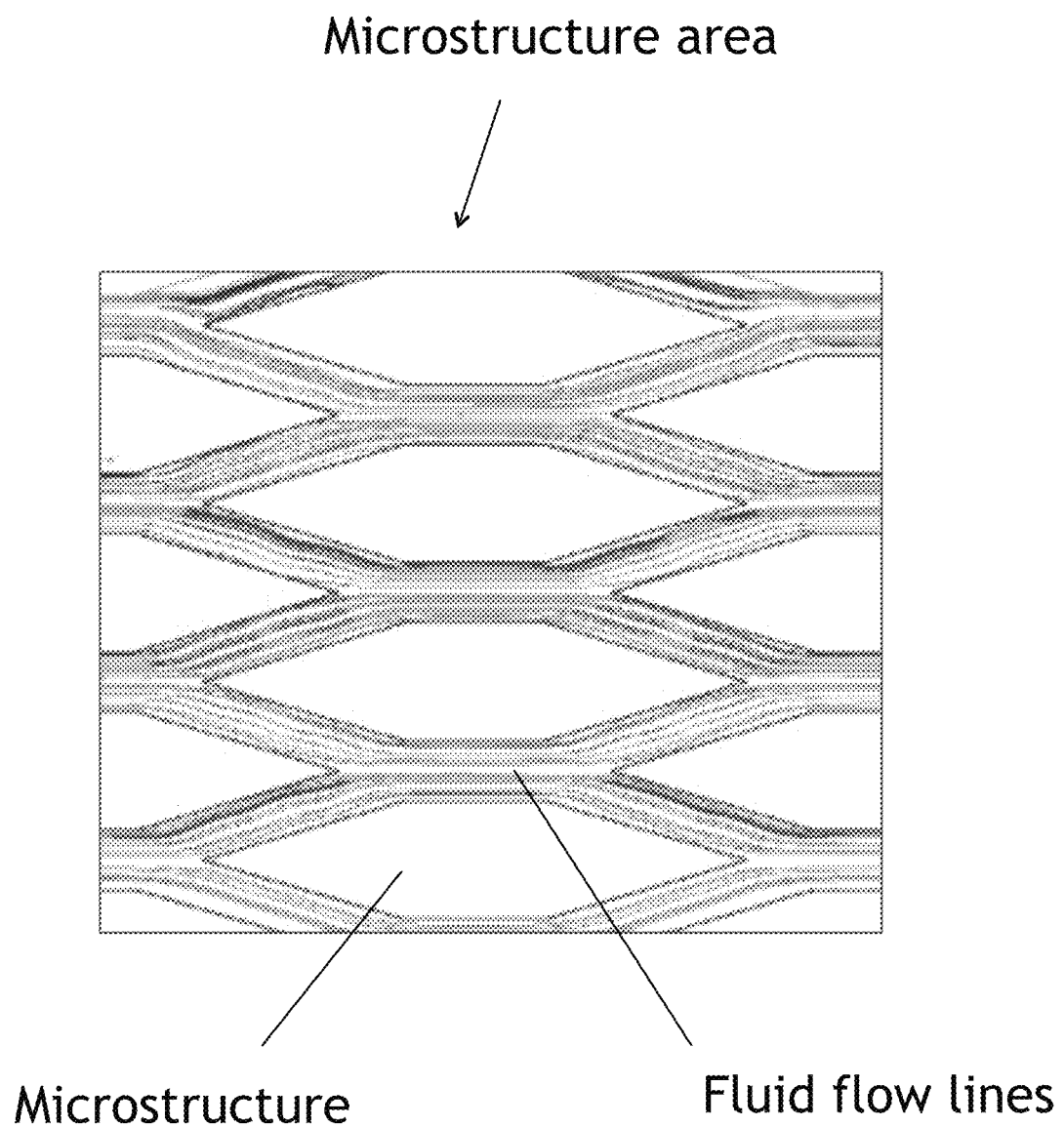
FIG. 6 is a close-up view similar to what is shown in FIG. 4 that includes fluid flow lines.

Referring to FIG. 6, flow lines of a fluid flowing around the microstructures is shown. These flow lines were generated with a computational fluids dynamics analysis. It should be noted that for most applications of the disclosed type filter the flow would be laminar in type.

As fluid flows along the surface of the microstructures, a boundary layer develops and grows in thickness. The fluid making contact with the surface of the filter microstructures is essentially stationary in relationship to the fluid flowing midway between adjacent microstructures. The further the fluid is from the surface of a microstructure the less likely a particle will be attracted to the surface of the microstructure.

The midway point is where the fluid velocity is greatest. This higher velocity fluid strikes the tips of the next column of microstructures. The boundary layer that begins to form at the tip of the next column of microstructures was previously the furthest away from the surface of the $1^{st}$ column of microstructures.

Figure 7:
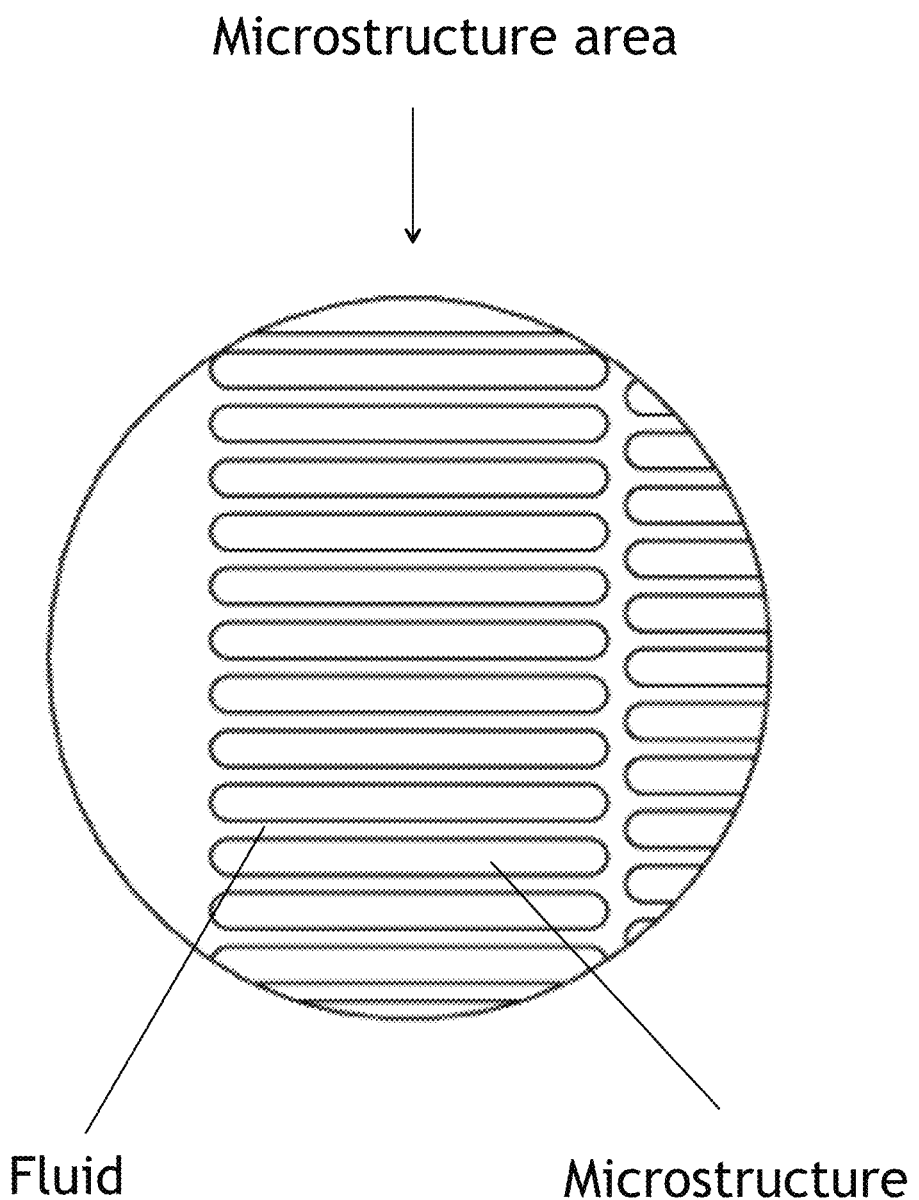
FIG. 7 is a close-up view similar to what is shown in FIG. 4 that shows an alternate embodiment.

Referring to FIG. 7 where an alternate embodiment of the microstructure is shown. These microstructures are also arranged to split the flow path as with the diamond design.

Figure 8:
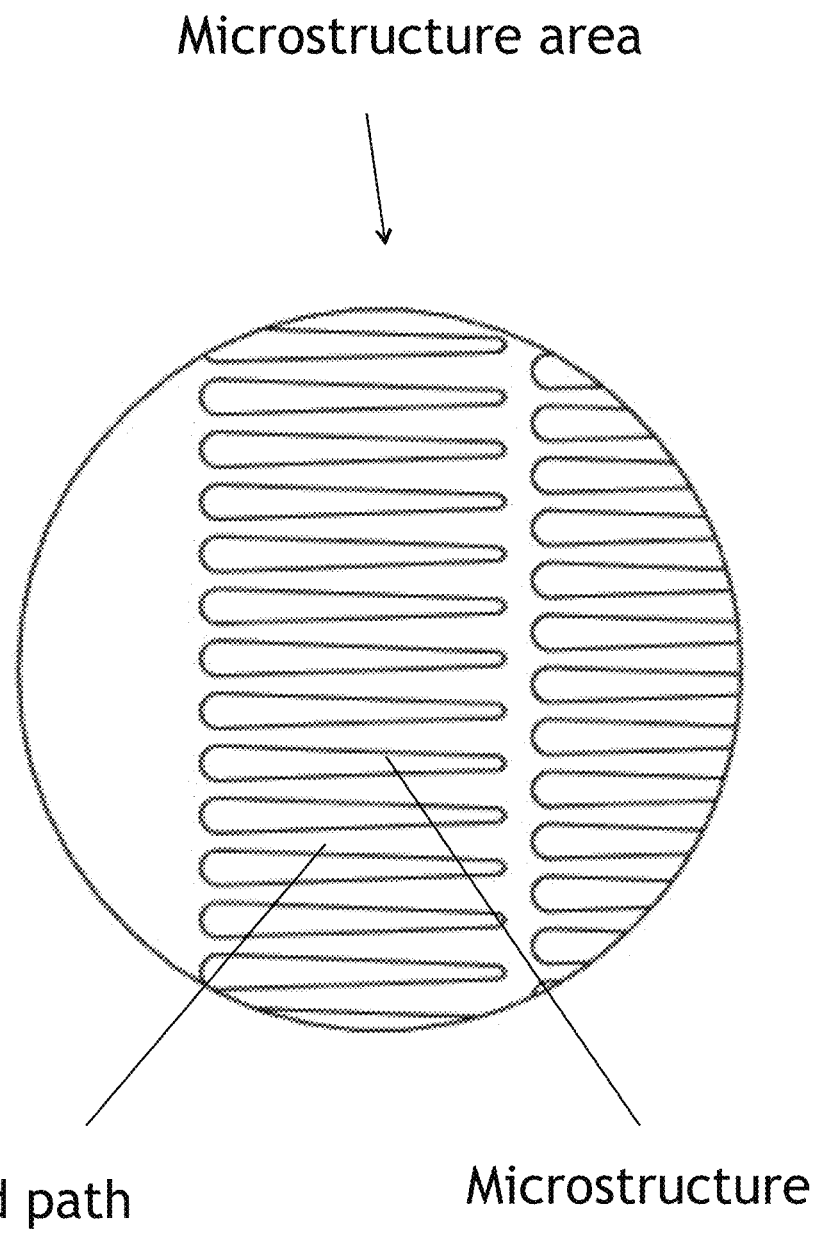
FIG. 8 is a close-up view similar to what is shown in FIG. 4 that shows an alternate embodiment.
Figure 9:
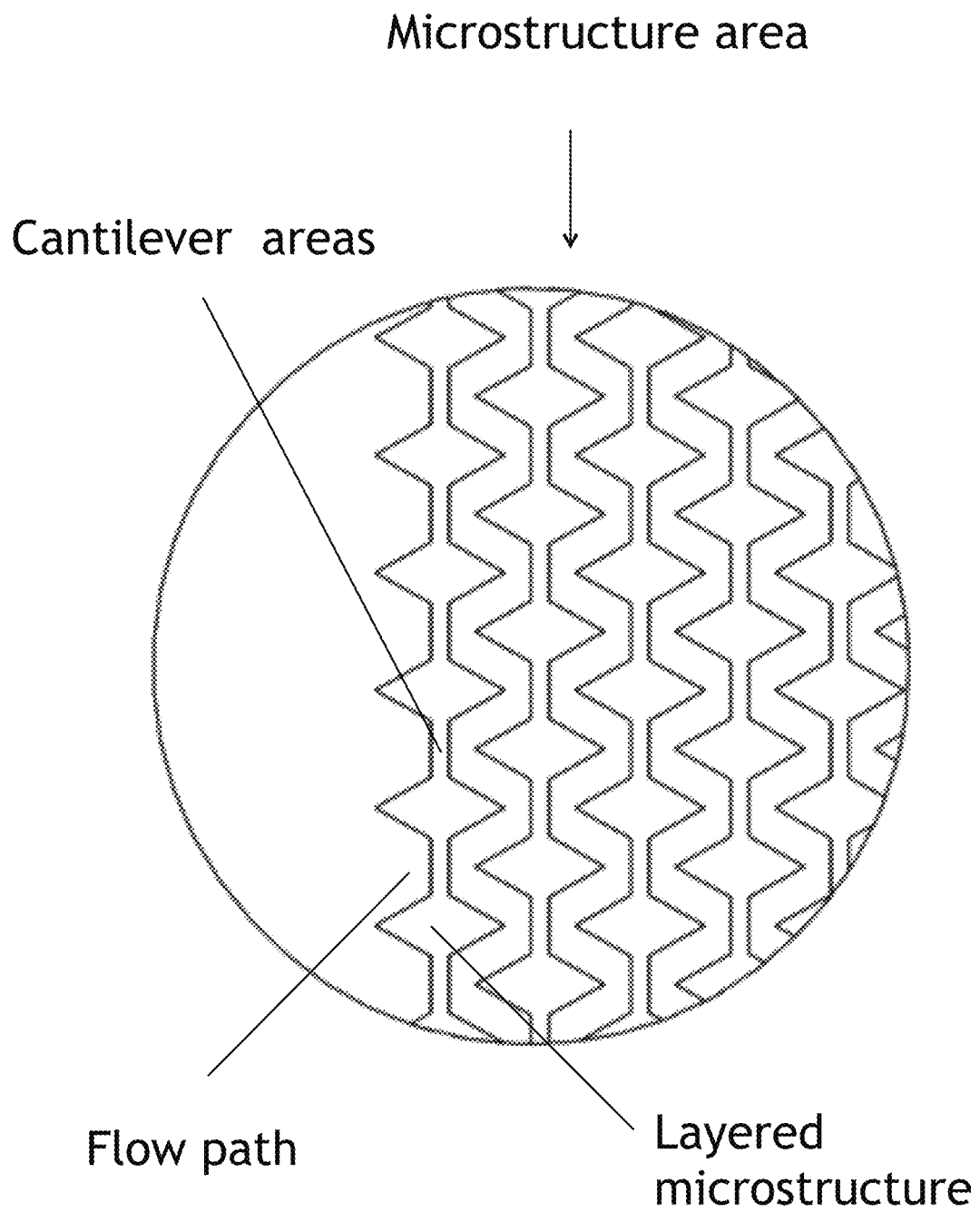
FIG. 9 is a close-up view similar to what is shown in FIG. 4 that shows an alternate embodiment.
Figure 10:
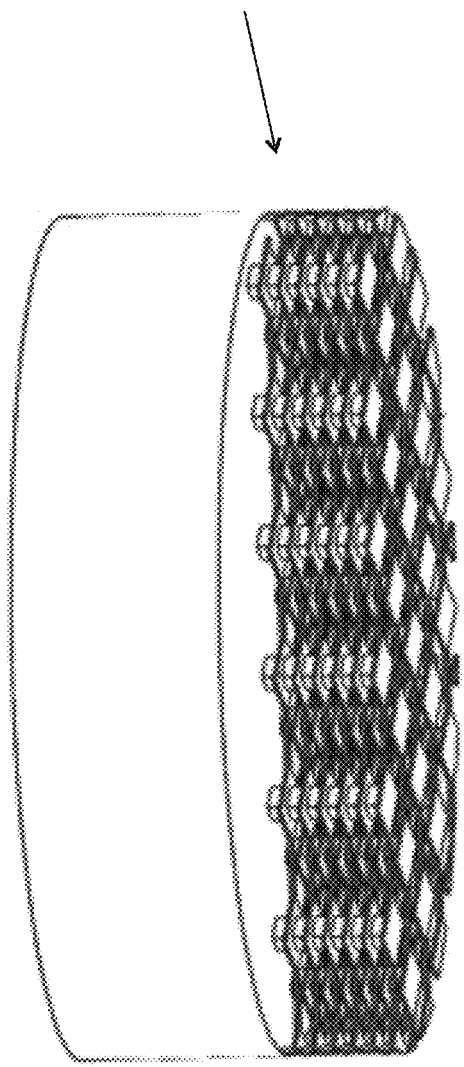
FIG. 10 is an isometric view of an alternate embodiment shown in FIG. 9.
Figure 11:
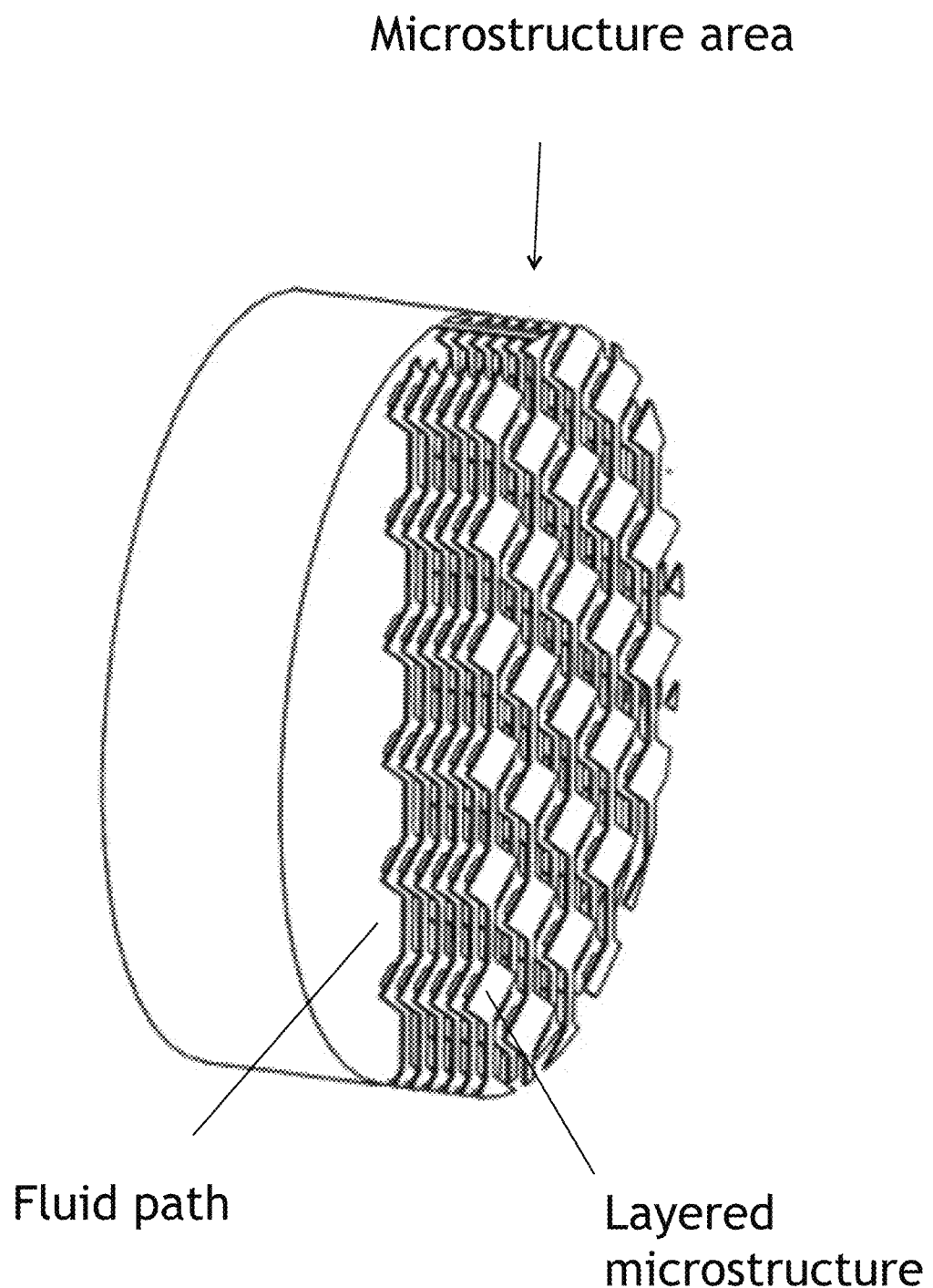
FIG. 11 is a different prospective of the isometric view shown in FIG. 10.
Figure 12:
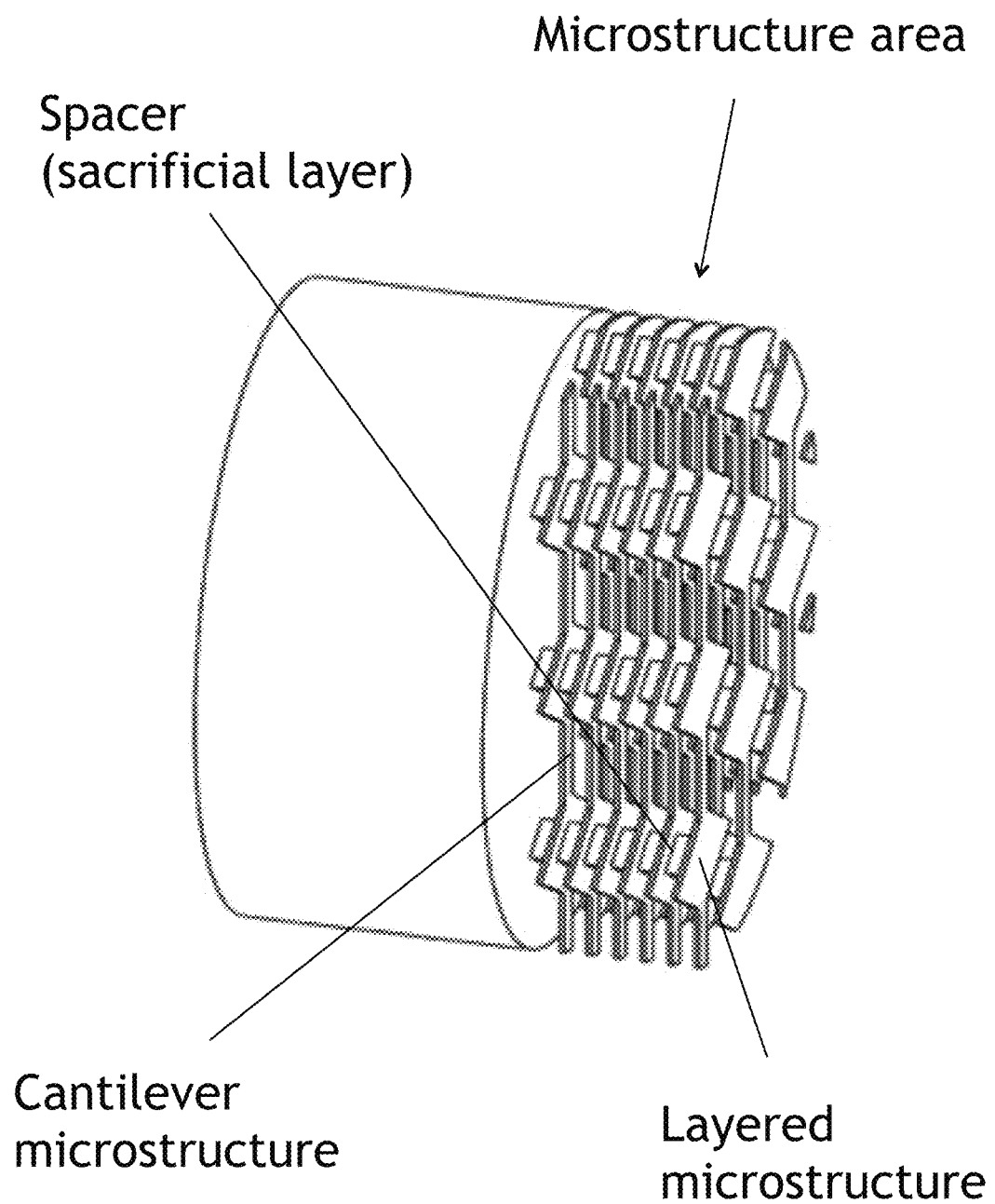
FIG. 12 is a close-up view of FIG. 10.
Figure 13:
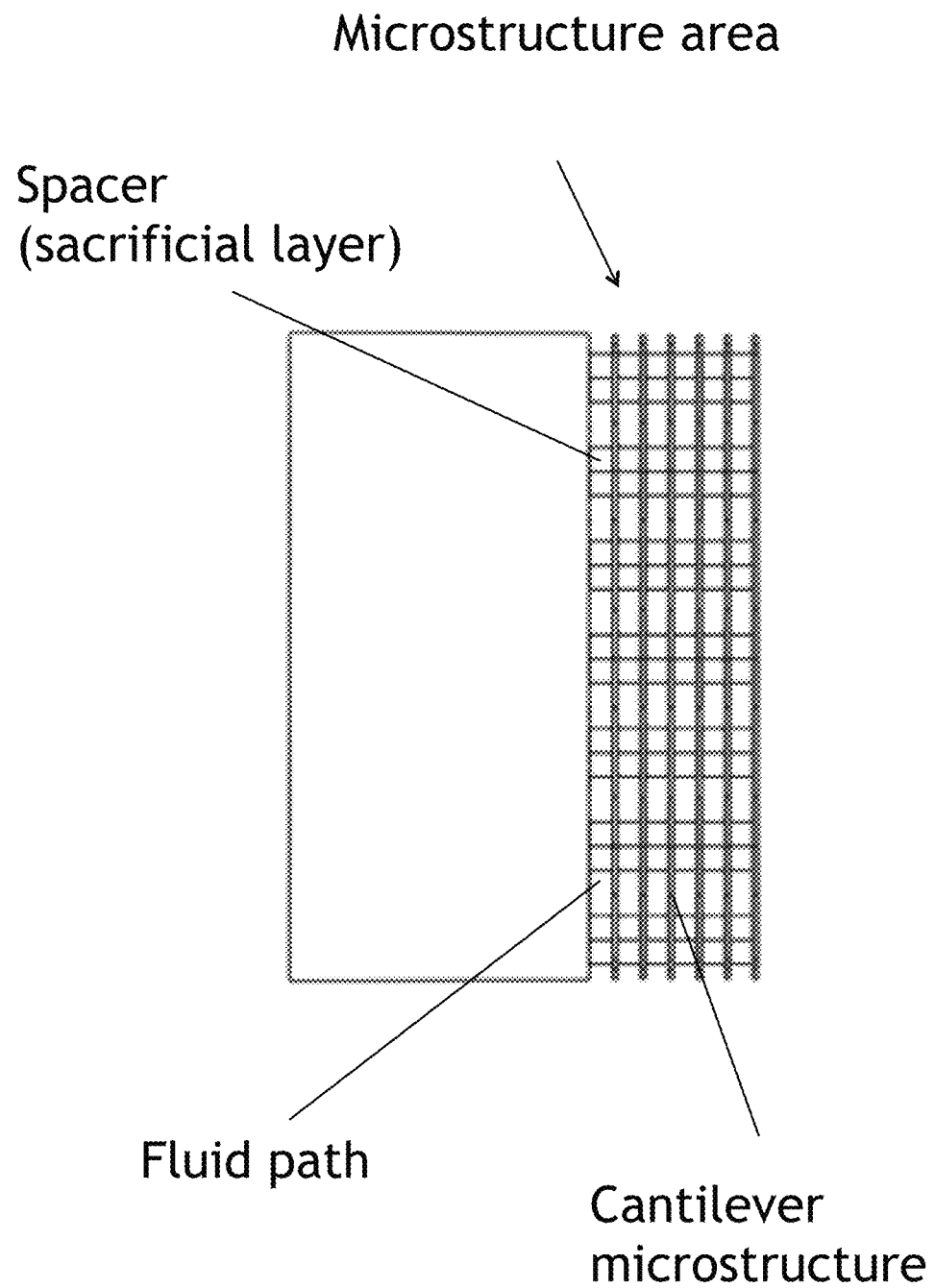
FIG. 13 is a side view of the close-up shown in FIG. 12.

Referring to FIG. 8 where another alternate embodiment of the microstructure is shown. The microstructures are tapered along the flow path to compensate for the growth of the boundary layers.

Referring to FIGS. 9, 10, 11, 12 and 13 where another alternate embodiment of the microstructure is shown. These microstructures differ from the previously disclosed microstructures in that they do not have a constant cross section. These microstructures have small spacers (in cross section) located between larger thin planes of structural material. This embodiment yields more surface area per section separation filter panel. Panels of this type require a more complex manufacturing process.

Figure 14:
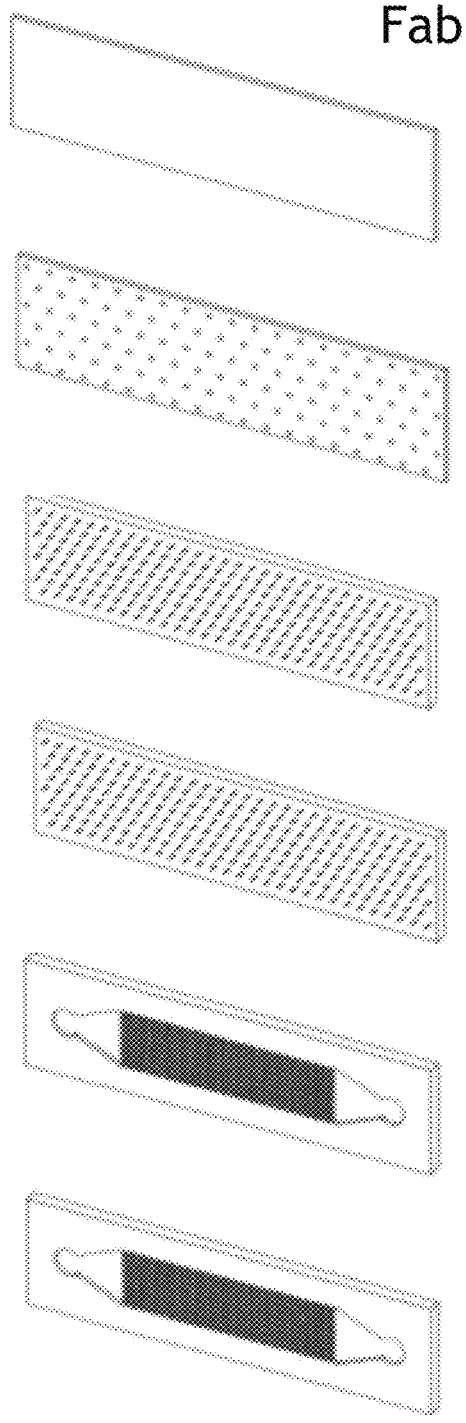
FIG. 14 shows the fabrication process for layered microstructures.

Referring to FIG. 14, the process to fabricate these microstructures is described.

Figure 15:
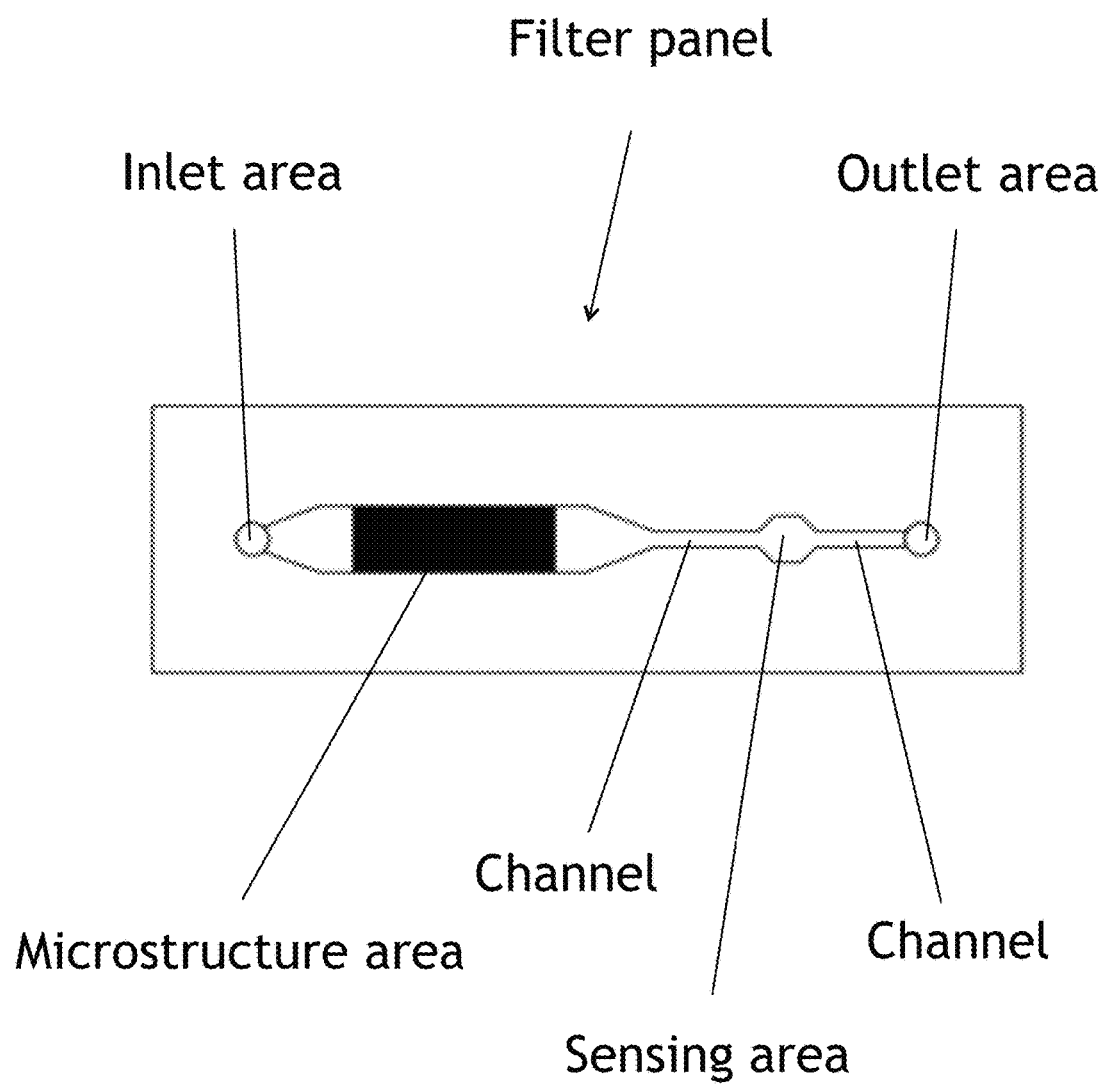
FIG. 15 is a front view of an alternate embodiment of the filter panel including a sensing area.

Referring to FIG. 15, additional "plumbing" has been added to the separation panel. Channels to and from a sensing area are shown. These additional features could be added to any of the embodiments disclosed in this disclosure. The sensing area could be used to measure the optical transmission or reflection of the fluid as it exits the separation filter. This would be useful in the case where the separation filter was used for chromatography.

Figure 16:
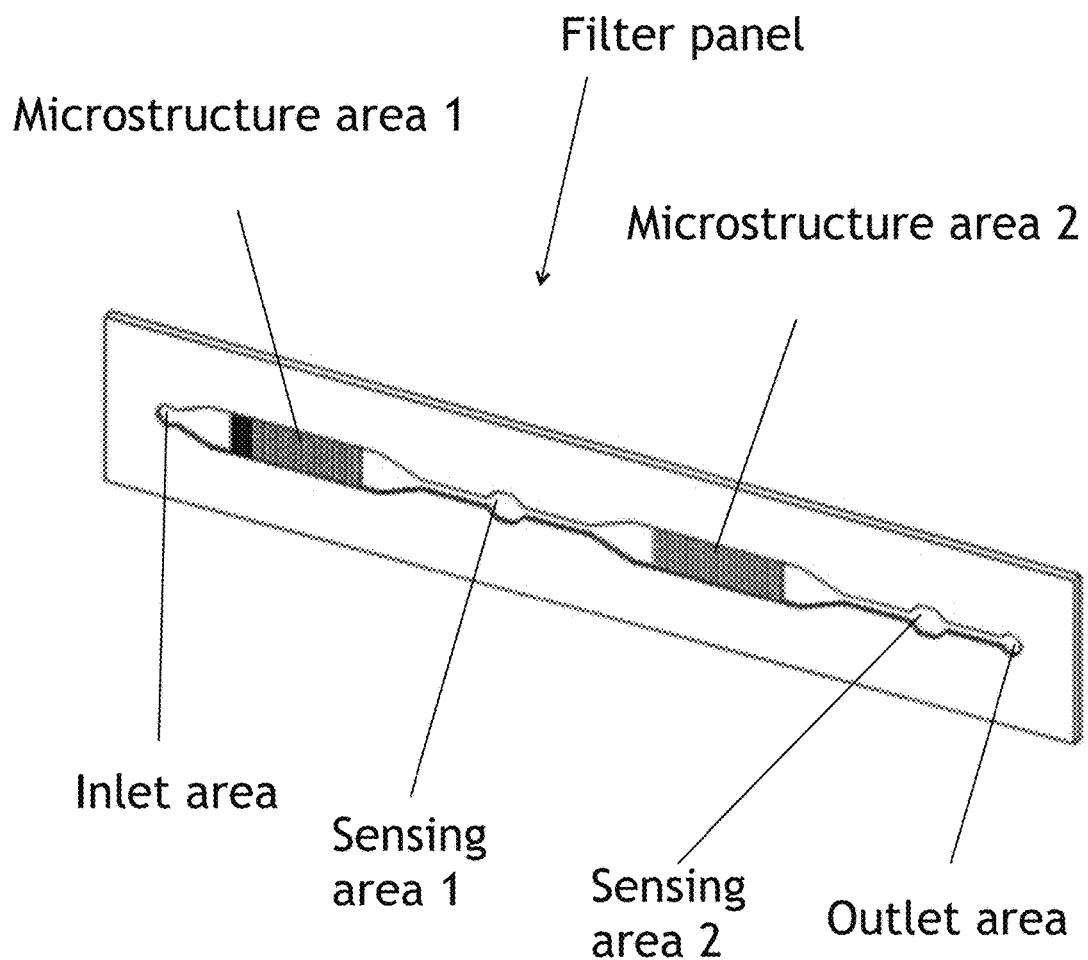
FIG. 16 is a front view of an alternate embodiment of the filter panel that includes two microstructure areas and two sensing areas.

Referring to FIG. 16, two different micro structured areas and two sensing areas are combined in series along the flow path. The first microstructure area might be coated with a different material than the second area.

Figure 17:
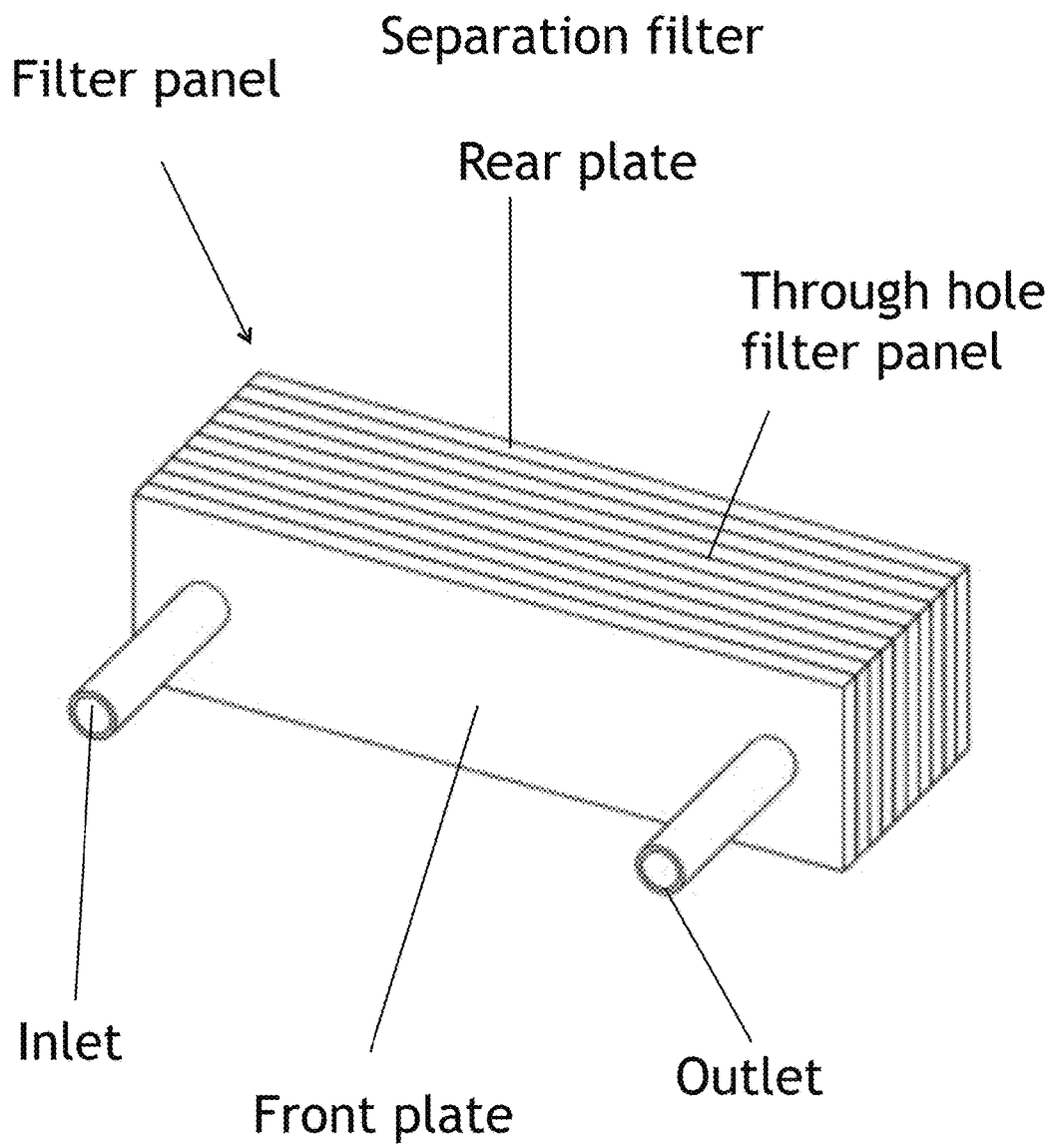
FIG. 17 is an isometric view of an alternate embodiment of the separation filter with multiple filter panels.

Referring to FIG. 17 where another alternate embodiment of a separation filter is shown. The separation filter is configured with many through hole filter panels sandwiched between the front panel and the rear panel.

Figure 18:
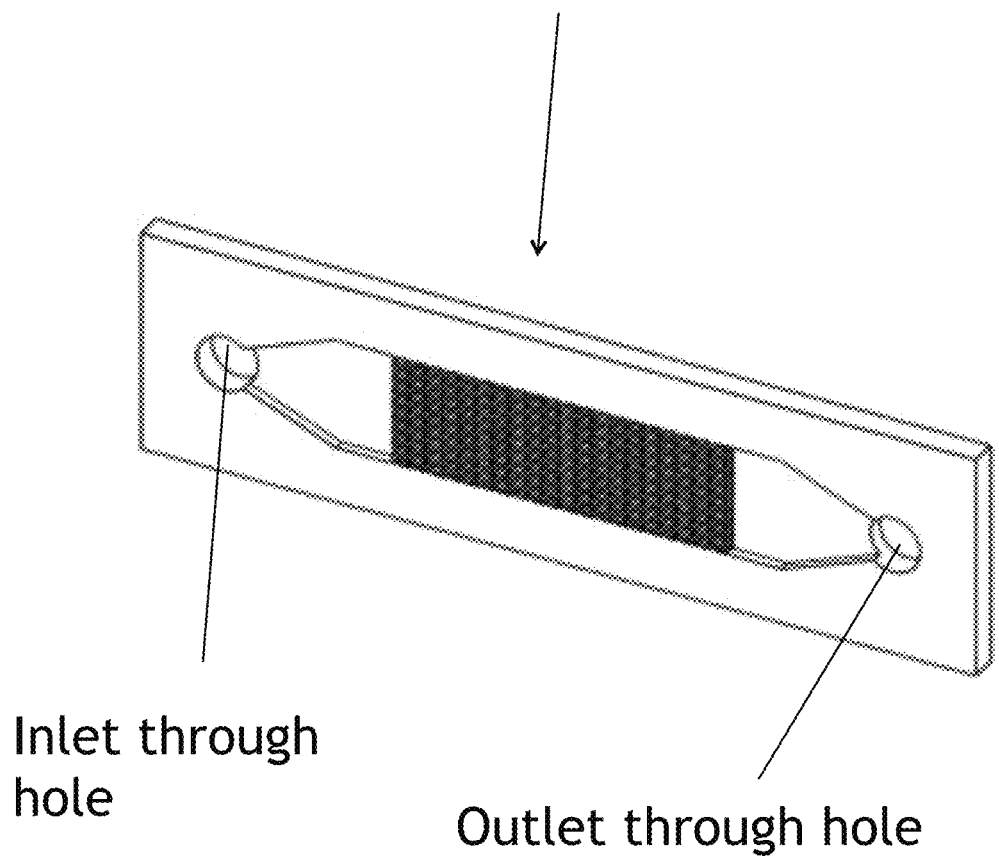
FIG. 18 is an isometric view of the through hole filter panel section shown in FIG. 17.

Referring to FIG. 18, the through hole filter panel is shown. The inlet area of the through hole filter panels pass all the way through the panel. This allows inlet and outlet fluids to flow to all of the panels in the sandwich. The rear panel doesn't have any holes.

Figure 19:
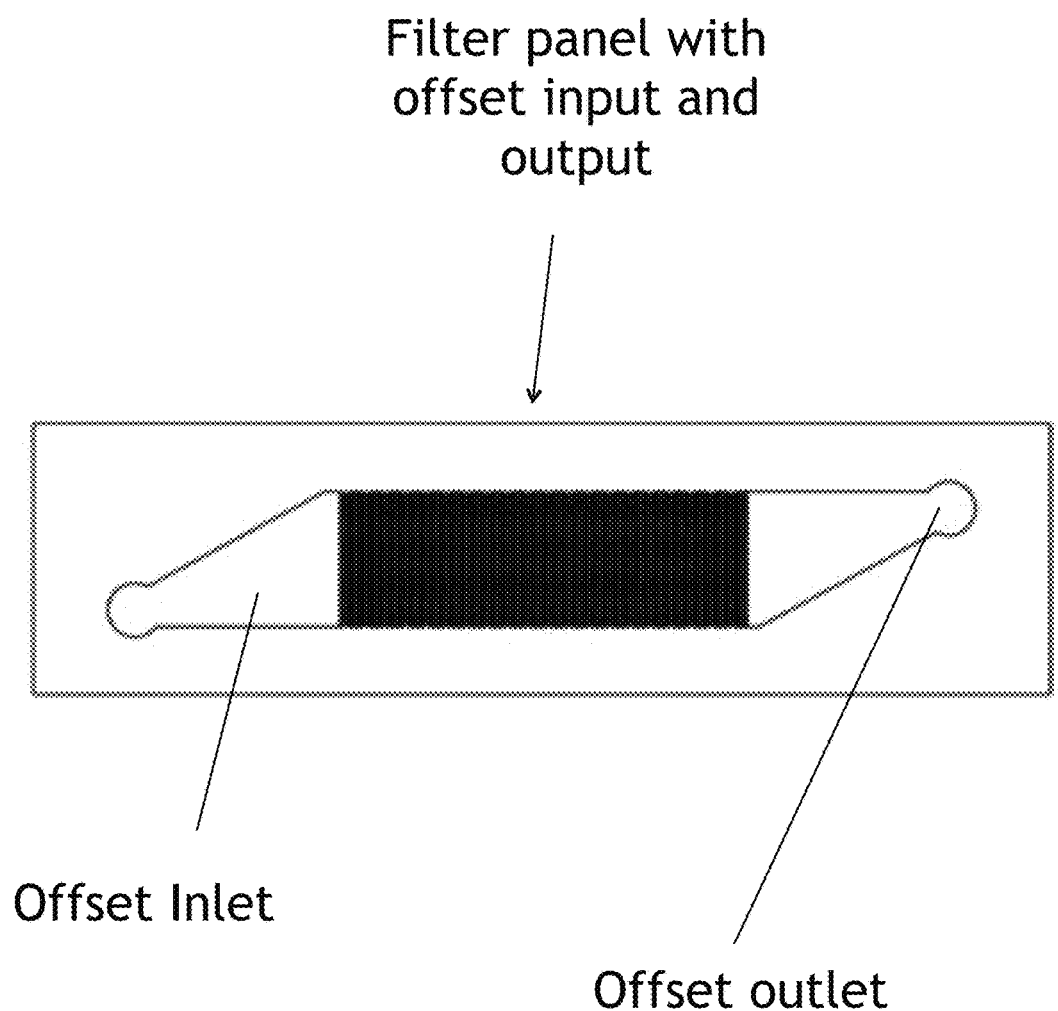
FIG. 19 is an isometric view of an alternate filter panel as shown in FIG. 18 with offset input and output.

Referring to FIG. 19, an alternate embodiment of the filter panel with vertically offset inlet and outlet areas is shown. This geometry yields flow paths that are more common in length than disclosed in previous Figs.

Figure 20:
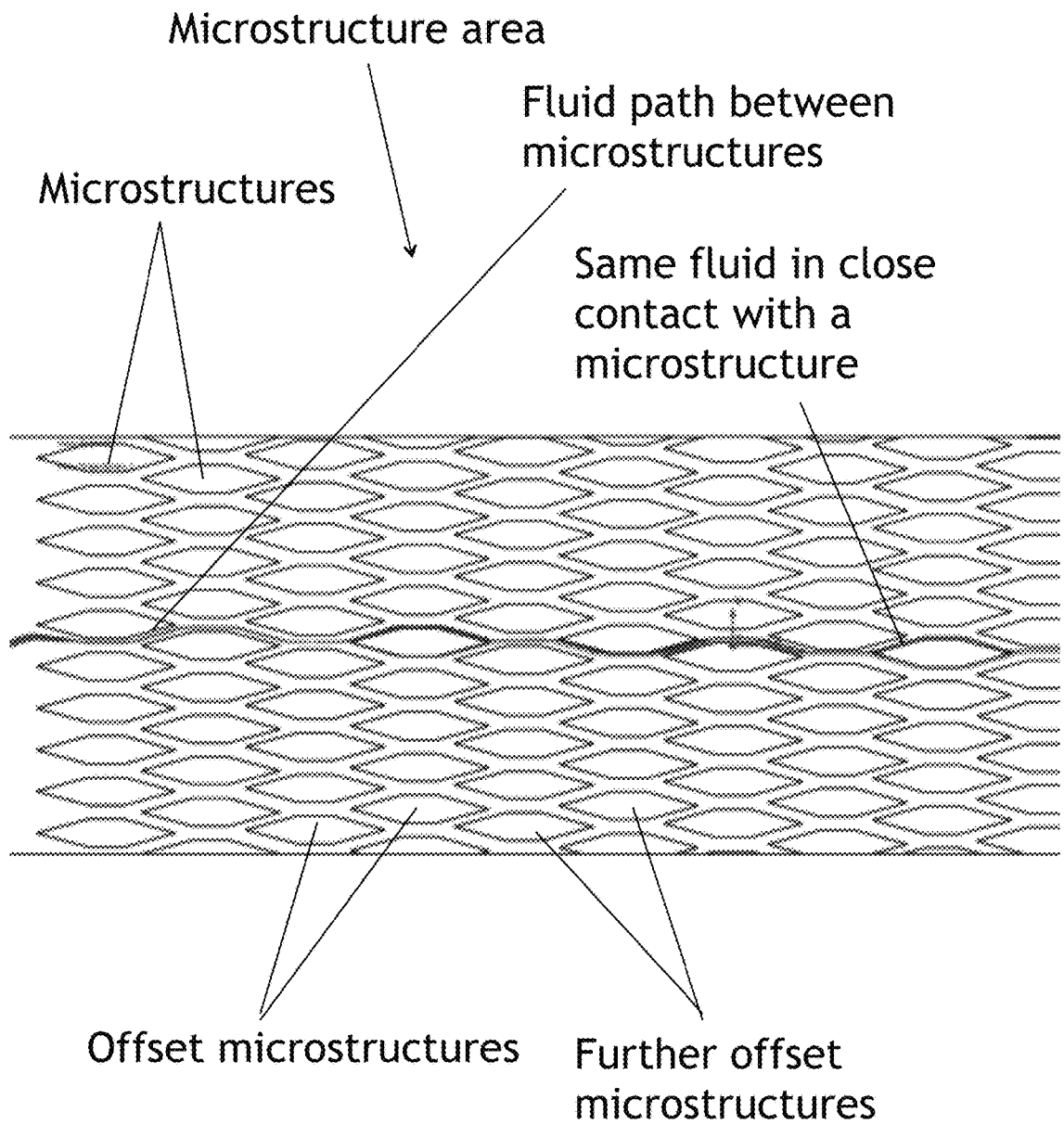
FIG. 20 is a close-up view of an alternate embodiment of the microstructure area of the filter panel shown in FIG. 4 that includes fluid flow lines.

Referring to FIG. 20, an alternate embodiment of the filter panel is shown with slight vertical offsets in the vertical height of the microstructures in the microstructure area. By slightly offsetting the height of the microstructures the tip of the microstructure cut through slightly different points in the flow path. Without the offset the same cross sections of flow would contact the surface of the microstructures over and over as the flow progresses through them.

The flow lines are only shown for one elevation of the fluid flow. Flow through a separation filter of this type would likely be one with a low Reynolds number. Low Reynolds number flows result in a laminar type boundary layer.

The first column cuts the flow stream at specific heights. These heights can accurately be located when the microstructures are fabricated directly from semiconductor type processes or if they are replicated from a tool made from semiconductor processes. The second column of microstructures cuts the flow field directly in the center of the flow between the microstructures in the first column.

The third column is off slightly vertically from the first column. The fluid cut by the third column of microstructures is cut slightly above the path cut by the first column of microstructures. One would want to design this vertical offset while considering the flow rate and attractive force between the particles or compound in the fluid and the surface of the microstructure.

Successive columns of microstructures would be offset by the same amount. With only a relatively small number of offset microstructures one could insure that all areas of the flow path pass within close proximity to the surface of a microstructure.

Figure 21:
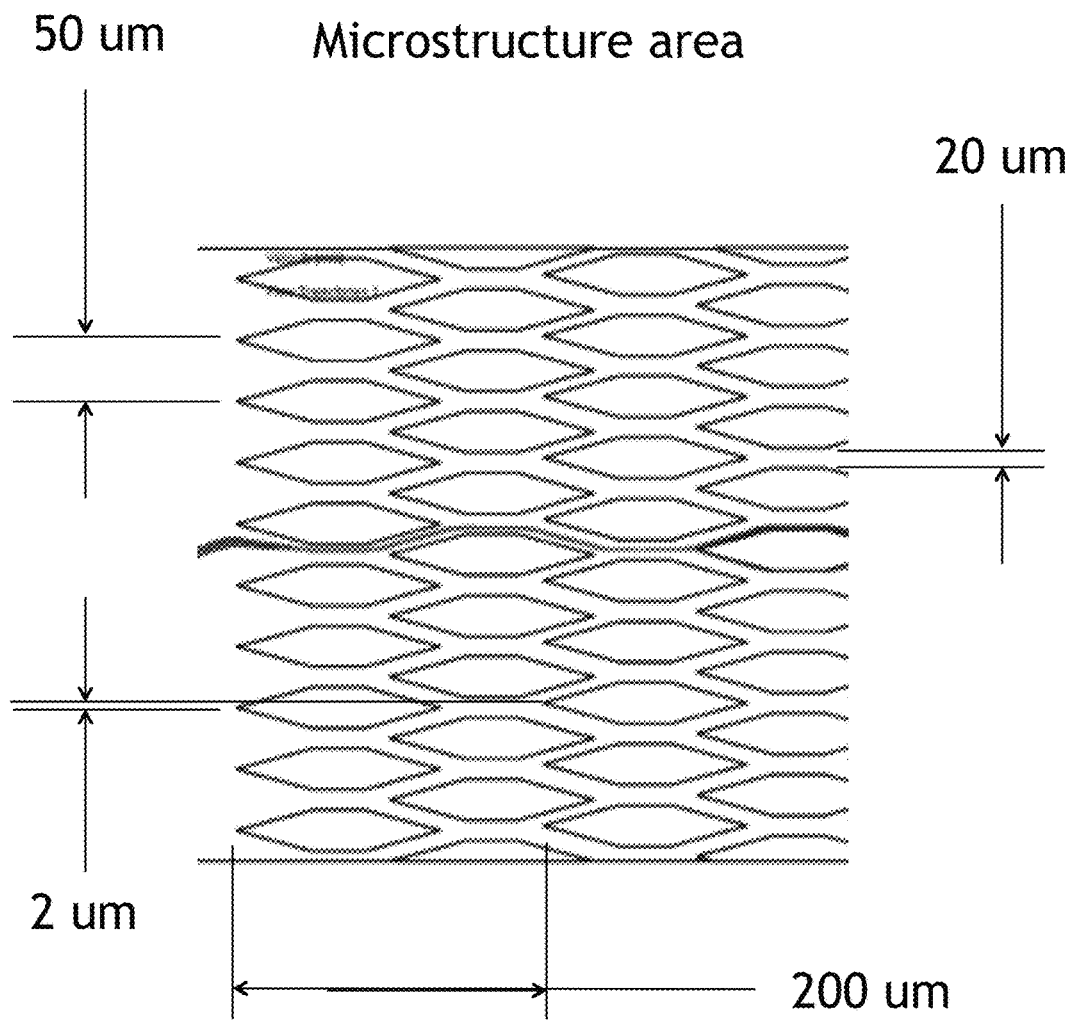
FIG. 21 is a close-up view of FIG. 20 with example dimensions.

Example dimensions of the embodiment shown in FIG. 20 are shown in FIG. 21. The design is shown with a 20 μm space between all of the microstructures. The third column of microstructures is offset vertically upwards from the first column of microstructures by 2 μm. Fluid flowing 2 μm above the center of the first column of microstructures would eventually be cut in half by the tip of a microstructure in the third column. Fluid flowing 4 μm above the center of the first column of microstructures would be cut in half by the tip of s microstructure in the fifth column of microstructures. To cut the fluid flow at every 2 μm interval it would require a total of 20 columns of microstructures. To cut the fluid flow at every 1 μm interval it would require twice as many columns of microstructures. By varying the offset of pairs of columns a system can be designed for efficient separation of particles or compounds from a fluid. It should be noted that for a column offset of 2 µm a particle is no more than 1 µm away from a surface. It would be less than 1 µm above or greater than 1 µm below the surface of a microstructure. It should be further noted that laminar flow of the fluid is required, if the flow was to become turbulent the alignment of cuts would be disturbed.

It should be noted that these values are given to describe the geometric advantages of 3D microstructure filter technology. Those knowledgeable in fluid chemistry would want to engineer the structure for the specific fluids, particles, microstructure surface materials and flow rates.

The microstructures shown are ones consistent with ones made with semiconductor processes or replicated from them. These manufacturing techniques consistently produce features of a depth of 10 times the width. Following this guideline the microstructures could be 300 um deep. The entire cross section of the flow field would then be 0.15 sq. mm. The length of the flow microstructures would only need to be 2 mm long for a cut interval of 2 µm. For a 1 µm cut interval the length would be 4 mm long. For a 4 mm length the total volume of the microstructure volume would be only 0.6 cubic mm or 0.6 µl. Because of this tiny volume only a small sample size is require. Further, because of the short path length, the pressure to move fluid through the microstructures would be relatively small. A further advantage is that all of the flow paths are equal in length and cross section. This common path length equates to consistent attraction of particles along the flow path. If it is desirable to have a greater amount of fluid filters panels could be laminated together as shown in FIG. 17.

Figure 22:
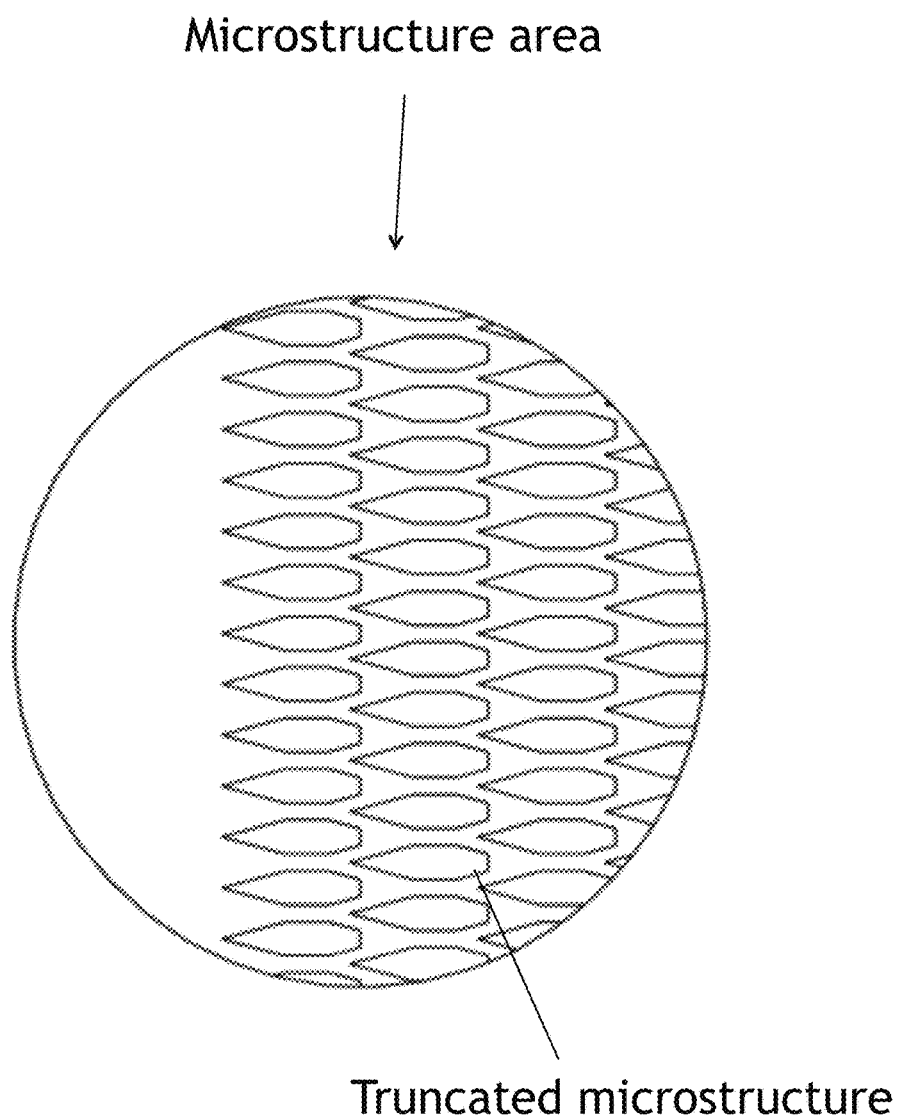
FIG. 22 is a close-up front view of an alternate embodiment of the microstructure area shown in FIG. 4.

Referring to FIG. 22 an alternate embodiment of the filter panel is shown with microstructures that are truncated at the trailing end. The truncation disrupts and generally mixes the flow to mix the flow vertically. Mixed flow increases the likelihood that all areas of the flow path will come in close proximity to the surface of at least one microstructure. This embodiment is less desirable that the previously described embodiment but would still produce reasonable performance.

The present technology is directed to separation, and more specifically, but not by way of limitation, to separation mechanisms that comprise multiple microstructures made from or coated with materials commonly used in separation. Some of these materials are mentioned in the prior art section. These separation microstructure panels are configured to maximize separation of the compounds within the fluid. The separation filter may be used in chromatography or reverse type chromatography.

Figure 23:
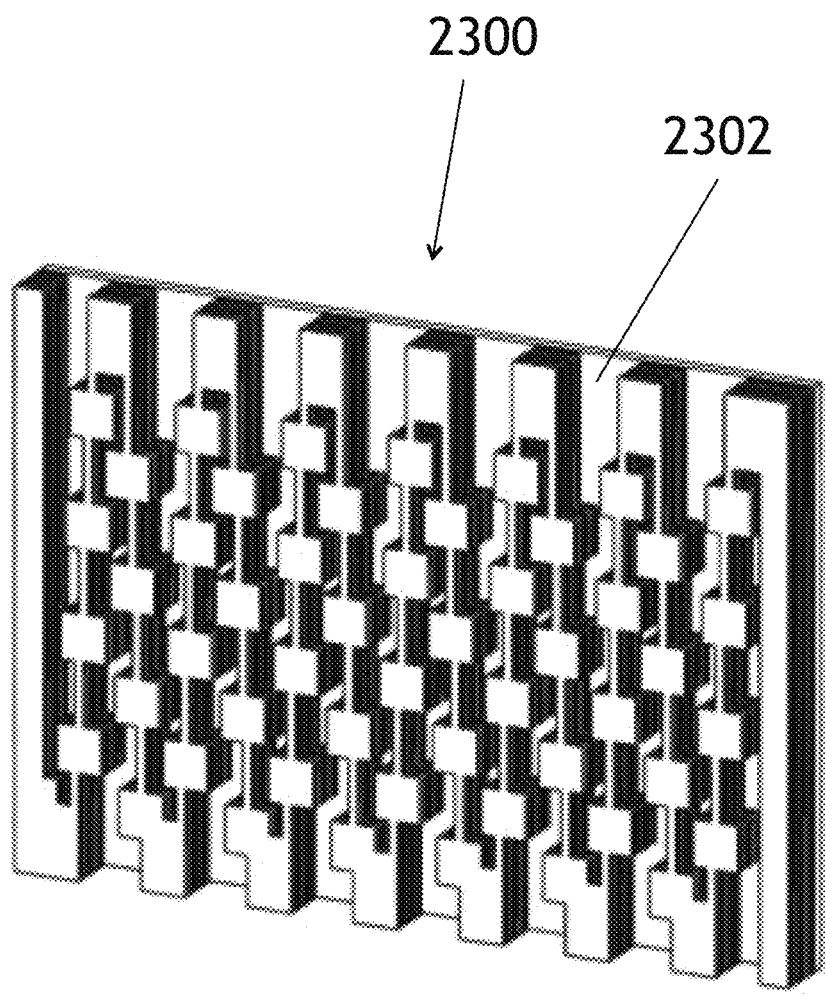
FIG. 23 is a perspective view of an example microstructure filter panel.
Figure 24:
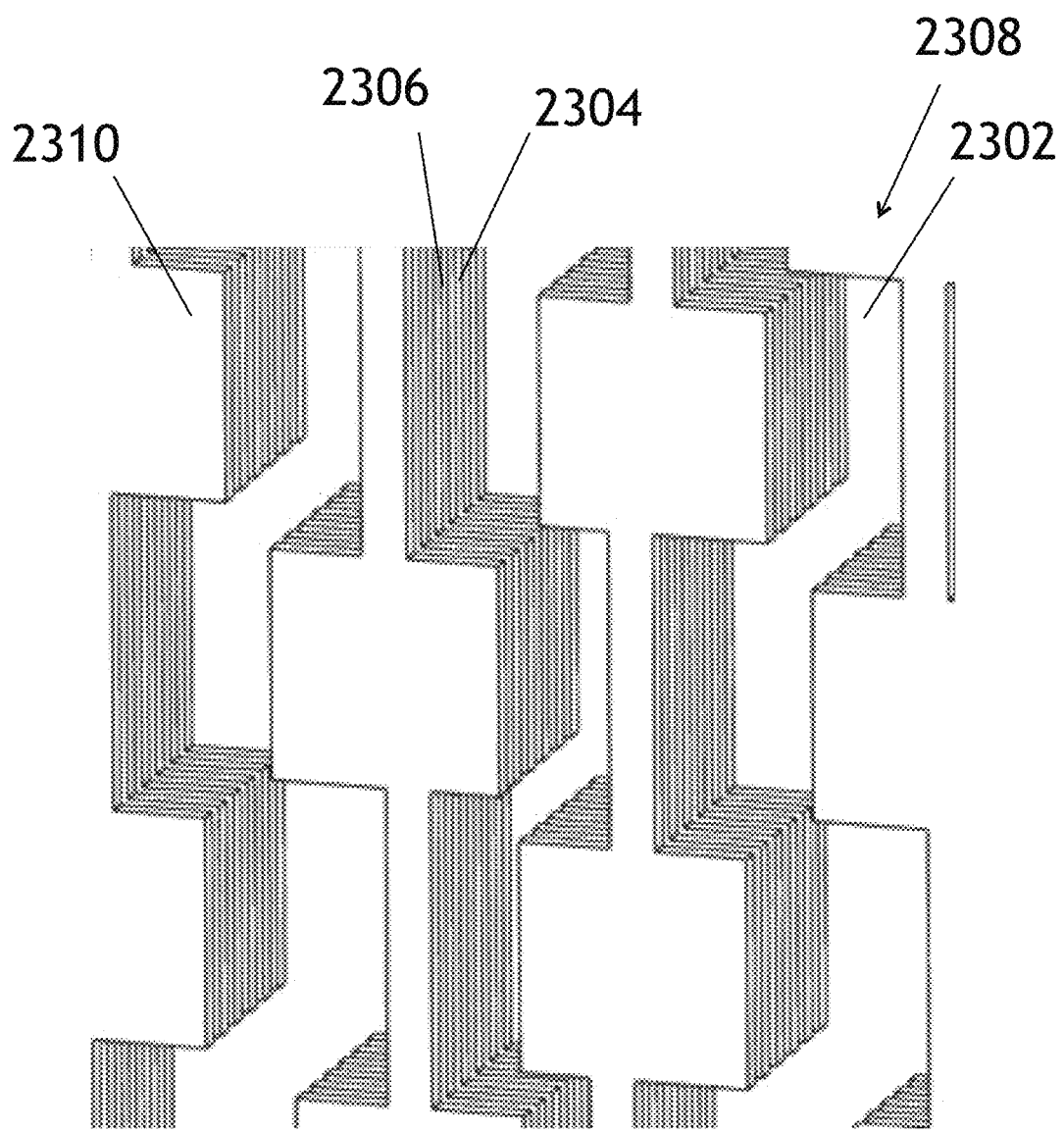
FIG. 24 is a close up perspective view of the microstructure filter panel of FIG. 23.
Figure 25:
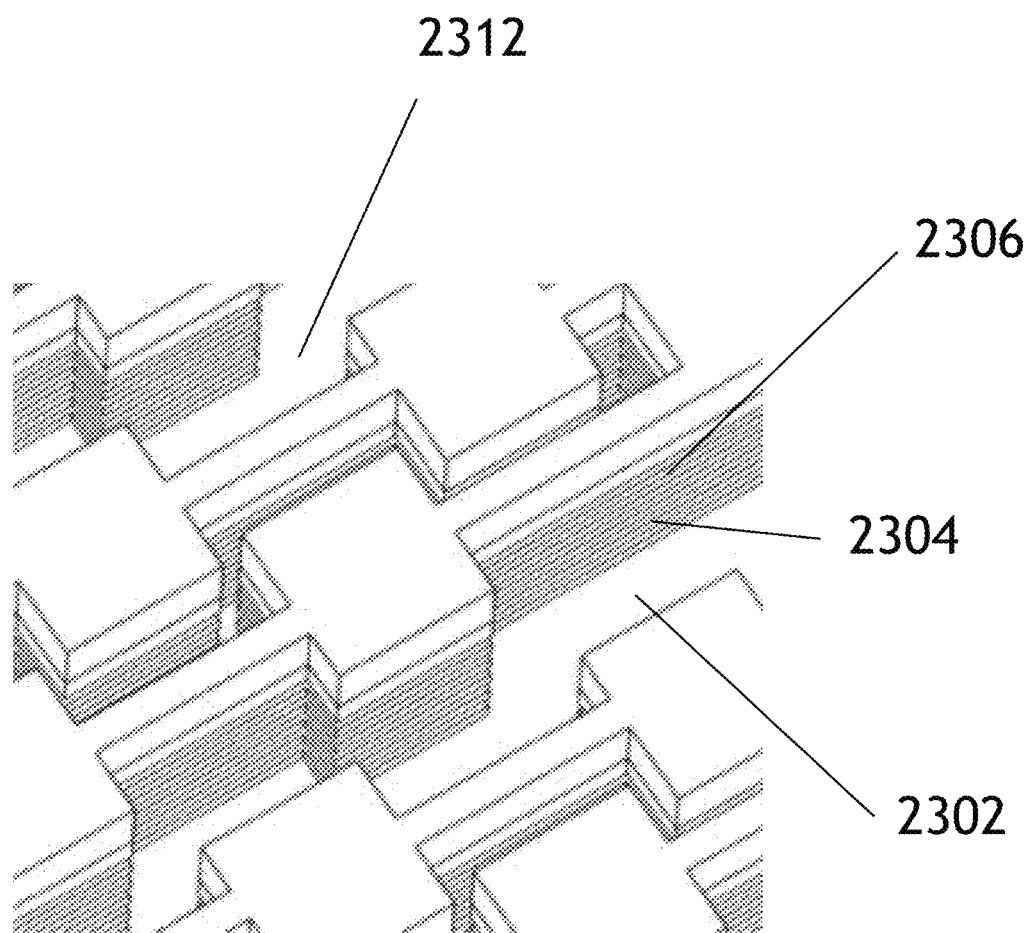
FIG. 25 is side perspective view of the microstructure filter panel of FIGS. 23-24.

FIG. 23 illustrates an example multilayer microstructure filter panel 2300. The panel 2300 is illustrated in greater detail in FIGS. 24 and 25. A close up view of a section of the panel 2300 is illustrated in FIG. 24 while a cross sectional view of a second of the filter panel 2300 is illustrated in FIG. 25. The panel 2300 is comprised of a base material 2302, also referred to as a wafer. A plurality of alternating structural and sacrificial layers (such as structural layer 2304 and sacrificial layer 2306) are disposed on the base material 2302. An example process for creating layered structures is described in greater detail above. Also, additional aspects of microstructure filter creation are found in applicant's co-pending U.S. patent application Ser. No. 14/701,528, filed on May 1, 2015, which is hereby incorporated by reference here in its entirety, including all references cited therein.

The alternating structural and sacrificial layers are etched to create input and output channels, such as input channel 2308 and output channel 2310. When portions of the sacrificial layers are removed openings (e.g., holes, slits, cuts, slots, etc.) between the input channel 2308 and output channel 2310 are created, which allow for cross flow of fluid therebetween. The size of the openings functions to remove particles from the fluid. In some embodiments, rather than having openings, the sacrificial material can be comprised of a porous material that filters the fluid.

In some embodiments, the panel 2300 comprises an outer layer 2312, which can comprise a photoresist layer. In one embodiment, each of the structural layers is approximately 75 nanometers in height, while each of the sacrificial layers is approximately 15 nanometers high. The outer layer 2312 can have a height of approximately 1.5 microns. As mentioned before, the sacrificial layers can be partially etched to create perforations or openings.

Figure 26:
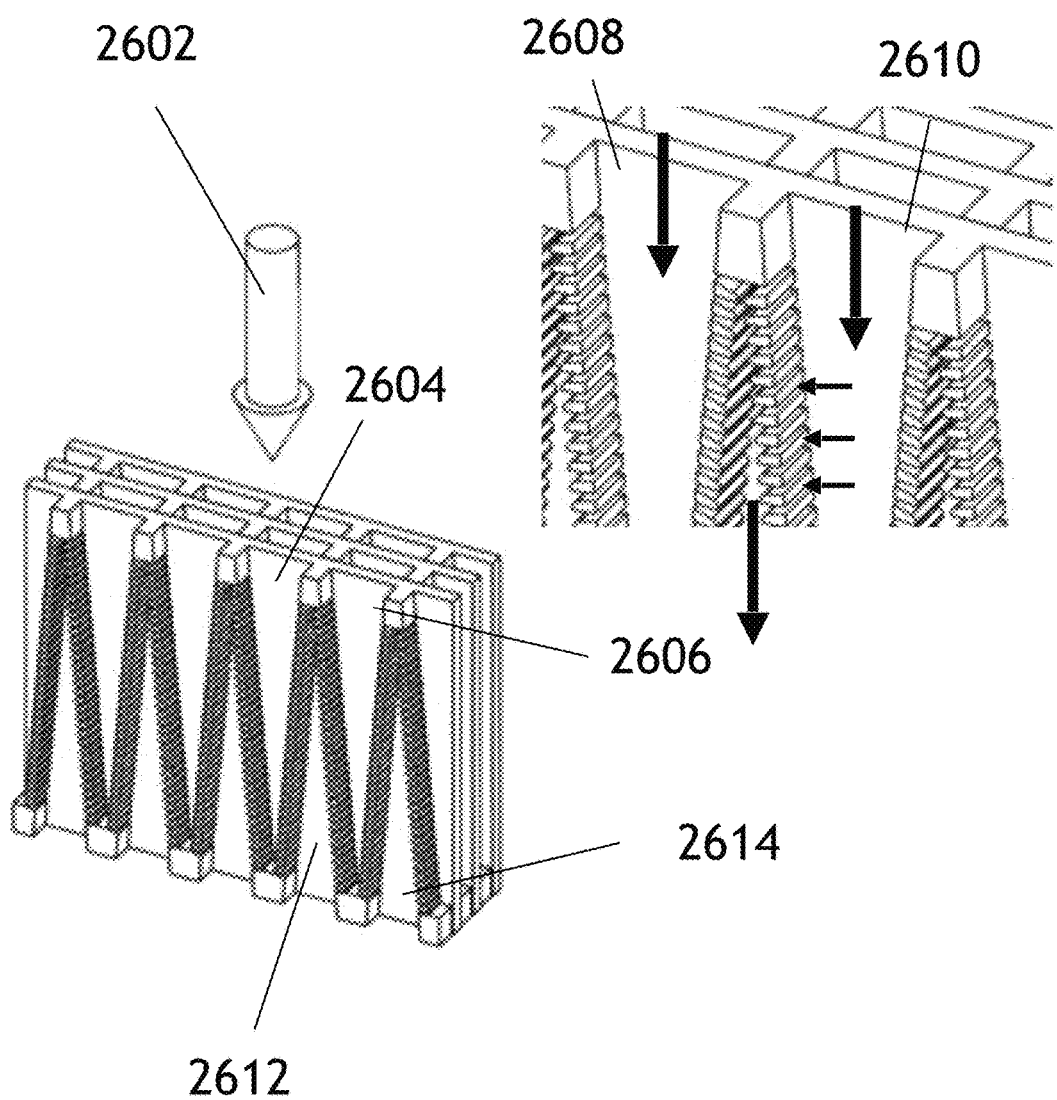
FIG. 26 is a perspective view of a plurality of microstructure filter panels in stacked configuration.

Referring to FIG. 26, which illustrates a plurality of multilayer microstructure filter panels stacked together. As illustrated, fluid 2602 enters the input channels, such as input channels 2604 and 2606, and passes through regions of cross channels 2608 and 2610 and ultimately out of output channels such as output channels 2612 and 2614.

To be sure, the multilayer microstructure filter panels and stacks of multilayer microstructure filter panels can be utilized to manufacture various filtering devices as well as chromatograph devices, as will be described in greater detail below.

Figure 27:
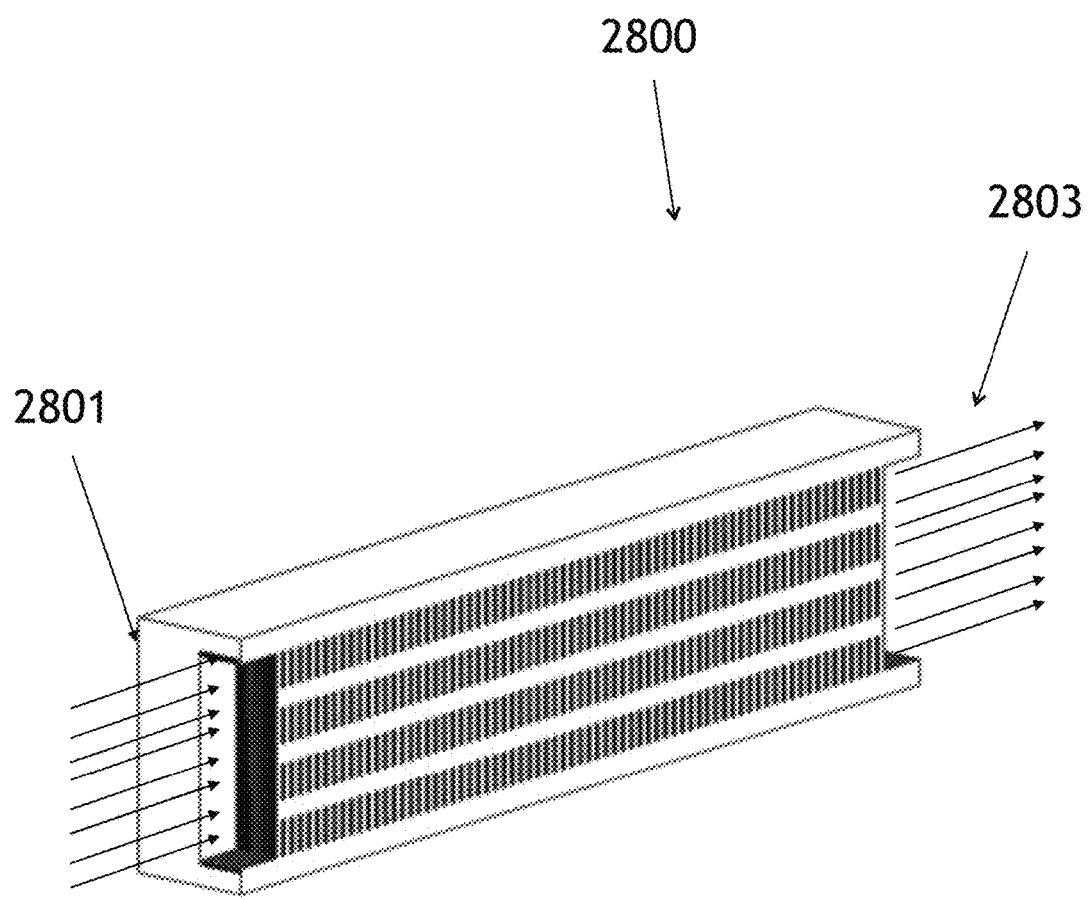
FIG. 27 is a perspective view of an example microstructure filter device for use in a chromatograph device.

FIG. 27 illustrates another example filter device 2800 constructed from a plurality of multilayer microstructure filter panels. The panel comprises a base housing 2802 that holds a plurality of multilayer microstructure filter panels. The base housing 2802 can be manufactured from a glass or silicon material, as well as from other materials that would be known to one of ordinary skill in the art with the present disclosure before them. The device 2800 is configured to filter a fluid 2801 entering one end of the device 2800 and exiting a terminal opposite end of the device 2800 exiting a terminal opposite end of the device 2800.

Figure 28:
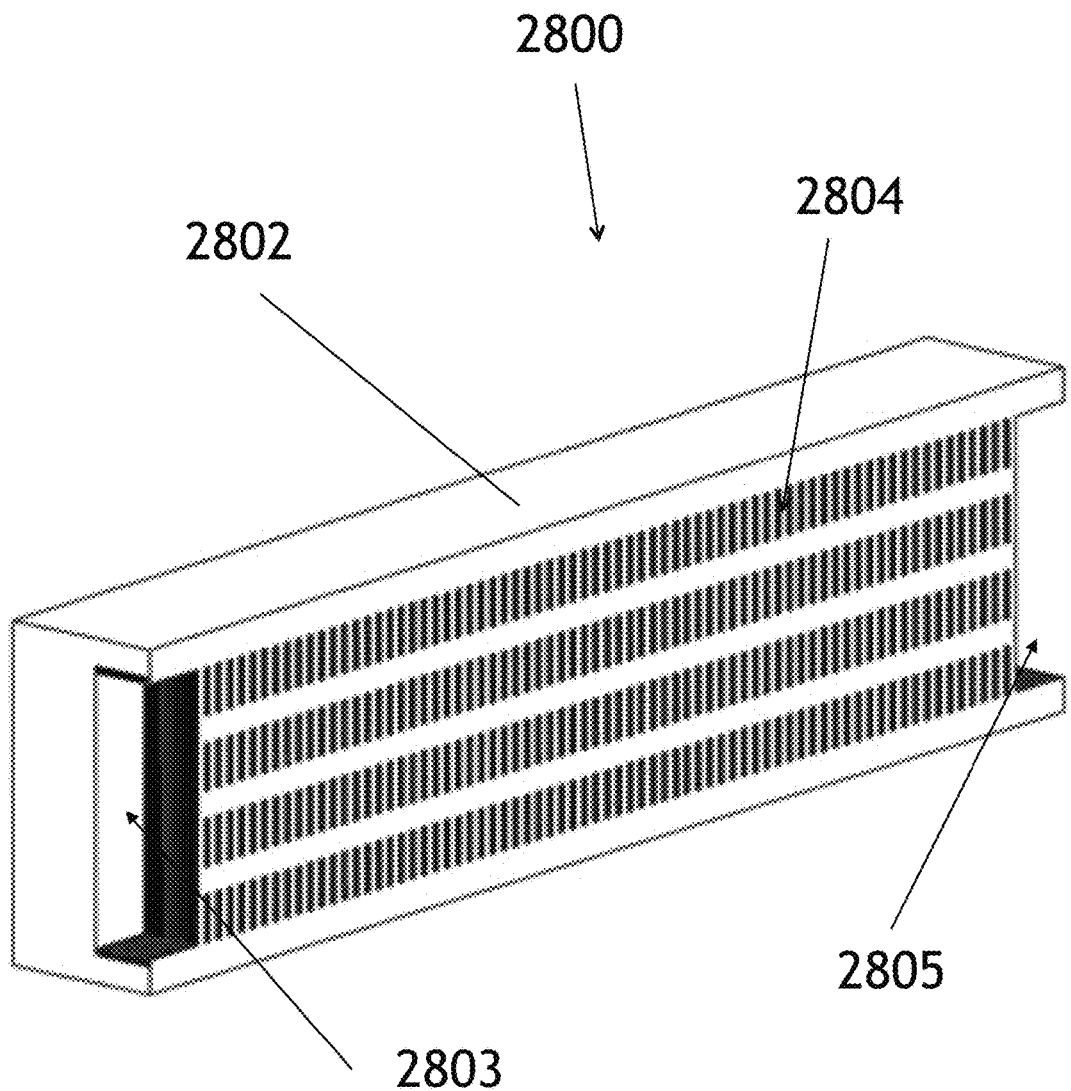
FIG. 28 is a cross section view of the example microstructure filter device of FIG. 27.

The details of the plurality of multilayer microstructure filter panels are illustrated in greater detail in FIGS. 27-32B. FIG. 28 is a cross sectional view of the filter device 2800 of FIG. 27. The microstructure filter panel 2804 comprises an inlet 2803 and an outlet 2805. The inlet and outlet can be created through etching or other similar processes.

Figure 29:
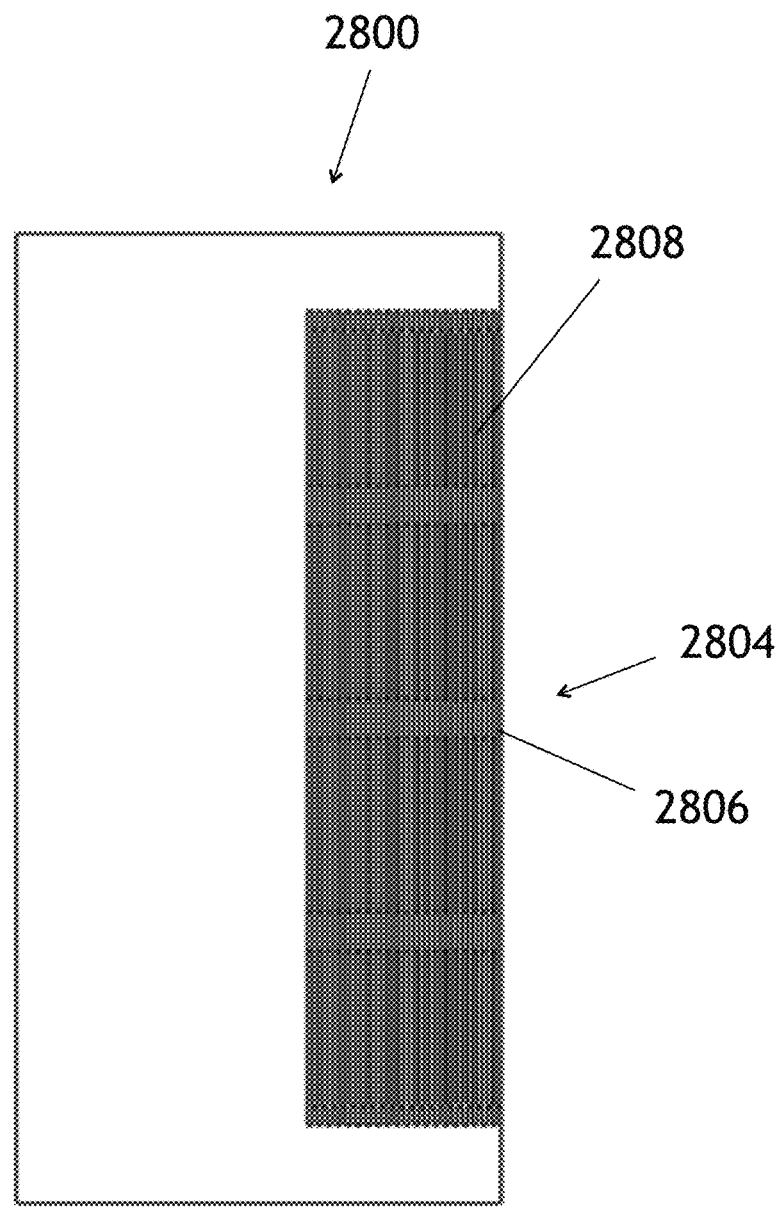
FIG. 29 is an end view of the microstructure filter device of FIG. 28.
Figure 30:
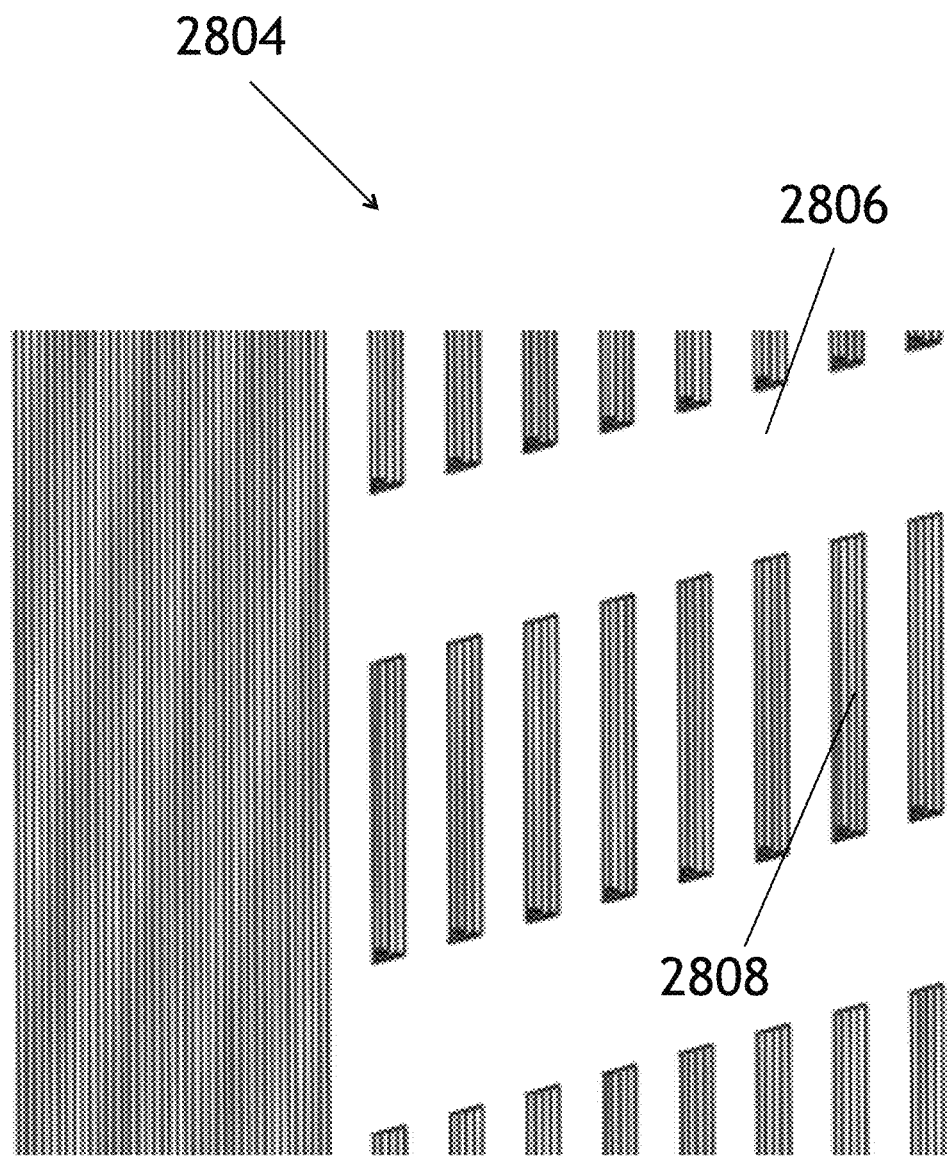
FIG. 30 is a perspective view of a microstructure filter.

FIG. 29 is an end view of the device 2800 illustrating a multilayer microstructure filter panel 2804 nested within the base housing 2802. FIG. 30 illustrates various spacer layers (structural layers), such as structural layer 2806. A series of structural and sacrificial layers comprise the microstructure filter panel 2804. In one embodiment, the microstructure filter panel 2804 is etched to expose a plurality of layered sections, such as layered section 2808.

Figure 31:
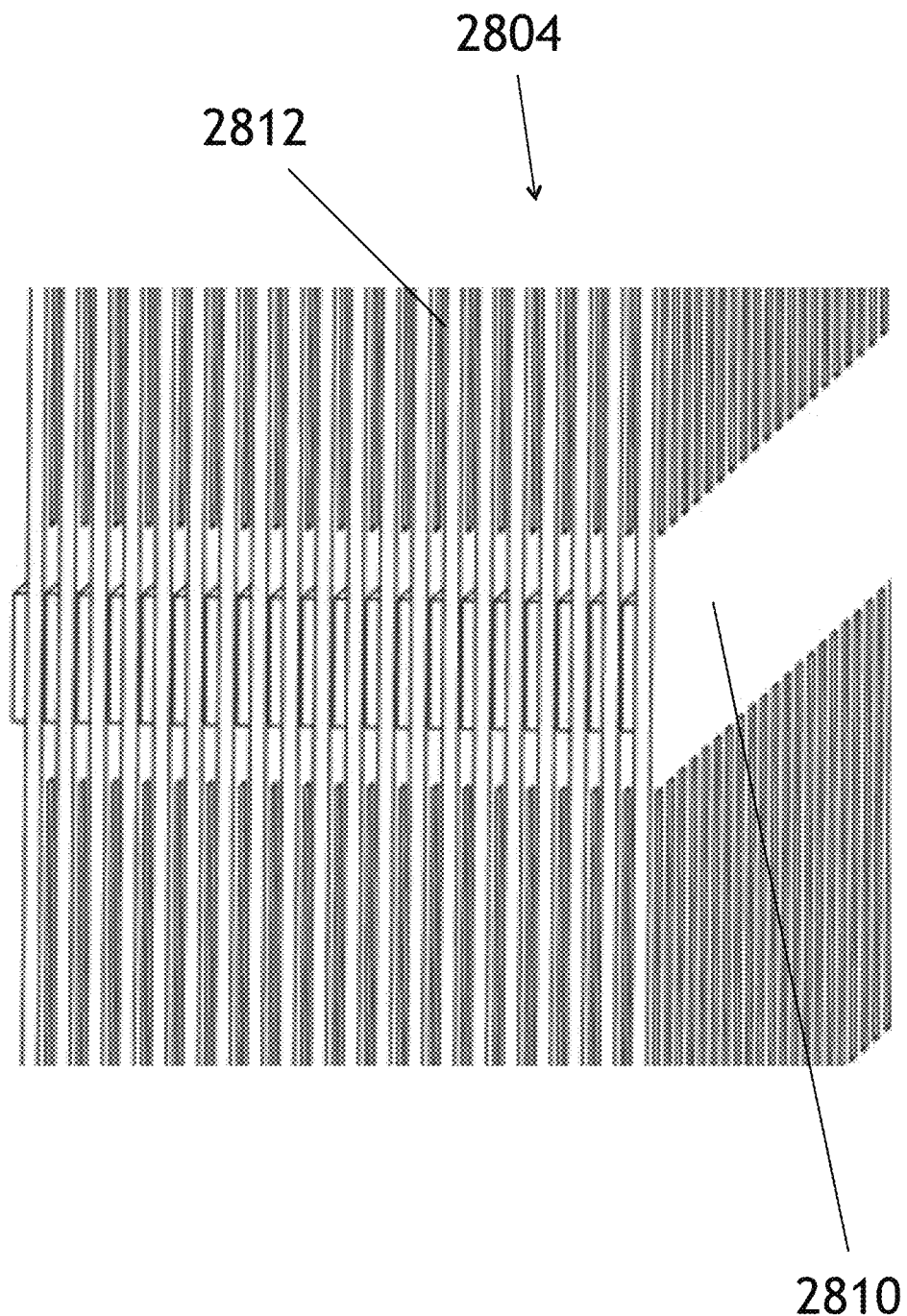
FIG. 31 is another perspective of the microstructure filter.

FIG. 31 is a close up perspective view of a structure layer section of the microstructure filter panel 2804. The structure layer section illustrates various layers of structural layers, such as structural layer 2810 and sacrificial layer 2812. A series of spacers such as spacer 2810 can be comprised of sacrificial material.

Figure 32A:
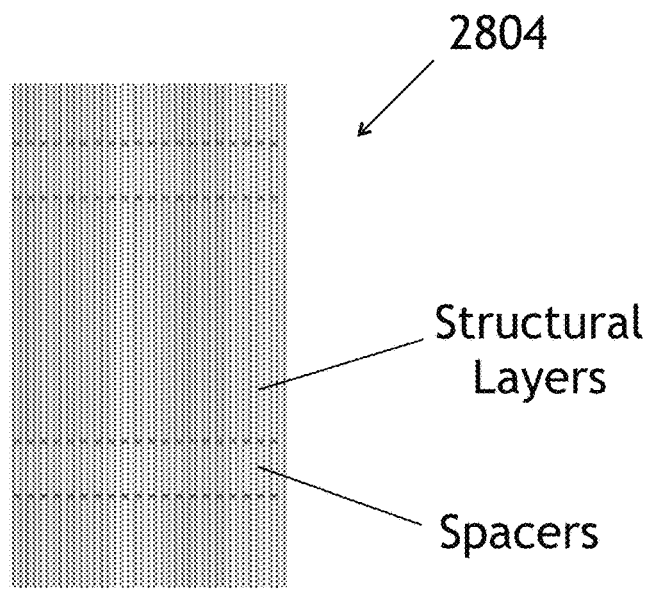
FIGS. 32A and 32B collectively illustrate spacers and openings of layers of the microstructure filter.
Figure 32B:
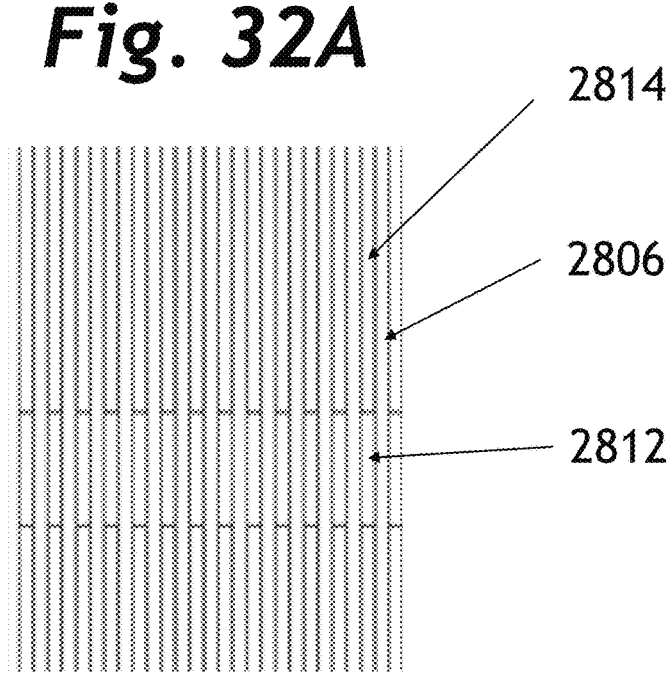

FIGS. 32A and 32B collectively illustrate additional perspective views of the microstructure filter panel 2804 showing the layering and openings created within the microstructure filter panel 2804. The microstructure filter panel 2804 is illustrated with spacers of sacrificial material 2812, structural layers 2806, and sacrificial layer sections which are partially removed (or entirely) to create openings 2814 through which fluid can flow.

Figure 33:
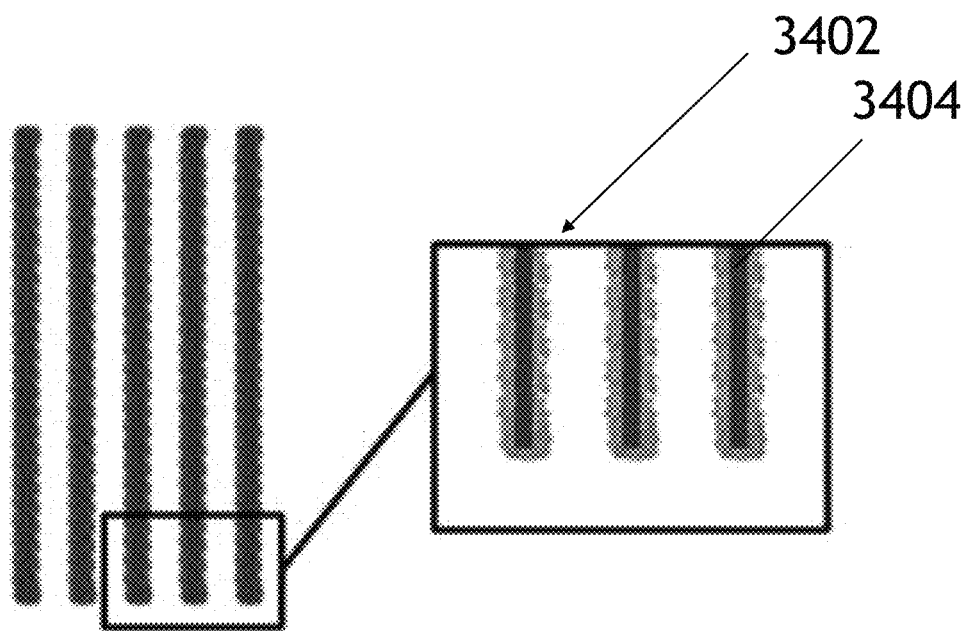
FIG. 33 illustrates nanoscale coatings applied to filter features of a microstructure filter device.

In some embodiments, an effective surface area or fluidic surface area of the microstructure filter panels, such as the cross channels can be increased by creating nanoscale structures or other texturing on the surfaces. For example, FIG. 33 is a close up view of a cross channel section 3402 which is provided with a nanoscale coating 3404. The nanoscale coating 3404 can be created through a depositing process or by etching away of sacrificial material.

It will be understood that one of ordinary skill in the art with the present disclosure before them would be capable of using other conventional coating processes for creating three dimensional features on the surfaces of the microstructure filter panels.

The three dimensional nature of the microstructure filter panels, whether including nanoscale cladding or not, provides a five-fold increase in particulate attraction forces compared with filter devices of lower dimensions.

Figure 34:
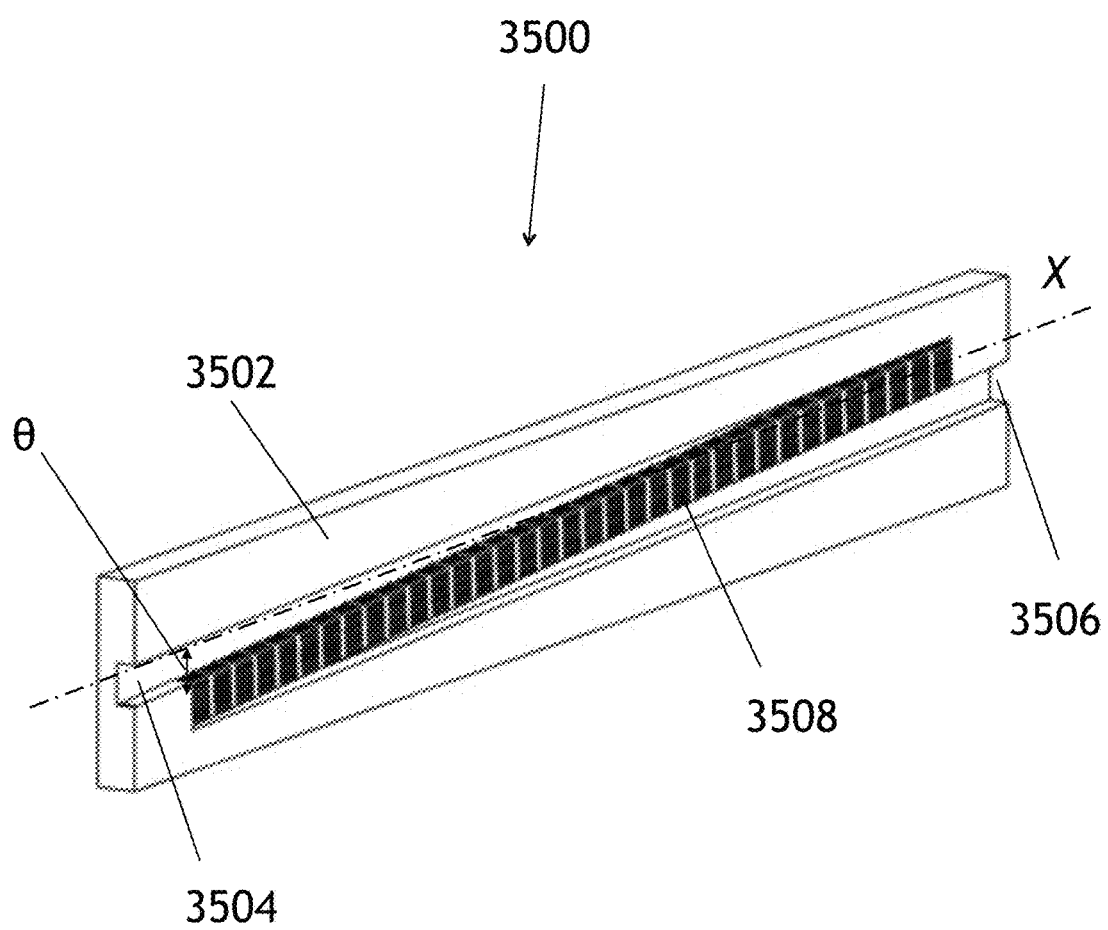
FIG. 34 is another example microstructure filter device.
Figure 35:
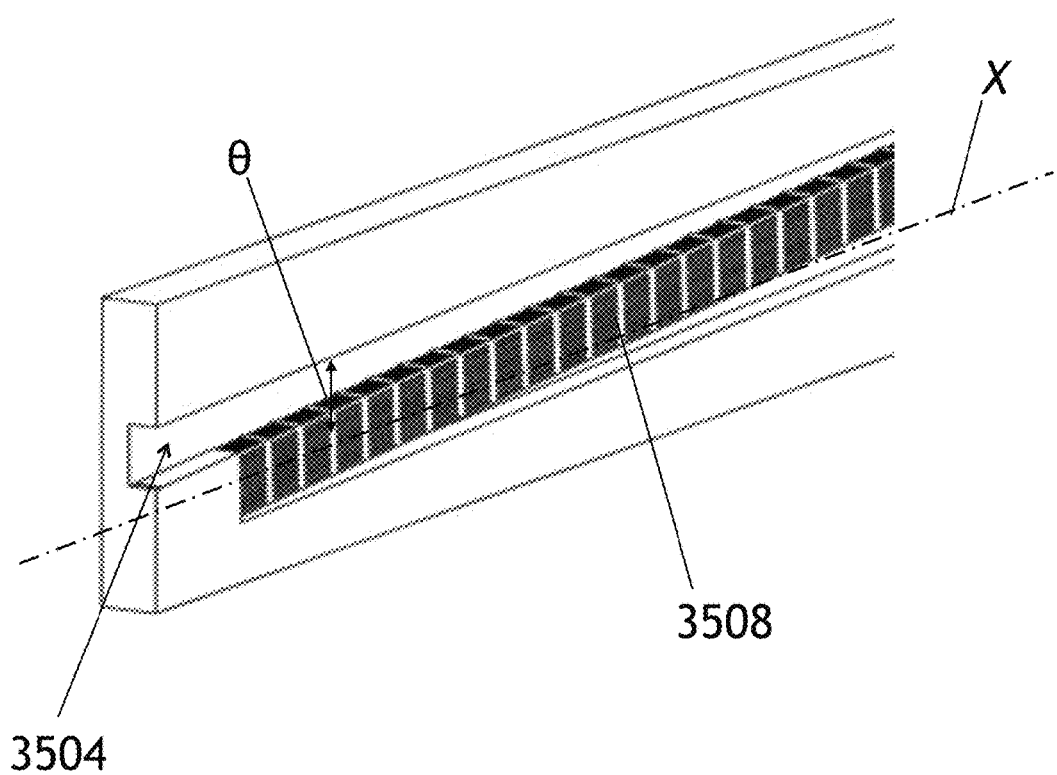
FIG. 35 is a close up view of a first end of the microstructure filter device of FIG. 34.

FIG. 34 illustrates another example filter device 3500. The device 3500 also comprises a base housing 3502 that can be manufactured from a glass or silicon material, as well as from other materials that would be known to one of ordinary skill in the art with the present disclosure before them. The base housing 3502 is configured with an inlet notch 3504 (a close view illustrated in FIG. 35) and an outlet notch 3506. In some embodiments, a portion of the inlet notch 3504 is angled relative to a reference line X. In some embodiments, a portion of the outlet notch 3506 is also angled relative to the reference line X. In one embodiment the inlet notch 3504 angles upwardly as it extends from a first end of the base housing 3502 and the outlet notch 3506 angles from a narrow portion to a second end of the base housing 3502 that is opposite the first end.

A plurality of multilayer microstructure filter panels is combined to create a microstructure filter 3508 is disposed at an angle θ relative to the reference line X. The filter panel 3508 extends between the inlet notch 3504 and the outlet notch 3506.

Fluid will enter the inlet notch 3504 and be dispersed into the microstructure filter 3508. The fluid passes through the microstructure filter panel 3508 into the outlet notch 3506. To be sure, fluid can enter the microstructure filter 3508 along the length of the inlet notch 3504 and exit the microstructure filter 3508 along the length of the outlet notch 3506.

Figure 36:
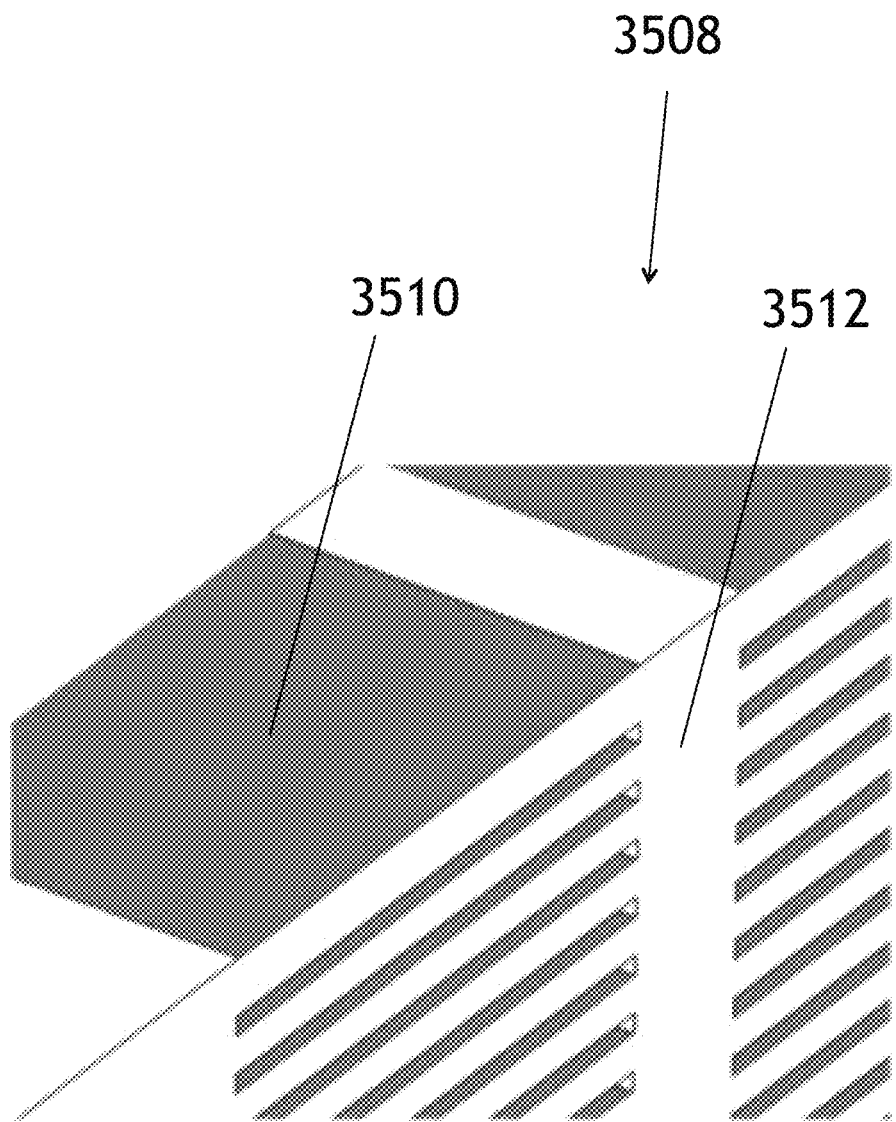
FIG. 36 is an even closer view of the microstructure filter of the microstructure filter device of FIG. 34.

FIG. 36 illustrates a close view of a portion of the microstructure filter 3508. A plurality of layered sections, such as layered section 3510 is illustrated, as well as a plurality of structure/support sections 3512. Again, the layered sections can be comprised of layers of structural and sacrificial materials.

Figure 37:
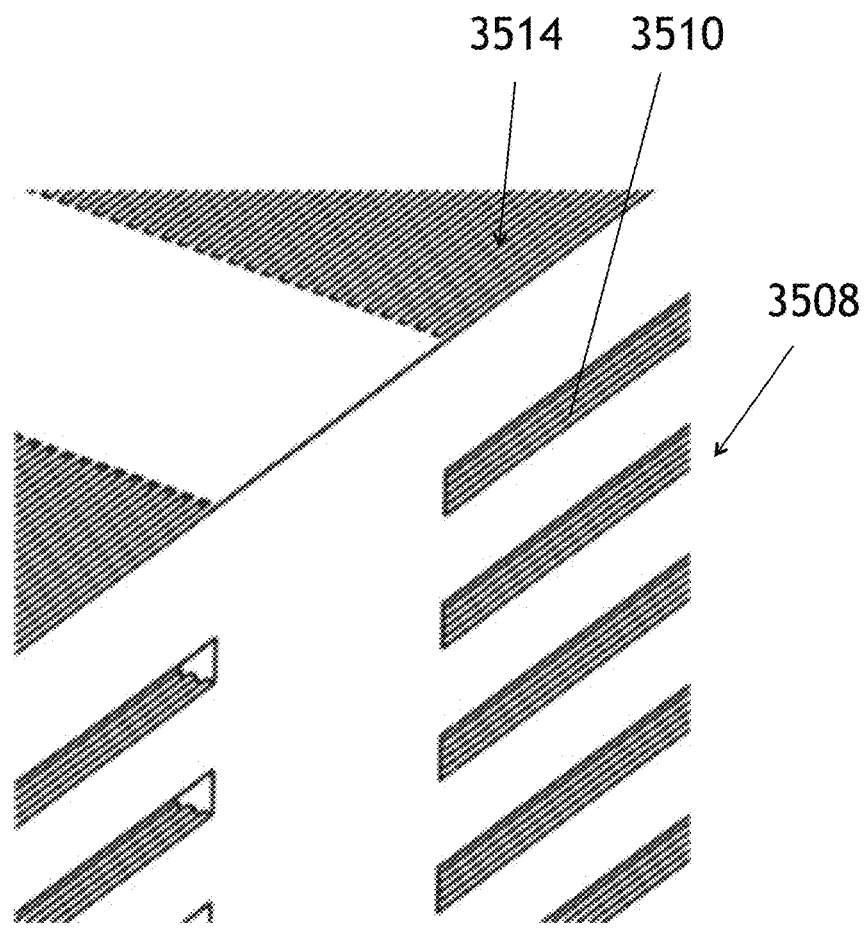
FIG. 37 is yet a closer view of FIG. 36.

FIG. 37 illustrates an even closer view of portion of the microstructure filter 3508 presented in FIG. 36. The layered section 3510 is comprised of a series of channels and sidewalls 3514 that filter the fluid as it passes through the microstructure filter 3508. Each of the layers can comprise channels and sidewalls of different thicknesses. For example, channels and sidewalls disposed near the inlet notch 3504 can be sized to attract particles larger than the particles attract by the channels and sidewalls proximate the outlet notch 3506 (FIG. 34).

Figure 38:
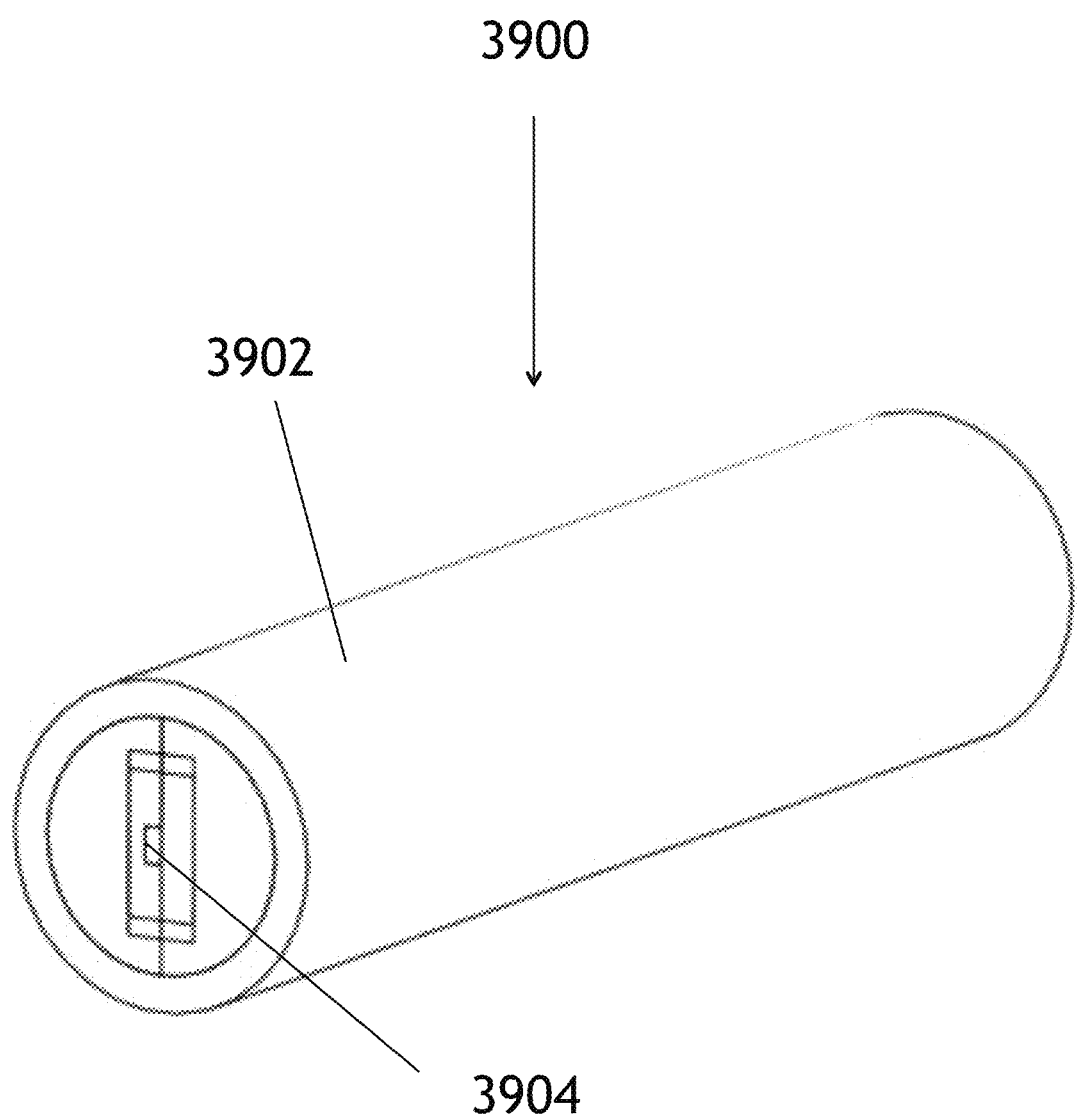
FIG. 38 is a perspective view of an example microstructure filter device in a tubular configuration.

FIG. 38 is an example filtering device 3900 that is constructed in accordance with the present technology. The filtering device 3900 includes a tubular housing 3902 that comprises an input port 3904 and an output port (not shown), which is identical to the input port 3904 but disposed on an opposing end of the filtering device 3900.

Figure 39:
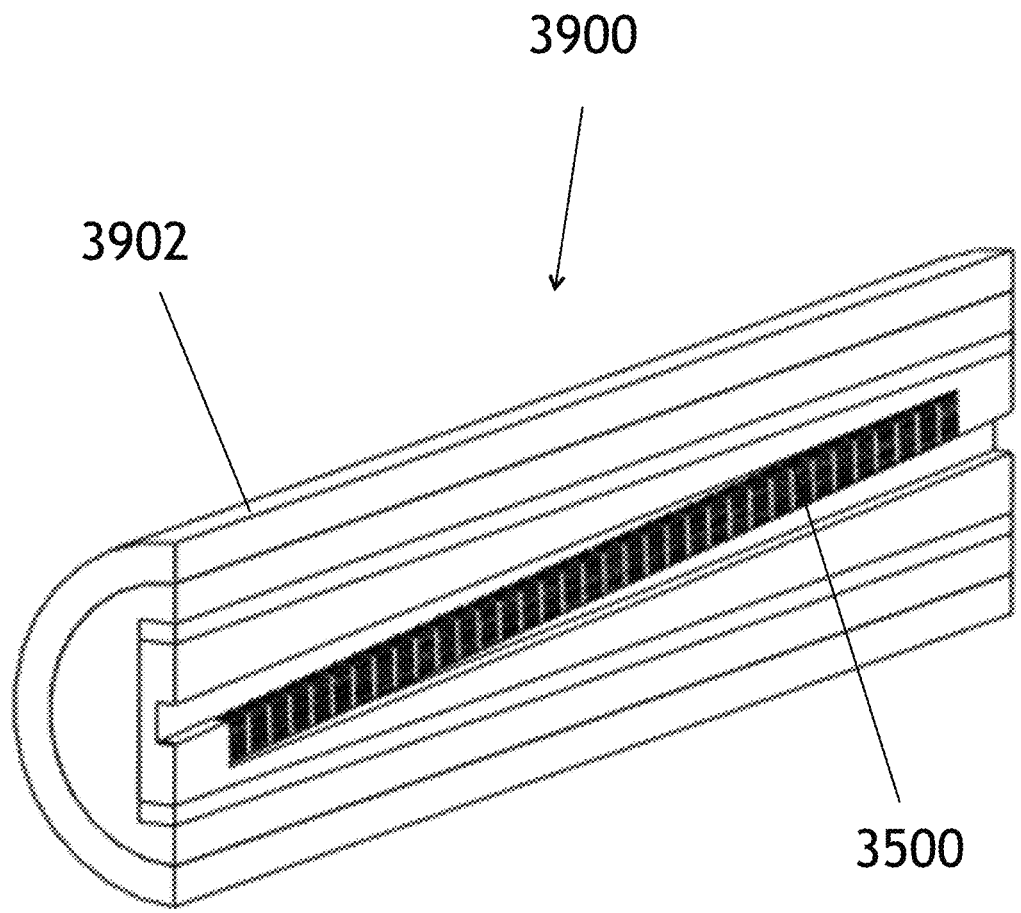
FIG. 39 illustrates the microstructure filter device of FIG. 38 in a cutaway view.

FIG. 39 illustrates that the example filter device 3500 of FIGS. 34-37 is utilized in the filtering device 3900. That is, the housing 3902 is configured to receive the example filter device 3500. The filter device 3500 can be used to filter any fluid for any number of applications.

Figure 40:
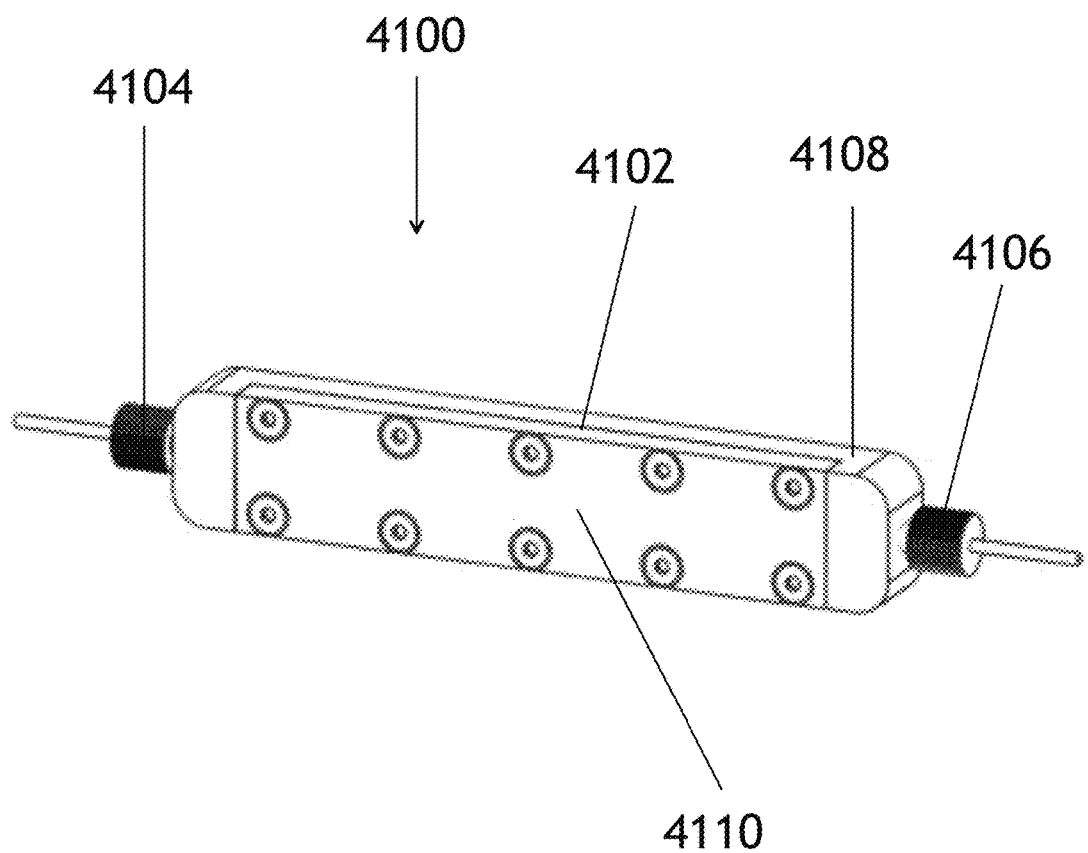
FIG. 40 is a perspective view of an example chromatograph device.
Figure 41:
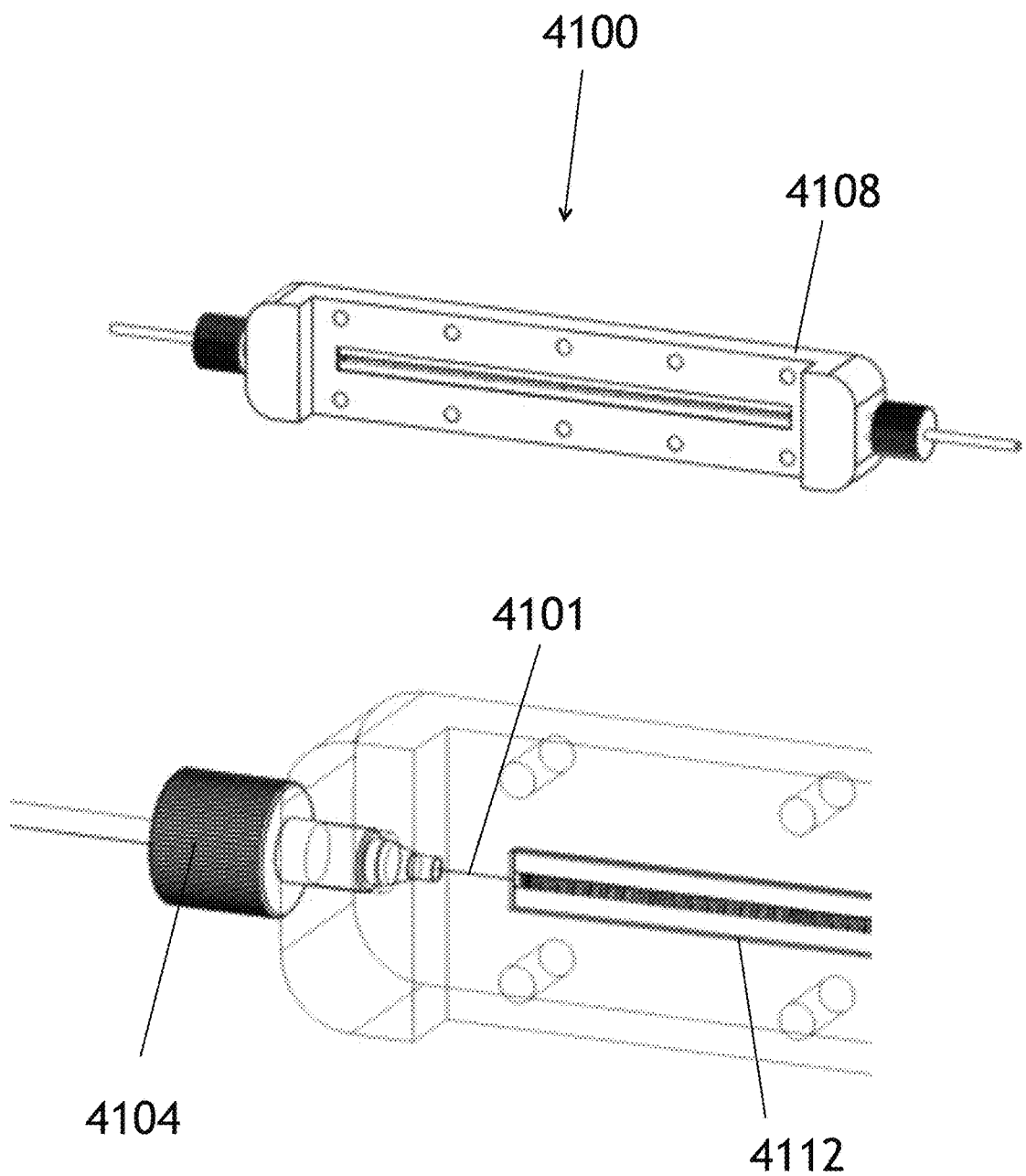
FIG. 41 is an exploded view of the chromatograph device illustrating a microstructure filter.

FIG. 40 illustrates an exemplary filter device 4100 in the form of a testing column. The device 4100 comprises a housing 4102 having fittings 4104 and 4106. In some embodiments, the housing 4102 is separable into a first section 4108 and a second section 4110 as illustrated in FIG. 41. The device 4100 comprises a microstructure filter 4112. The second section 4110 operates as a cover that bounds the uppermost (or outermost) layer of the microstructure filter 4112, ensuring that fluid transits through the microstructure filter 4112. An input tube 4101 transmits fluid from the fitting 4104 to the microstructure filter 4112.

Figure 42:
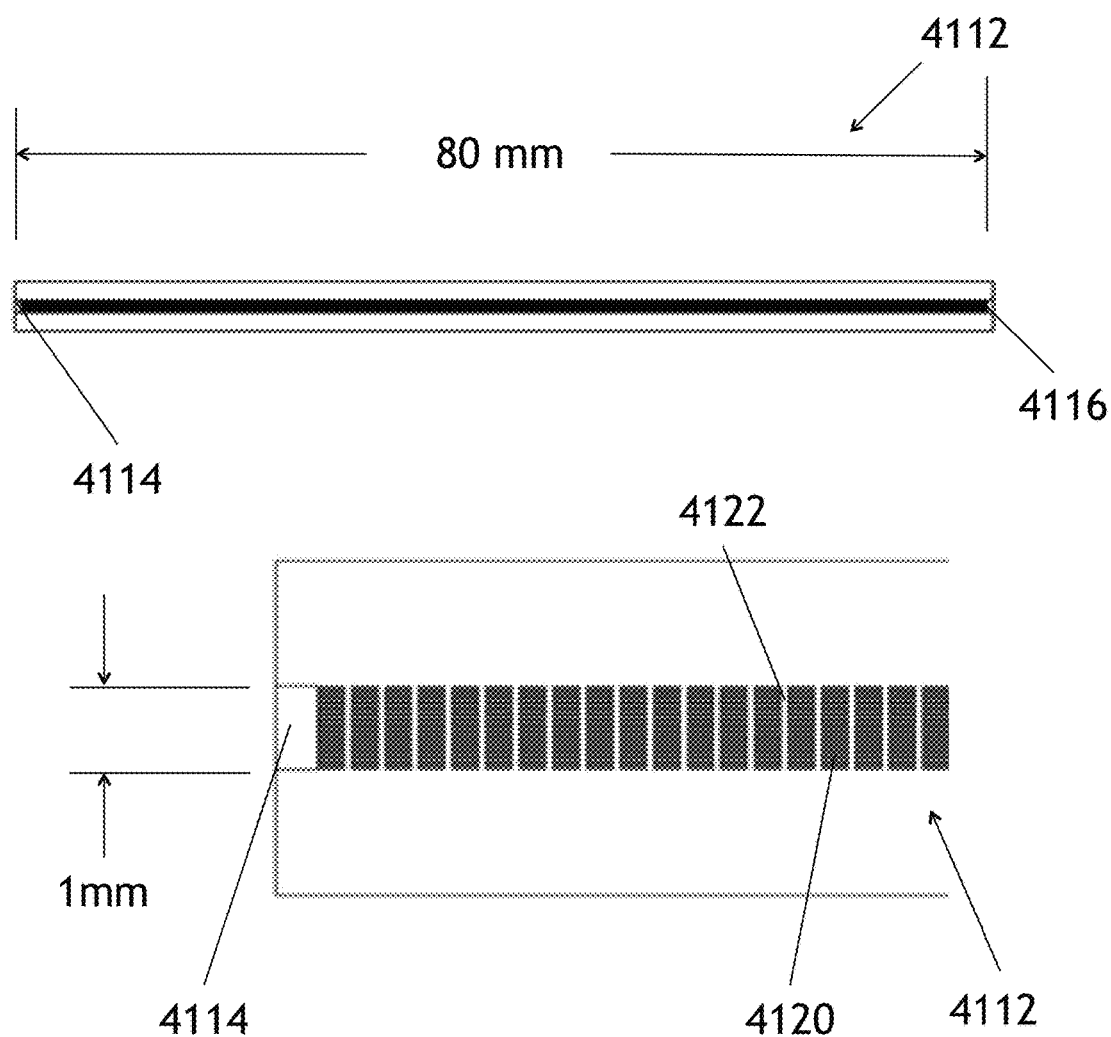
FIG. 42 is a view of a portion of the microstructure filter of the device of FIG. 40.
Figure 43:
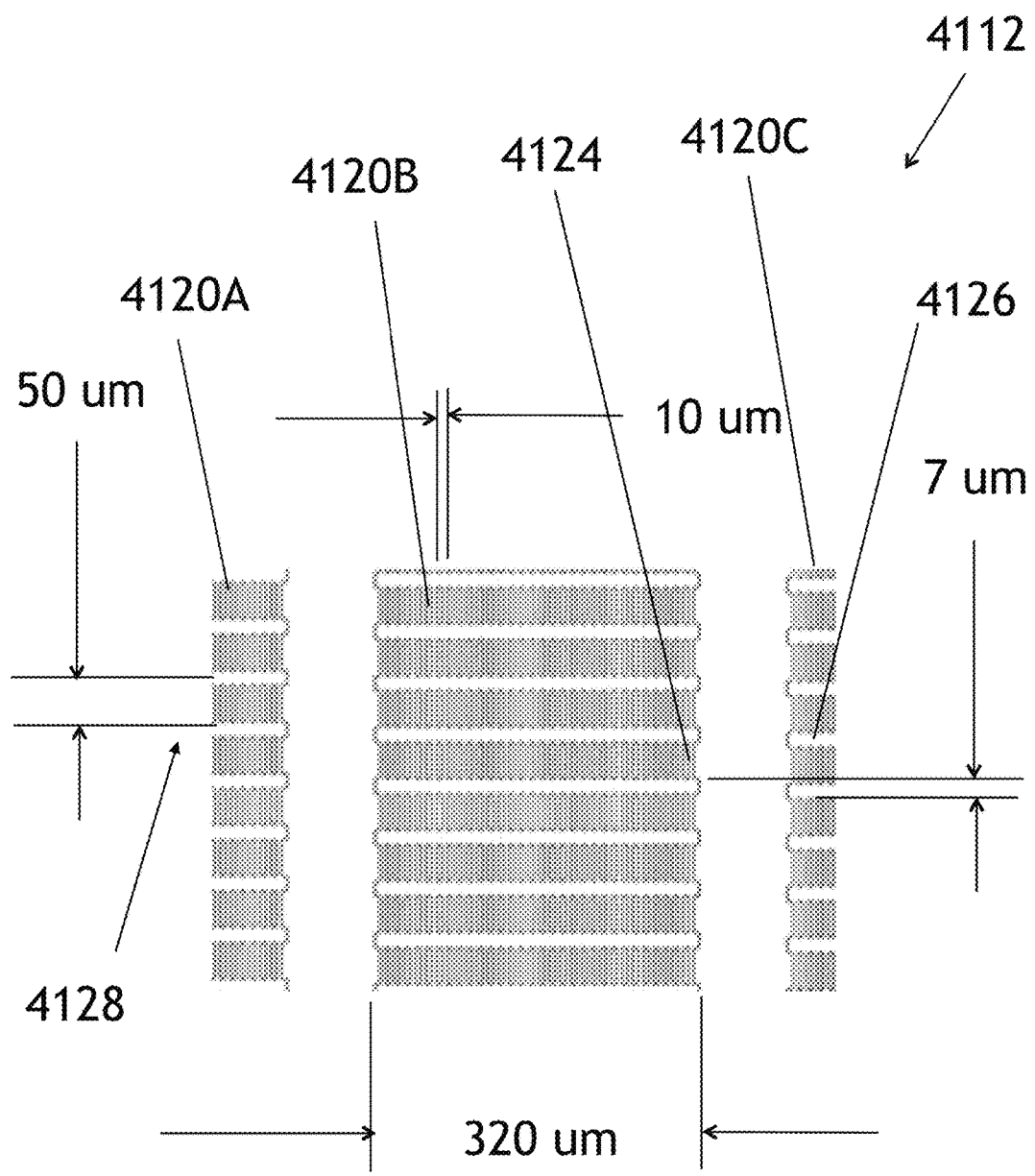
FIG. 43 is a closer view of the microstructure filter of FIG. 42.

FIG. 42 illustrates the microstructure filter 4112 in more detail. The microstructure filter 4112 comprises an inlet 4114 and outlet 4116. In some embodiments, the inlet and outlet are each approximately one millimeter wide. The microstructure filter 4112 has layered sections 4120 and support sections 4122. The microstructure filter 4112 is illustrated in FIG. 43 as having a plurality of layered sections 4120A, 4120B, and 4120C that are slightly offset from one another. For example, structural features 4124 of layered section 4120B are positioned slightly higher than structural features 4126 of layered section 4120C. Cross channels such as cross channels 4128 have a height that is approximately 50 micrometers and the width of the layered sections are approximately 32 micrometers. In some embodiments, a pitch between individual cross channel features is ten micrometers.

Figure 44A:
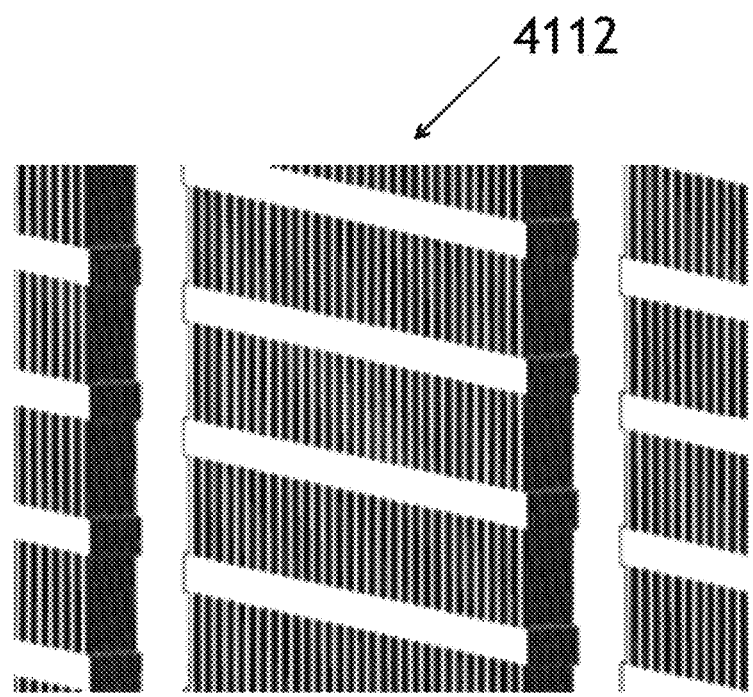
FIGS. 44A and 44B illustrate additional perspective views of the microstructure filter.
Figure 44B:
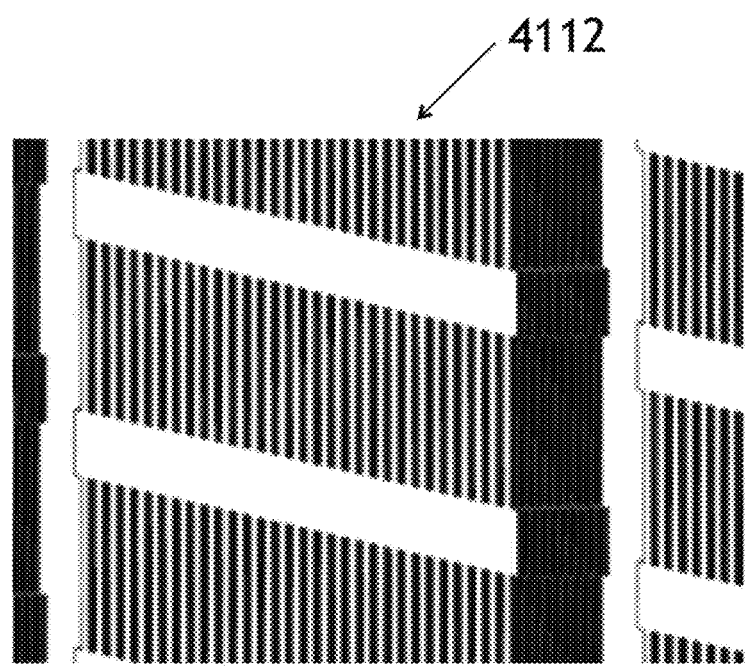

FIGS. 44A and 44B are close up views of the microstructure filter 4112.

Figure 45:
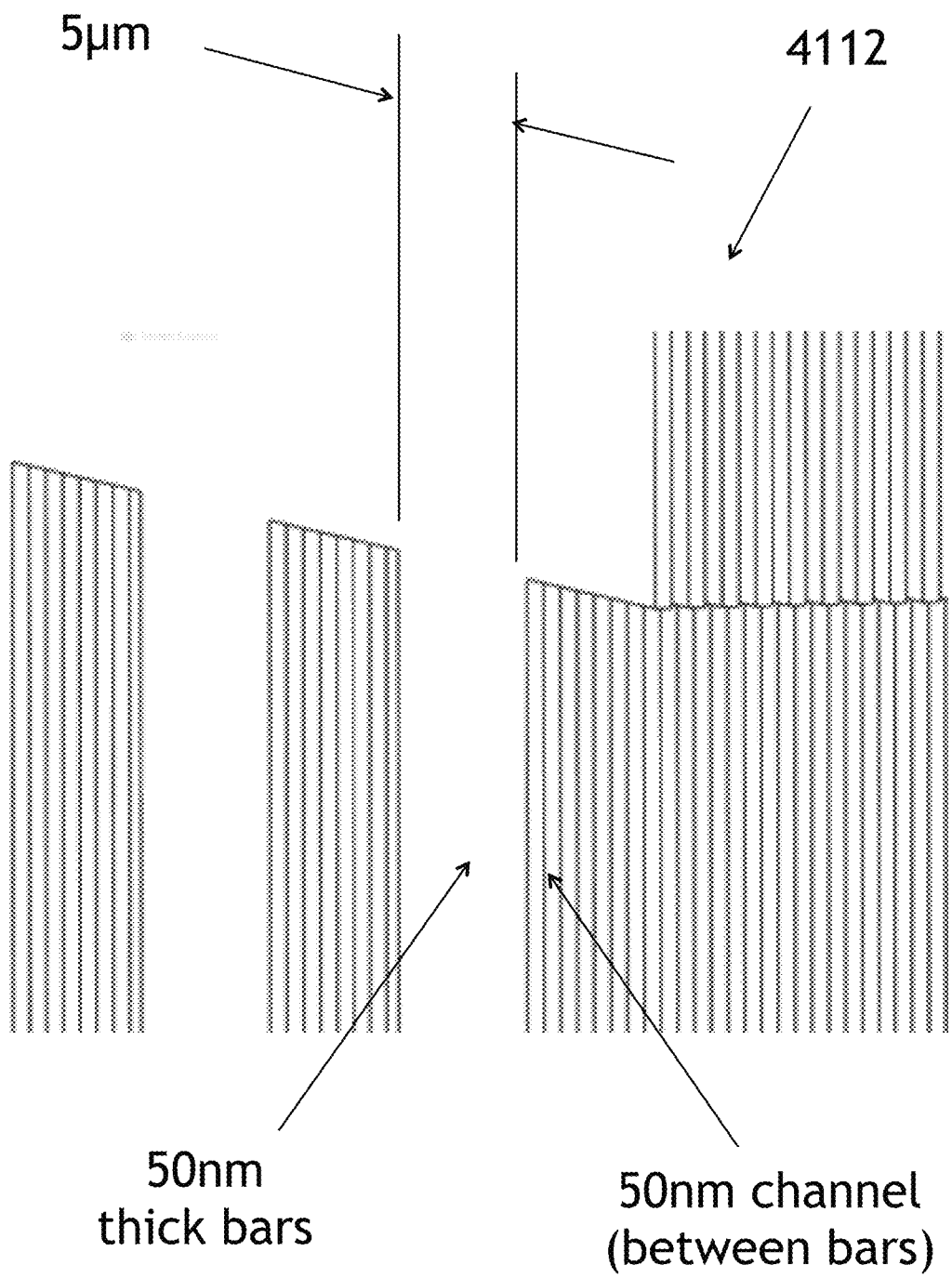
FIG. 45 is a perspective view of the microstructure filter showing channels and bars.

FIG. 45 is a close up view of a layered section of the microstructure filter 4112 illustrating channels, such as channels 4130 formed into layered sections (also referred to as "bars") through etching.

Figure 46:
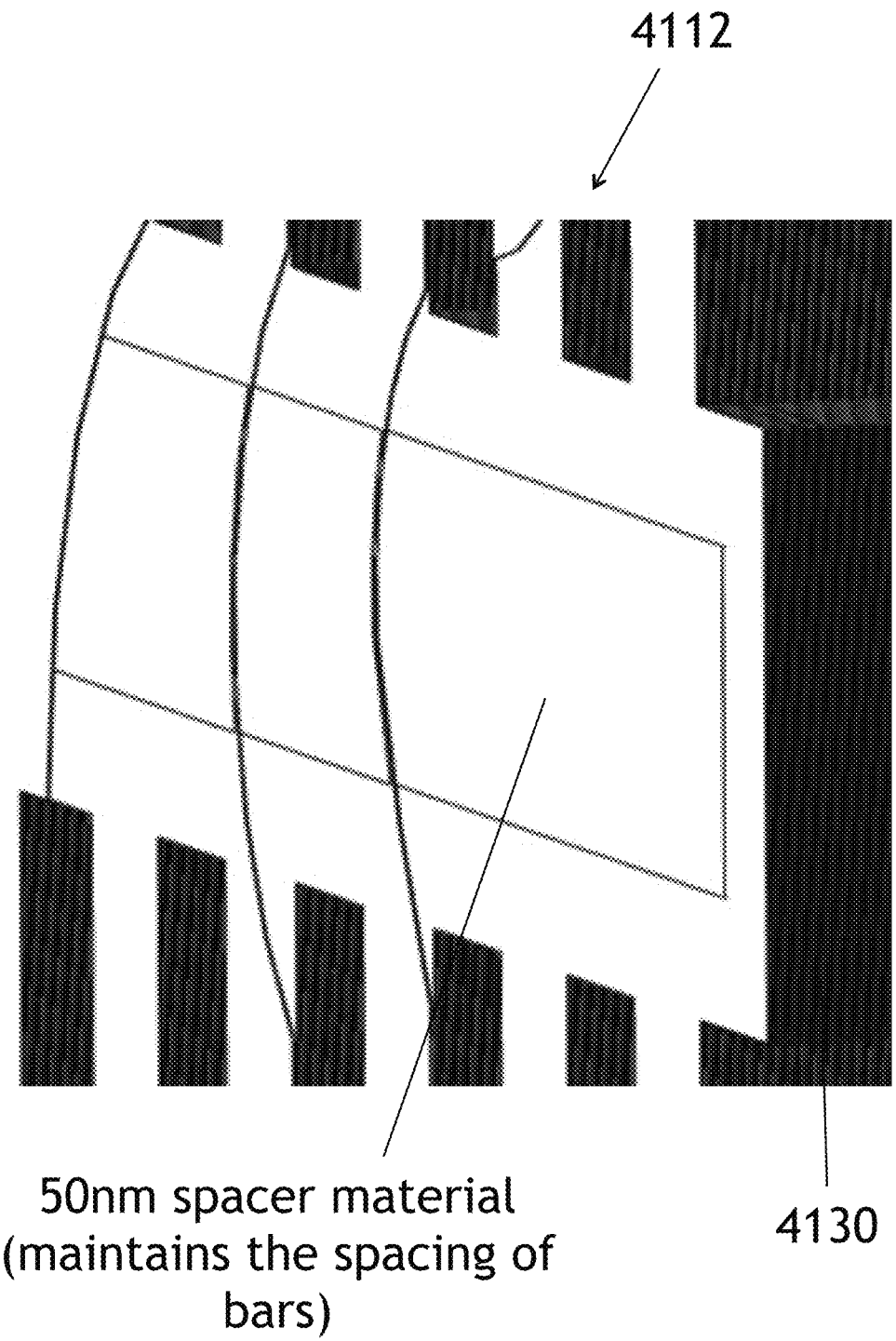
FIG. 46 is a perspective view of the microstructure filter showing spacer (structural) material.

In some embodiments, a spacer material 4132 is utilized to maintain spacing of the layered sections as illustrated in FIG. 46.

Figure 47:
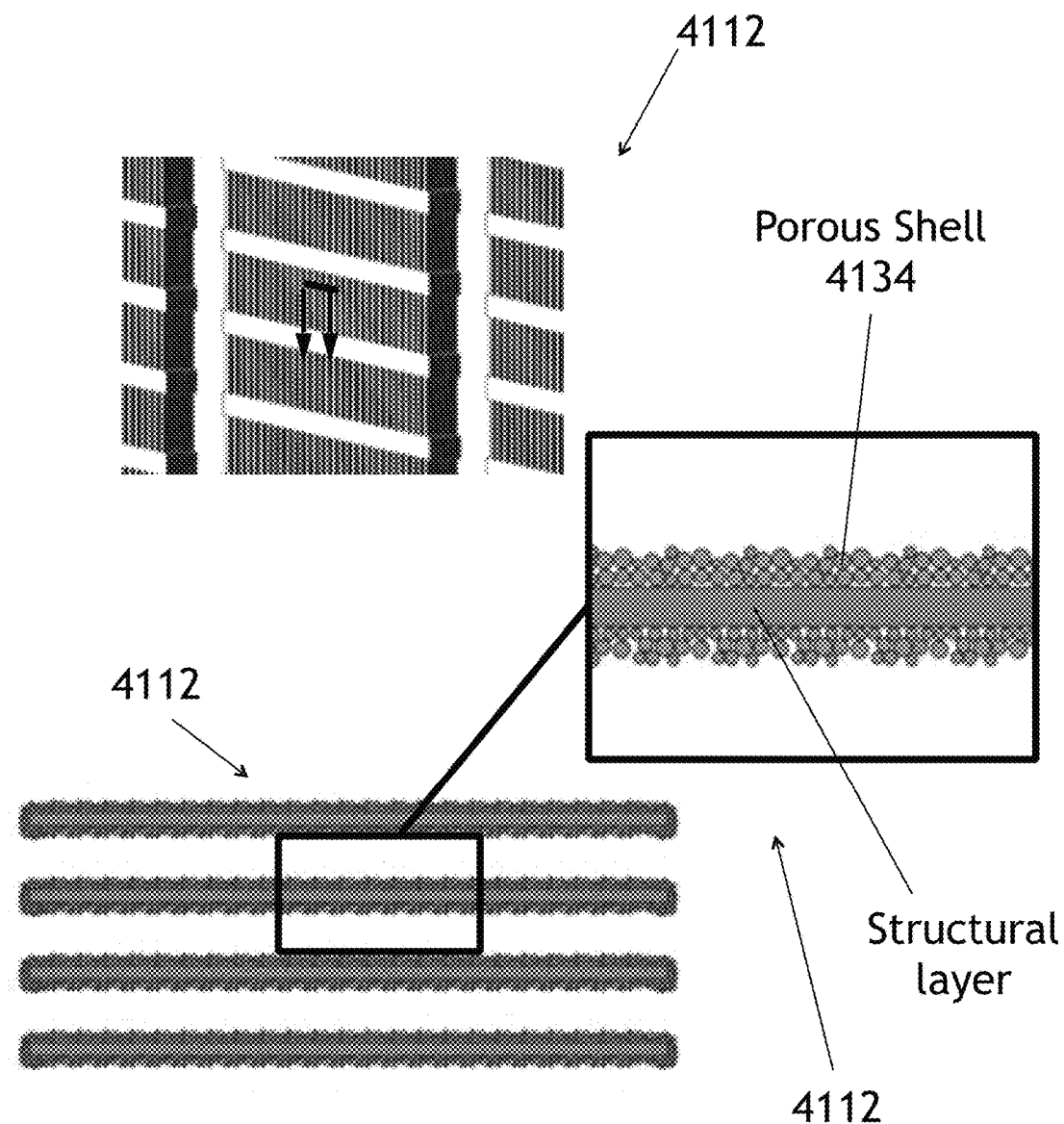
FIG. 47 illustrates a cutaway section showing filter features with nanoscale coatings.

FIG. 47 illustrates that the individual structural layers of the layered sections (e.g., 4120A-C) can be coated or manufactured with three dimensional coatings 4134. This again increases the surface area of the layered sections, which improves the filtering capabilities of the microstructure filter 4112. Again, one of ordinary skill in the art could use various coating processes to coat the individual structural layers to create artifacts that result in the creation of three dimensional aspects on the structural layers.

Figure 48:
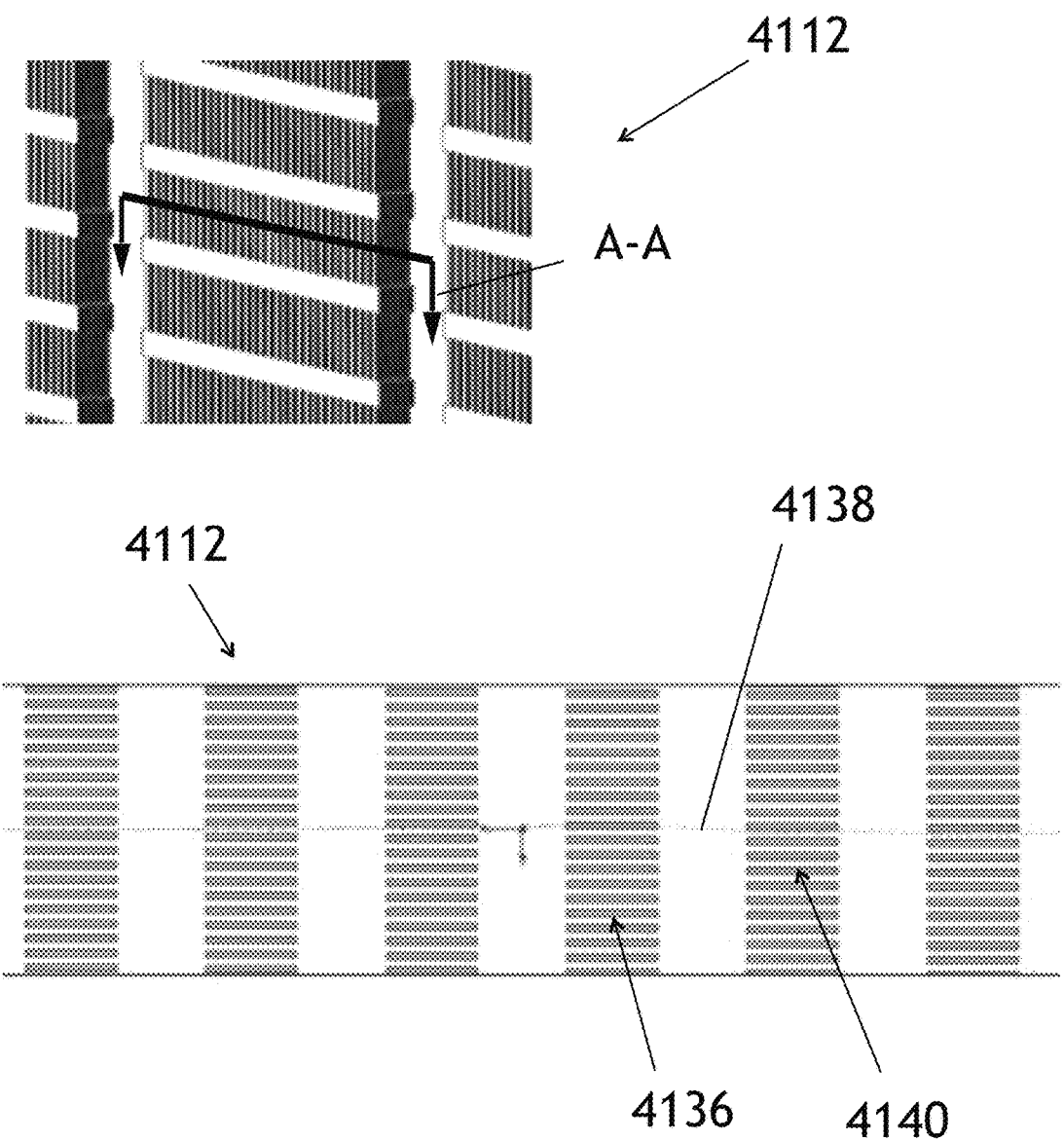
FIG. 48 illustrates a top down view of layers of the microstructure filter, showing offsetting of layers.

FIG. 48 is a top down view of the microstructure filter 4112 taken across section view A-A. The layered sections are shown as comprising individual cross channel filter features, such as filter features 4136. Again, filter features 4136 of adjacent layered sections can be offset from one another, which allow the fluid to be flowing close to a surface of a structural layer ensuring that the fluid contacts at least one surface.

In some embodiments, the features of the structural layers can be staggered or offset from one another by approximately one nano-meter or any other distance per design requirements. Offsetting of structural layers causes the fluid 4138 to divert downwardly from filter features 4136 to adjacent filter features 4140. Also, offsetting of the layers and resulting features reduces and/or eliminates the effect of accelerating of the fluid as would commonly occur through a straight-line channel or path. The same effect is produced in device of FIG. 21.

Figure 49:
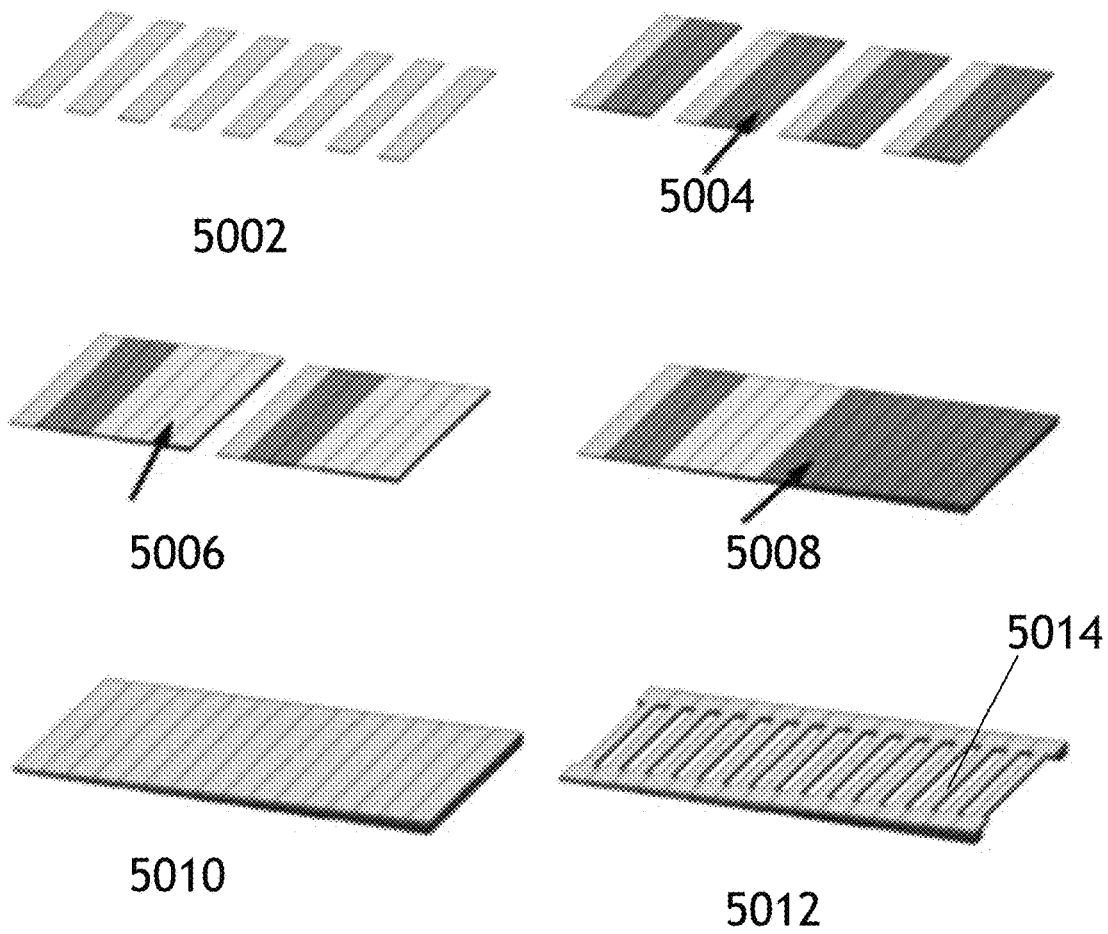
FIG. 49 illustrates a process of photoresist, deposition, and etching to create a microstructure filter.

FIG. 49 illustrates the creation of a microstructure filter which begins with a step 5002 of photolithography and deposition of a sacrificial layer. Sections of sacrificial material are spaced apart from one another. Step 5004 includes the photolithography and deposition of another sacrificial layer that is offset from the sacrificial layer in step 5002. Pairs of sections of the second sacrificial layer are placed on the first sections of the sacrificial layer such that half of the sections of the first layer are visible.

In step 5006 photolithography and deposition of a third sacrificial layer, which is illustrated as being offset from the second sacrificial layer in step 5004. Triplet sections of sacrificial layers overlap the sections of the second and first sacrificial layers.

In step 5008 photolithography and deposition of a fourth sacrificial layer is illustrated. The fourth layer is deposited on the third layer in continuous sections, covering approximately half of the microstructure filter. Next, in step 5010 structural layers are deposited over the sacrificial layers so as to create a covering. The device is then etched in step 5112 to create openings, such as opening 5114.

In sum, with a series of photolithography, deposition, and etch processes, staggered bars can be created. With four "digital" layers 16 steps can be created and the layers can be staggered incrementally at a distance of one nanometer or less.

Figure 50:
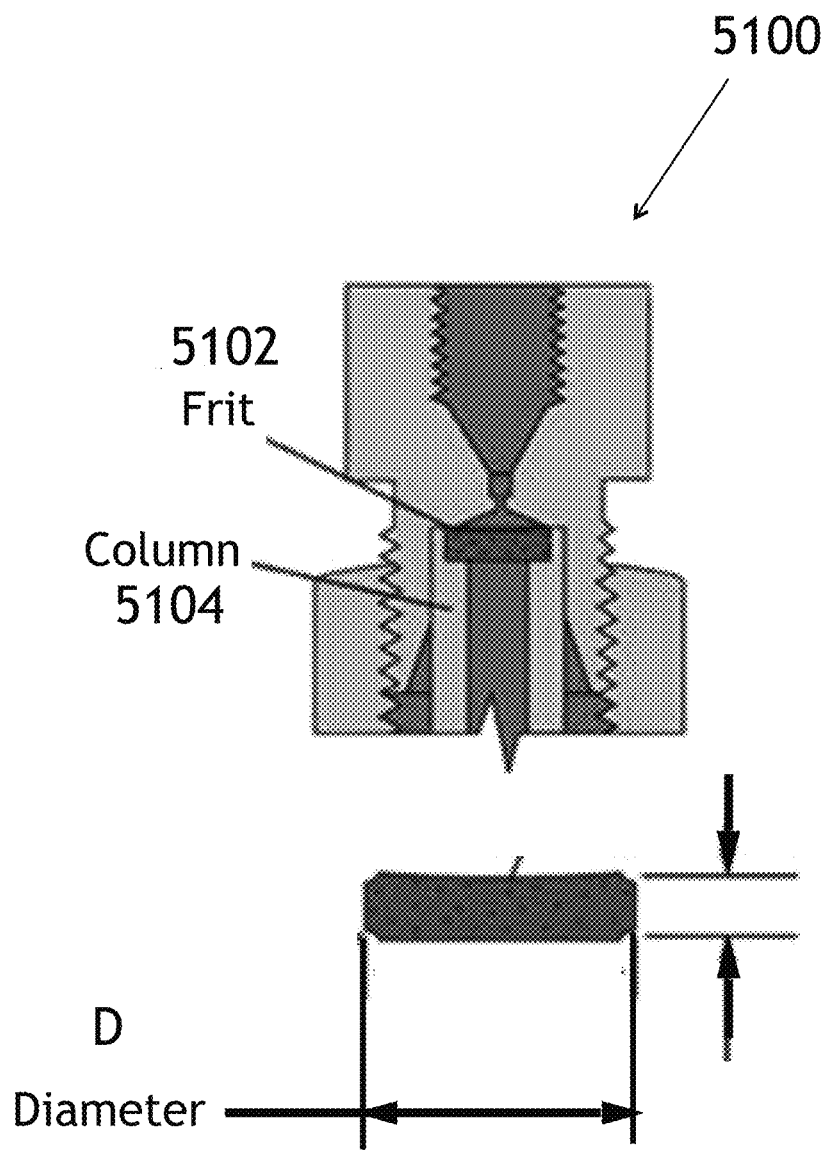
FIG. 50 illustrates a frit in combination with a chromatograph connector.

FIG. 50 illustrates an exemplary filter device connector 5100 that comprises a frit 5102. The frit 5102 is placed into the body of the connector in a path of fluid communication 5104. The frit 5102 can retain particles as well as ensure that longitudinal dispersion of these particles through the filter device is also reduced. To be sure, the filter device connector 5100 can be utilized as the fitting 4104 of FIG. 40.

The frit 5102 comprises a diameter D and a thickness as illustrated.

Figure 51:
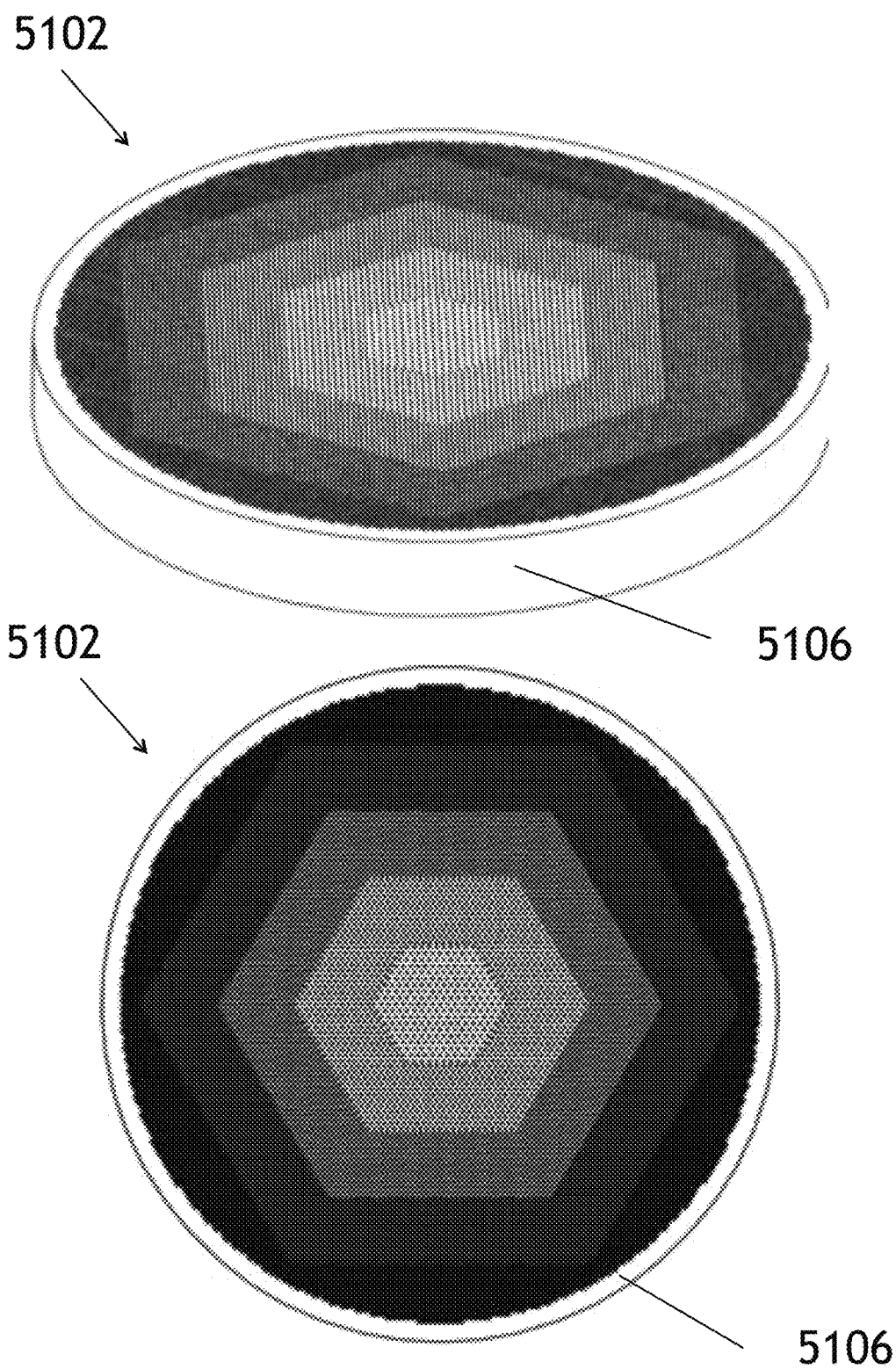
FIGS. 51 and 52 collectively illustrate perspective views of the frit, showing passages.
Figure 52:
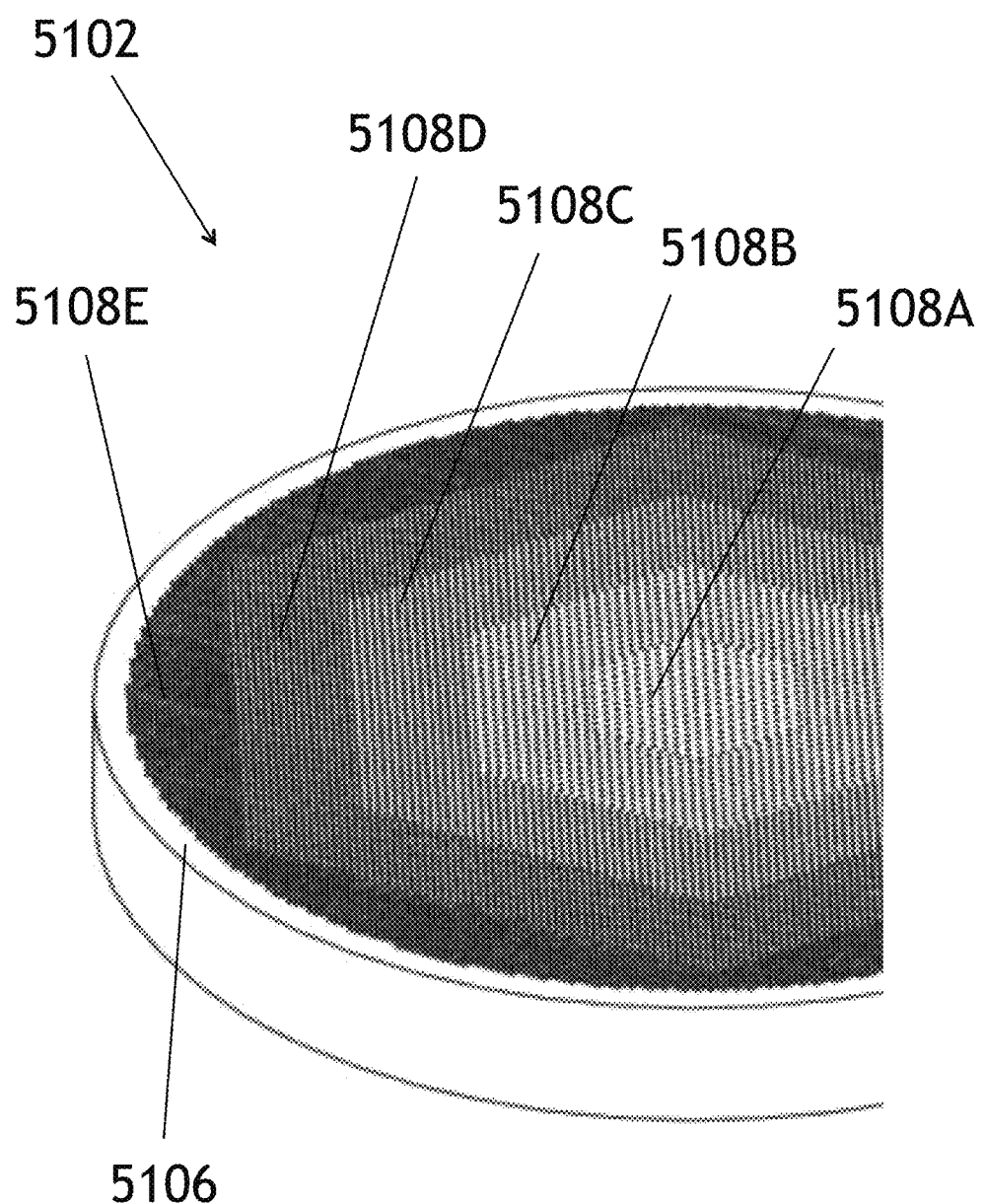

FIGS. 51 and 52 collectively illustrate an example frit 5102 that comprises an outer peripheral sidewall 5106 that encircles a plurality of sections of passages. For example, the frit 5102 can include sections 5108A-E, which are each disposed in ringed configurations. In some embodiments the sections are arranged into hexagonal shapes of passages, although other shapes are likewise contemplated for use.

In some embodiments, each section moving progressively outward will be sized to capture a different size of particle. For example, section 5108A has passages that are the smallest in diameter, while section 5108E has passages that are largest in diameter. Sections in between 5108A and 5108E have progressively larger passages than the section which they encompass. In some embodiments, each section can have a unique size of passages and these sections need not be arranged in a linear manner with respect to passage size.

In some embodiments, not only the diameter of the passages can be varied but also the spacing of the passages. The density of the passages can be tailored to design requirements for operation of the device.

FIGS. 53-65 collectively illustrate further examples of microstructure filters that can be utilized in the devices of the present disclosure. In general, these microstructure filters can comprise disks with microstructures (e.g., filter features) that filter either particles or solutes from fluids. A top surface of the disk would typically be mated to a flat surface to enclose the flow channels on the micro structured disk. In some embodiments, layers of disks can be stacked on top of one another. The disks can be configured in parallel or in series configurations.

As with other microstructure filters, these disks can be coated with different materials to filter different solutes in the fluid. These coatings can include nanoscale structures. Disks with different coatings can be configured in either in series or parallel configurations as well. In some embodiments, the structures can be coated with copper, zinc, carbon, resins and SiO2 are some materials, although many other coatings could be used.

Figure 53:
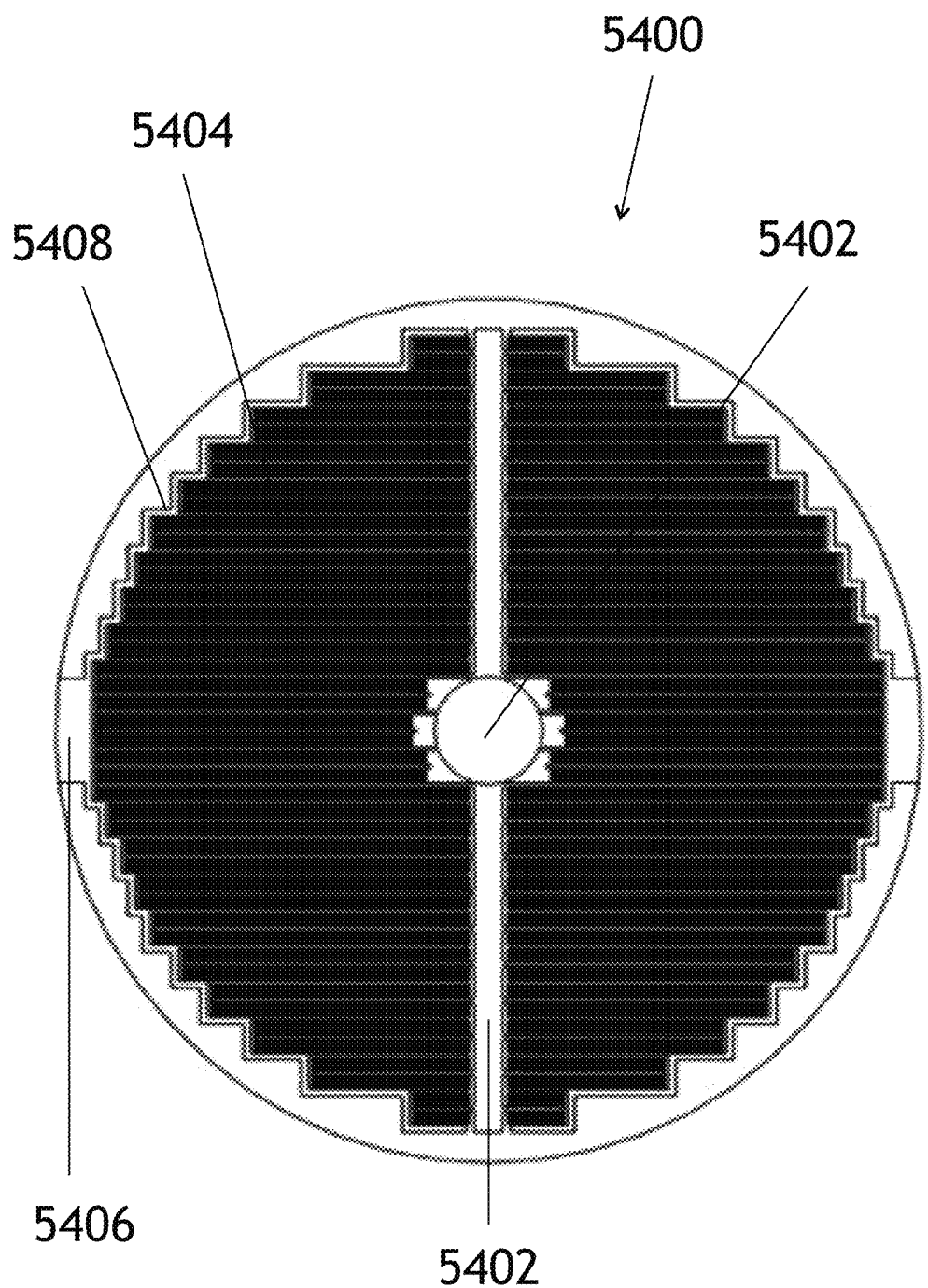
FIGS. 53 and 54 illustrate a front elevational view of an example disk shaped microstructure filter device.

FIG. 53 illustrates a microstructure filter 5400 in disk shape. The filter 5400 comprises a plurality of inlet channels, such as inlet channels 5402 that deliver fluid to a plurality of horizontal channels, such as horizontal channels 5404. The filter 5400 also comprises outlet channels 5406 that collect fluid from the horizontal channels. To be sure the inlet and outlet channels can be switched relative to their configurations such that the outlet channels become inlet channels and vice versa.

Figure 54:
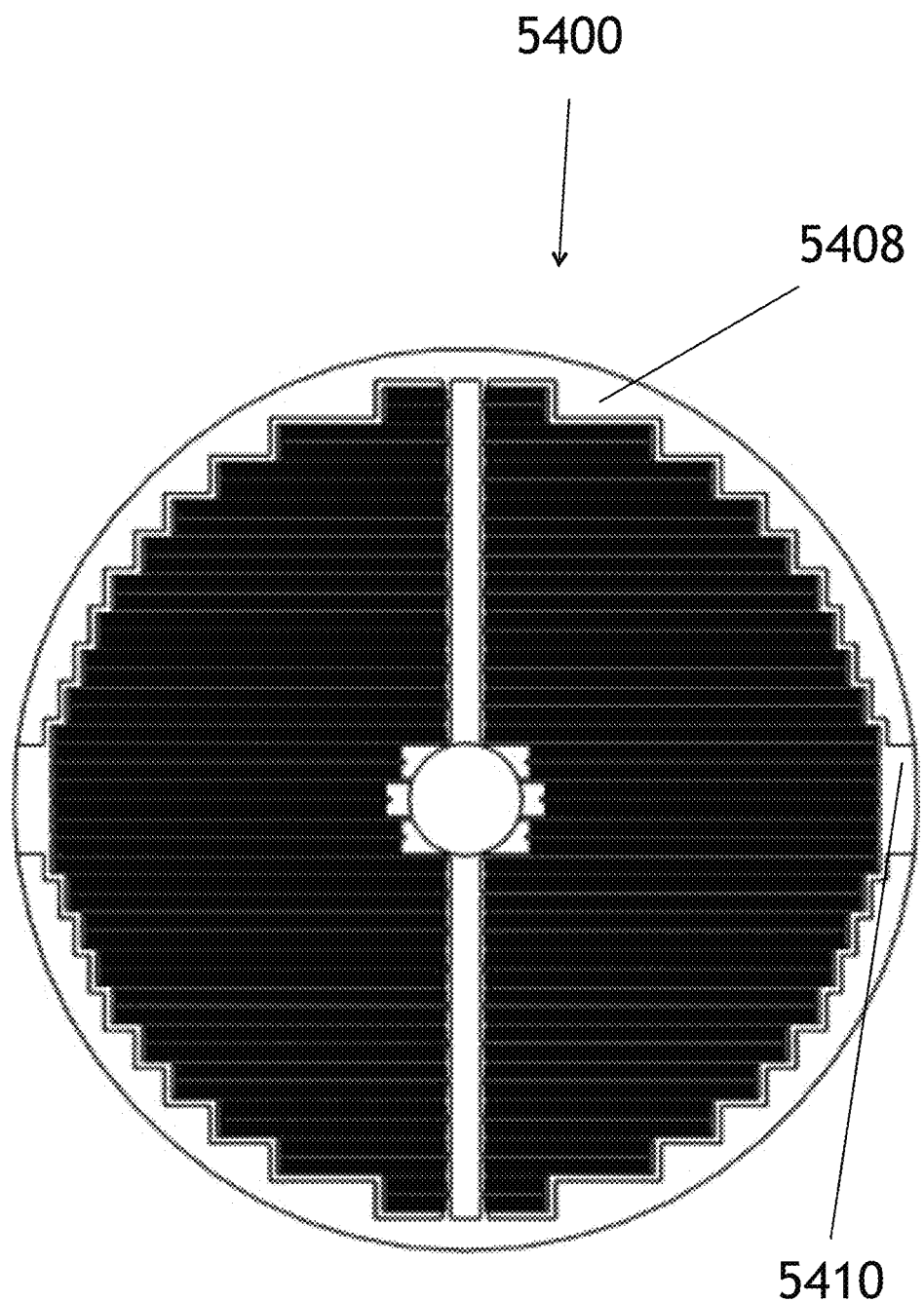
Figure 55:
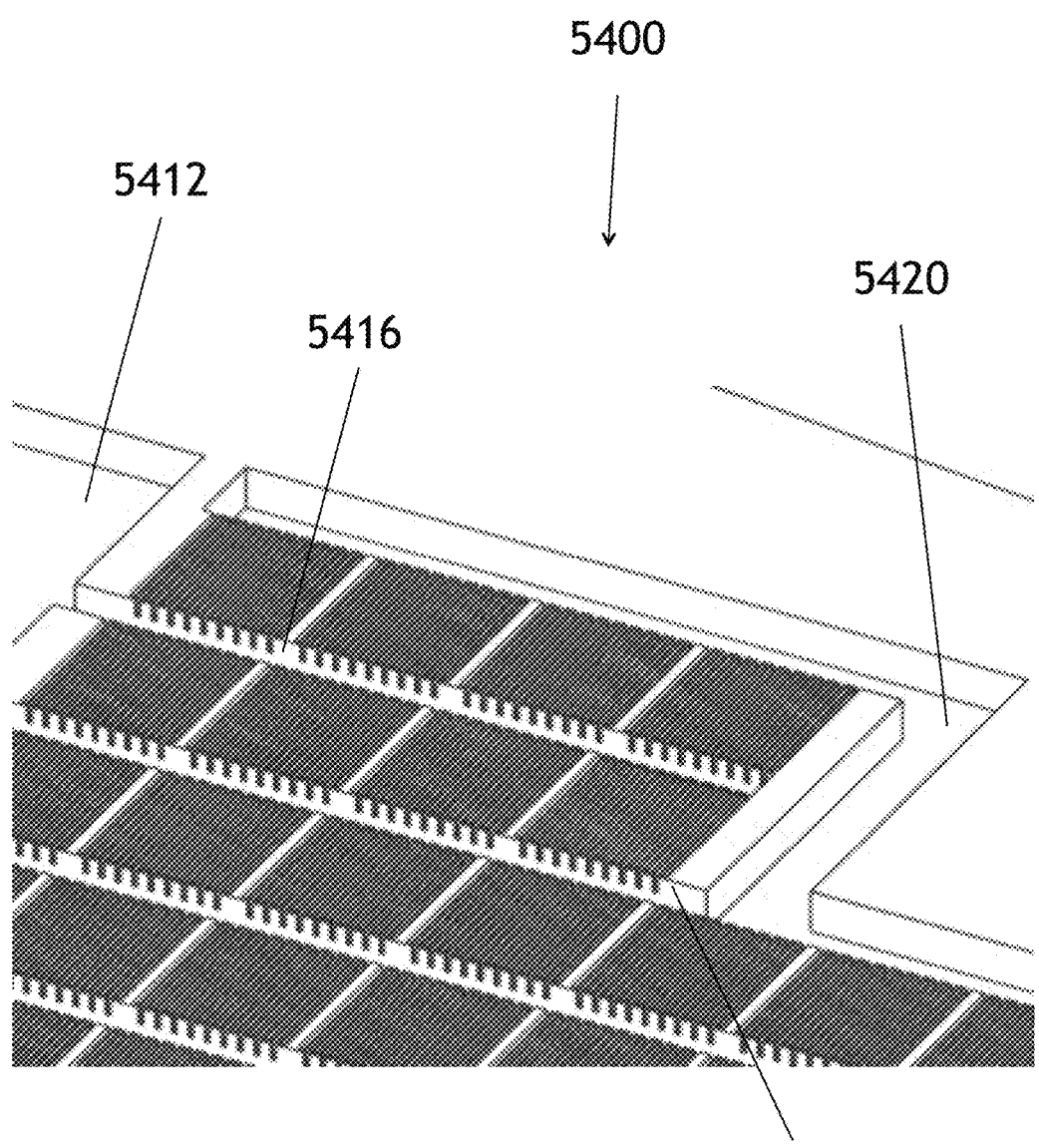
FIGS. 55-59 illustrate close up views of a microstructure filter of the microstructure filter device of FIGS. 53-54.

FIG. 54 illustrates two detail sections 5408 and 5410 that will be described in greater detail herein. In FIGS. 55-59 illustrate filter features of the detail section 5408. For example, in FIG. 55, both large and small flow channels are illustrated. An inlet channel 5412 is illustrated, which feeds fluid to inlet horizontal channels 5416 and outlet horizontal channels 5418. An outlet channel 5420 collects filtered fluid from the inlet horizontal channels 5416 and outlet horizontal channels 5418.

Figure 56:
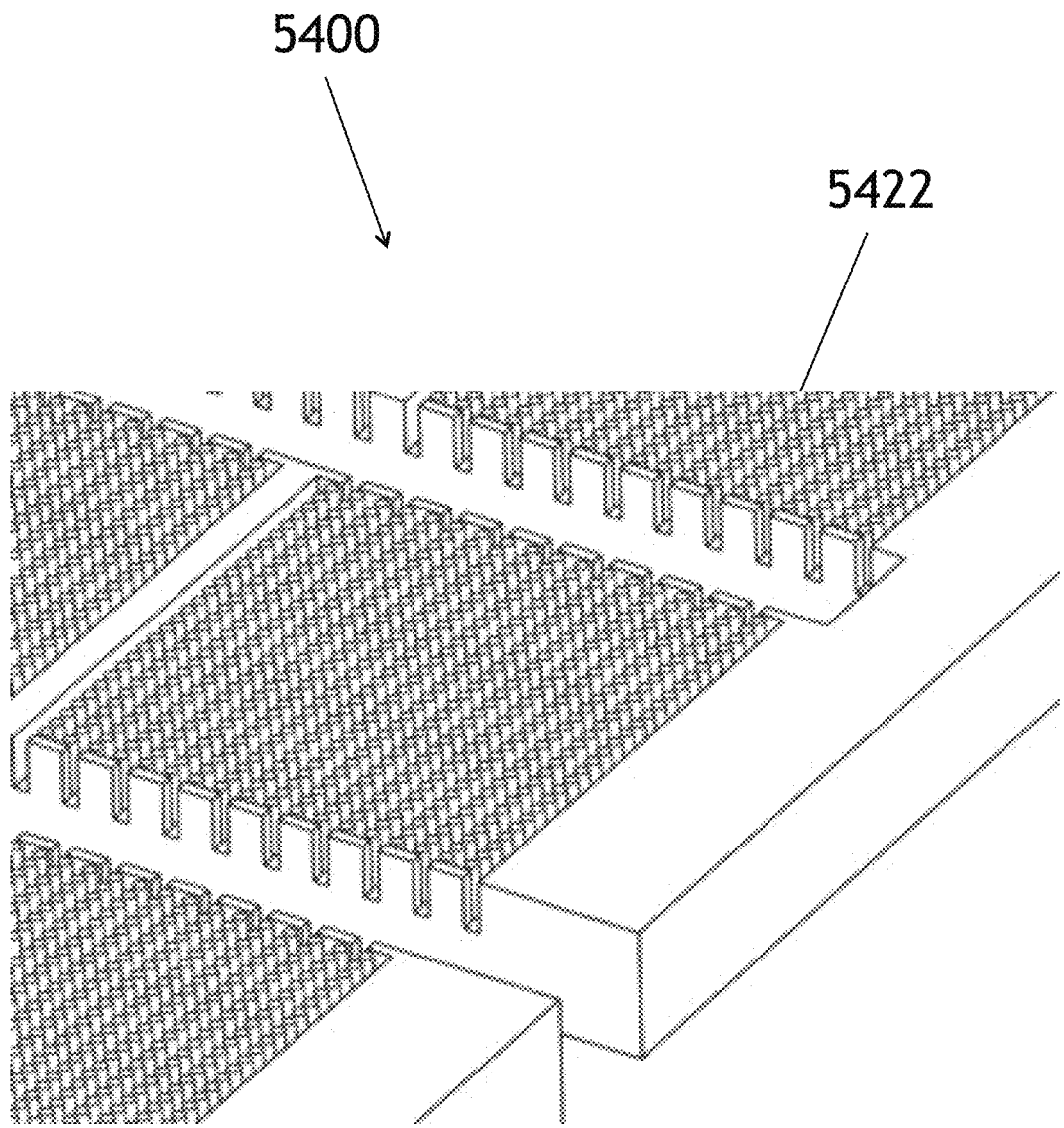

FIG. 56 illustrates horizontal channels with post filter features 5422. Other filter features such as slits, notches, and grooves of varying size and shape can be utilized as well.

Figure 57:
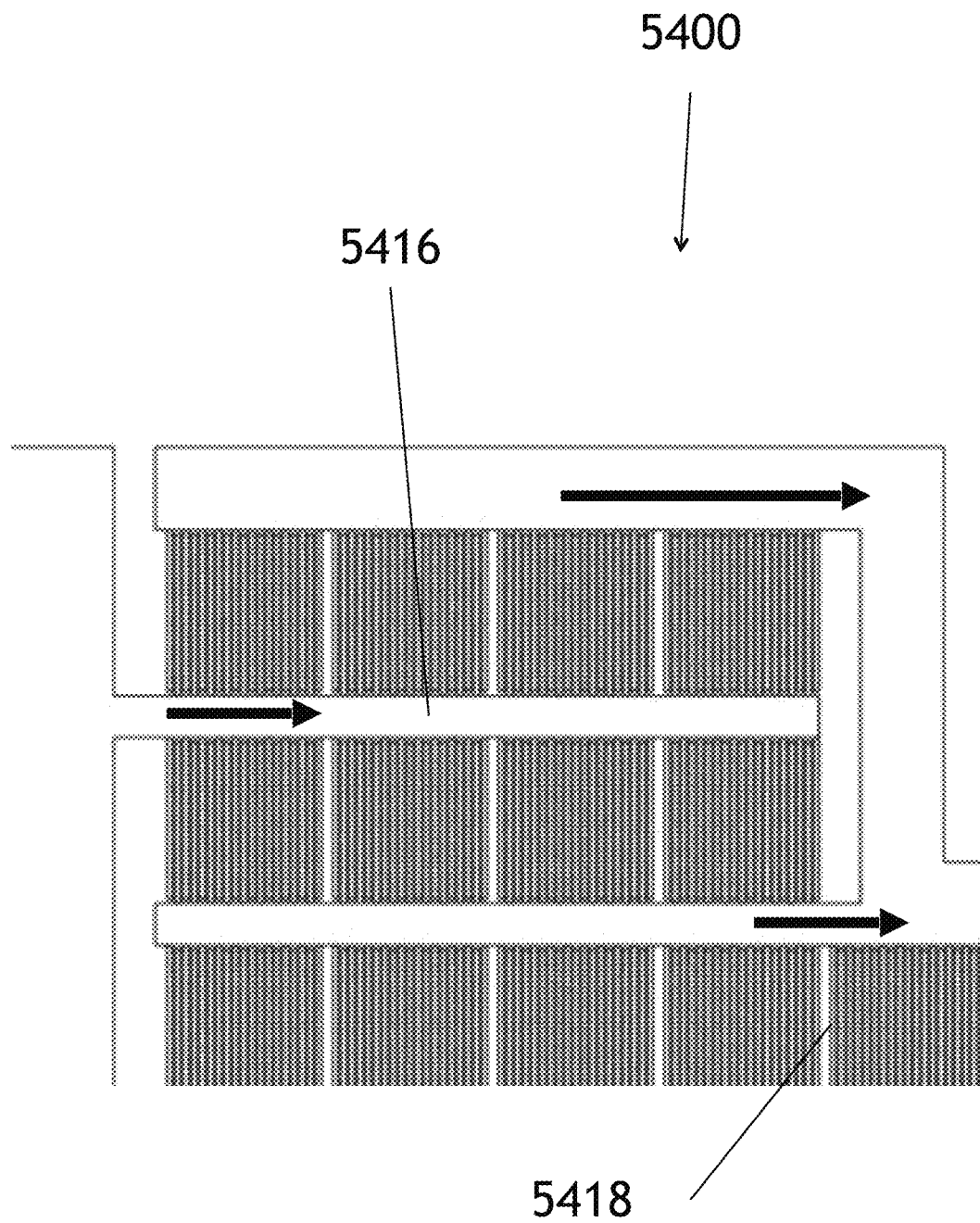

FIG. 57 illustrates a top down view of the inlet horizontal channels 5416 and outlet horizontal channels 5418.

Figure 58:
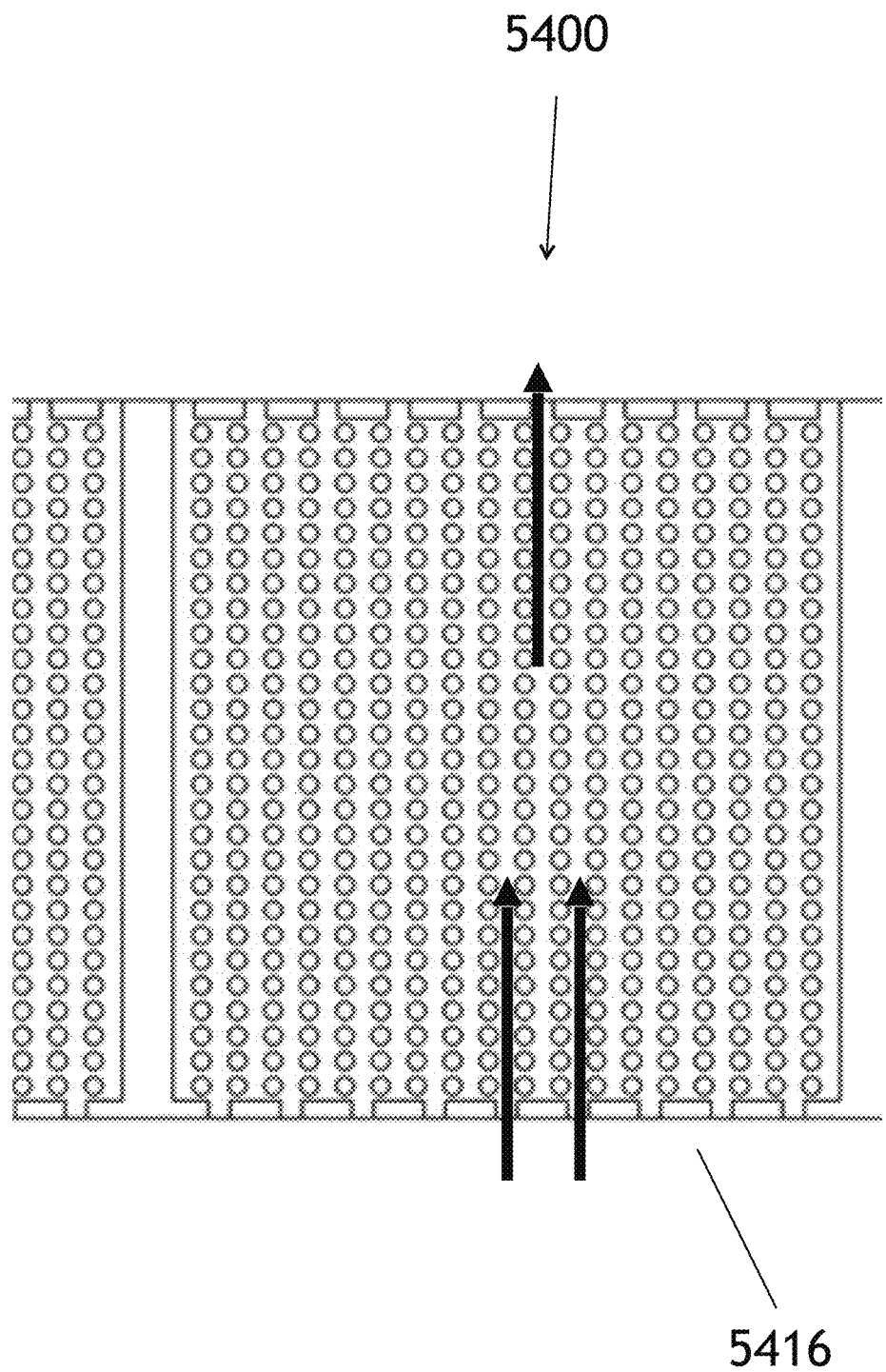
Figure 59:
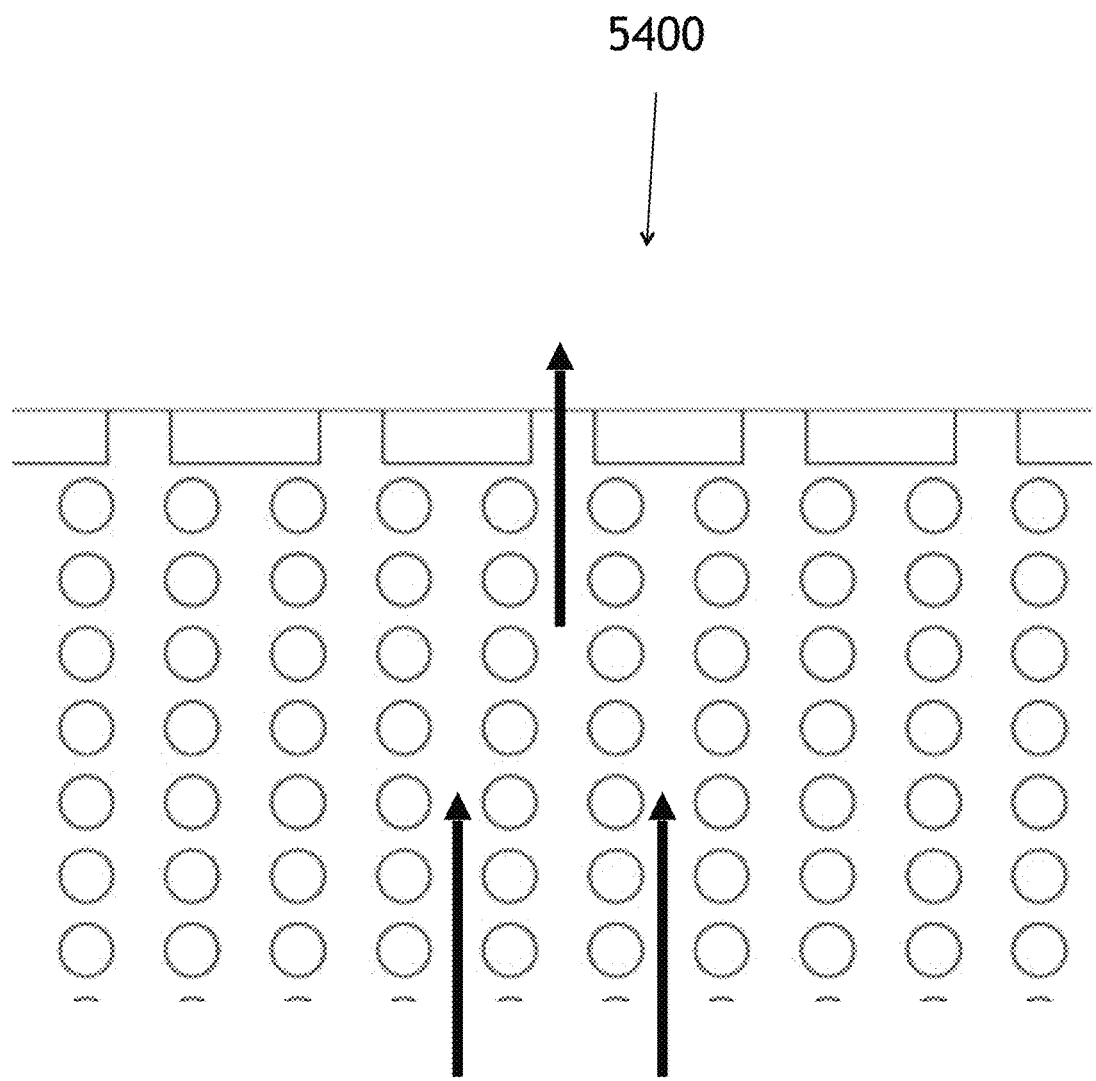

FIG. 58 illustrates a top down view of the inlet horizontal channels 5416 and outlet horizontal channels 5418 with post filter features, and FIG. 59 is a close up view of a section of the view of FIG. 58.

Figure 60:
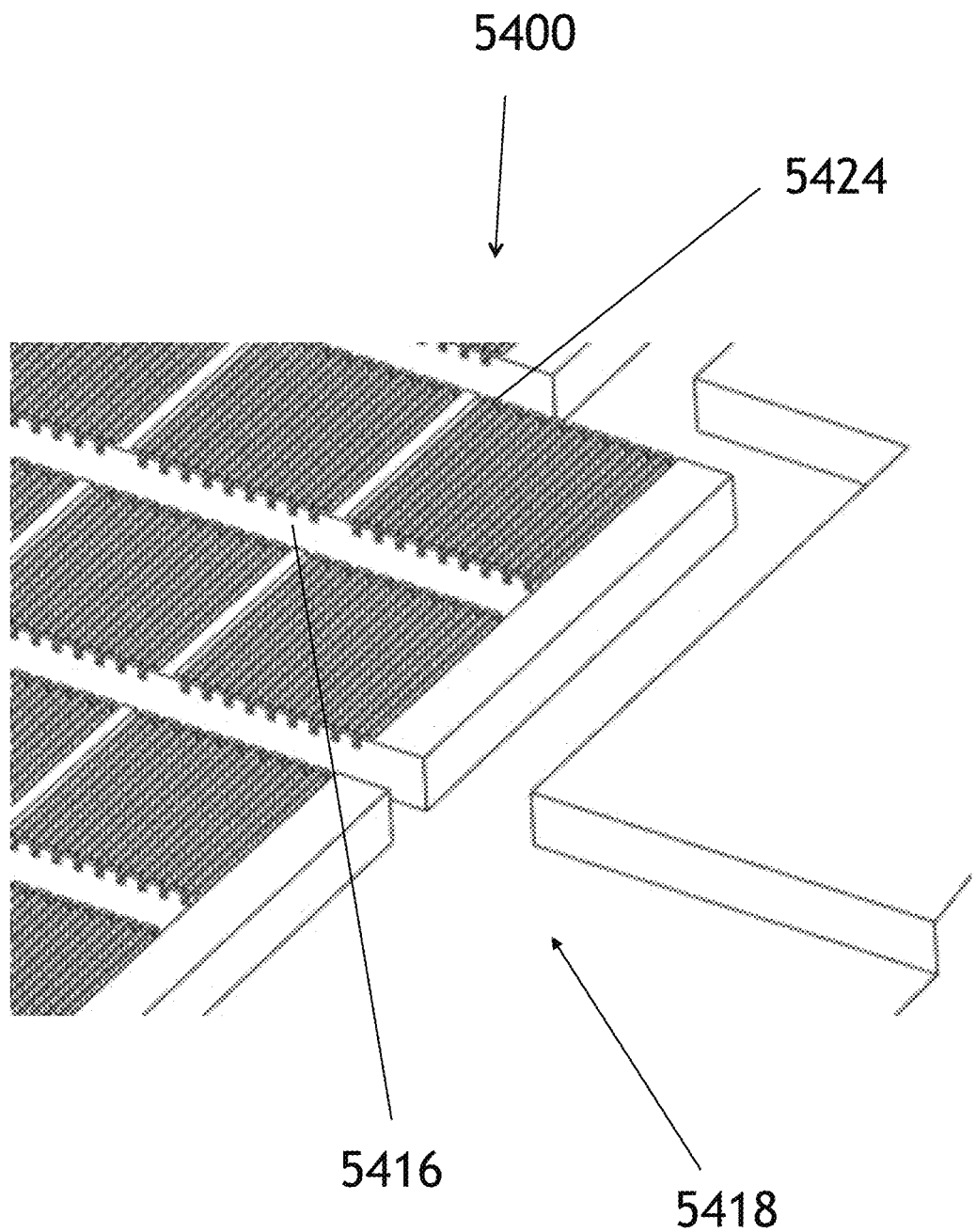
FIG. 60 illustrates another detail section of the microstructure filter of the microstructure filter device.

FIG. 60 illustrates detail section 5410 in more detail. The detail section includes a vertical outlet channel 5424, horizontal inlet channels 5416, and an outlet port 5418. In some embodiments, the vertical outlet channel 5424, horizontal inlet channels 5416, and support layers are coplanar with one another.

Figure 61:
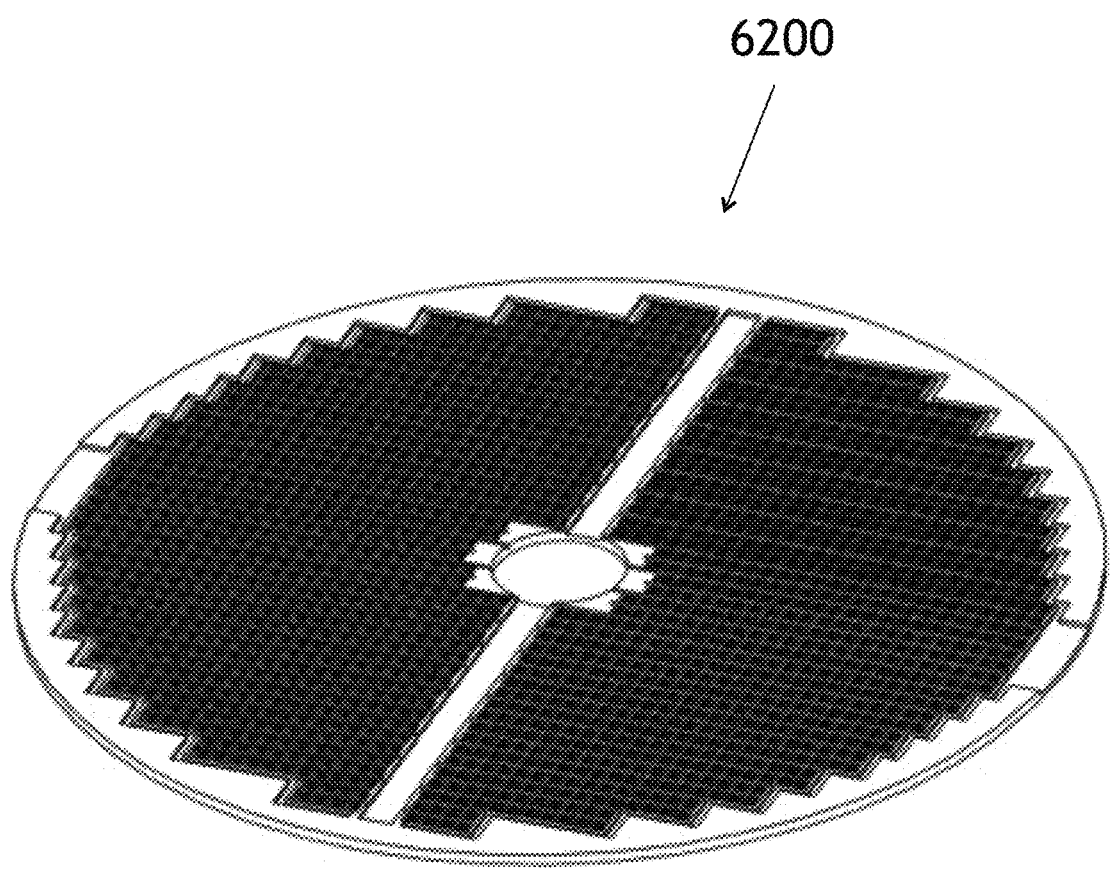
FIG. 61 illustrates a front elevational view of an example disk shaped microstructure filter device with a layered configuration.
Figure 62:
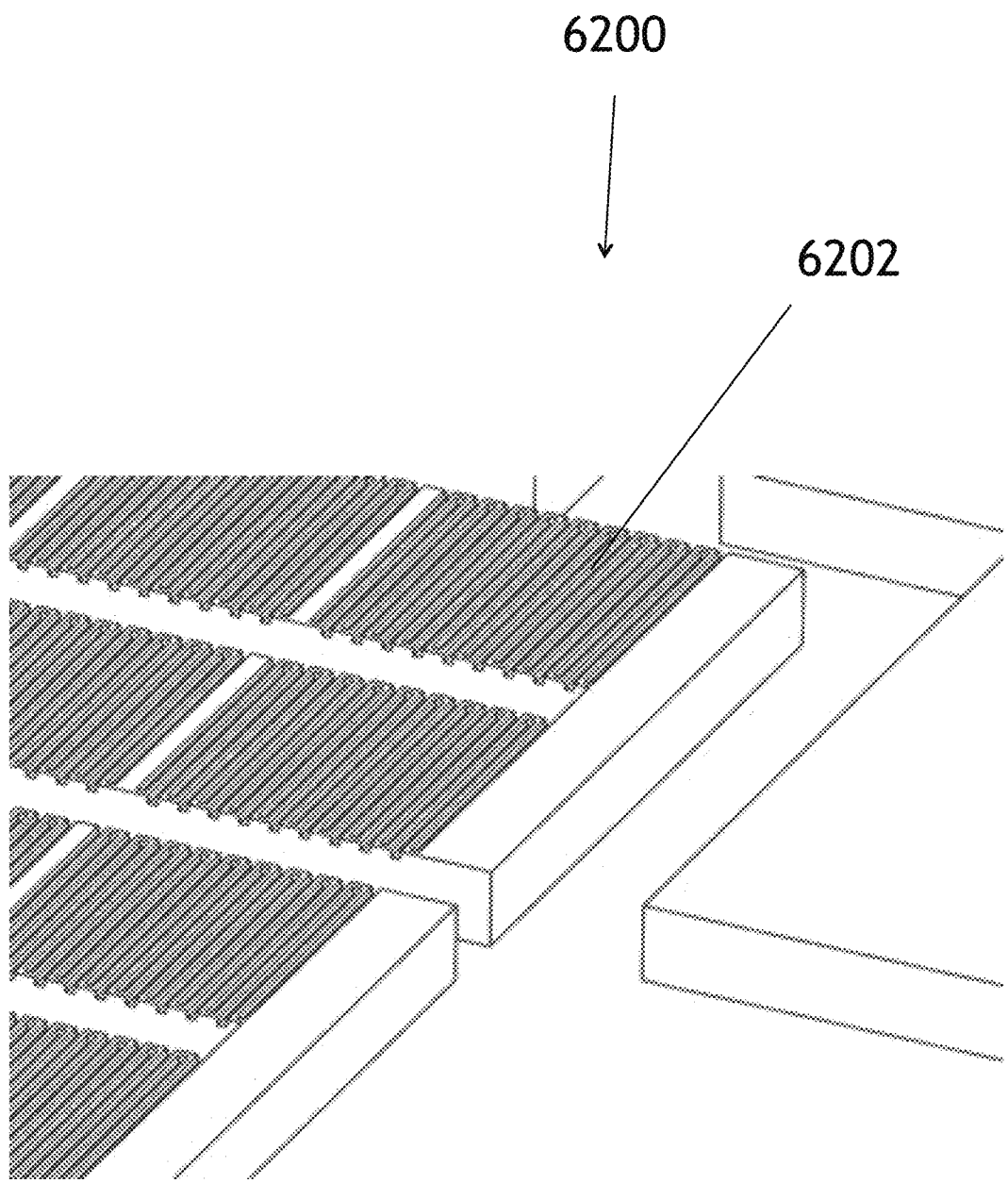
FIG. 62 is a close up perspective view of the filter features of the microstructure filter of the microstructure filter device.
Figure 64:
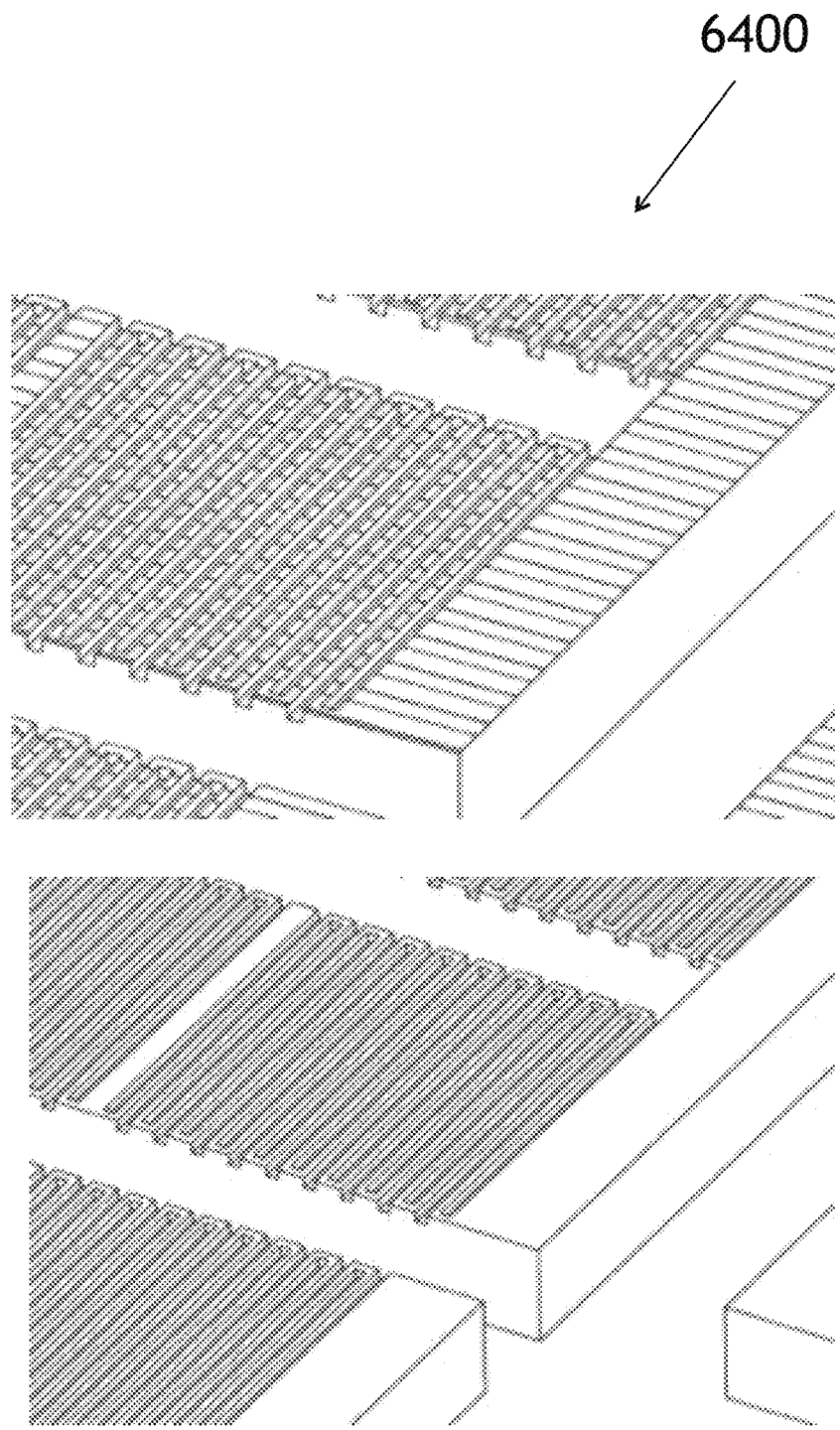

FIG. 61 illustrates another microstructure filter 6200 in disk shape with a layered design. A more detailed view of filter features 6202 of the filter 6200 is illustrated in FIG. 62. The filter features comprise sidewalls instead of posts. In FIG. 64 a more detailed view of the sidewalls is provided. In some embodiments, the walls can be 0.1 nanometers tall and 0.05 nanometers wide.

Figure 63:
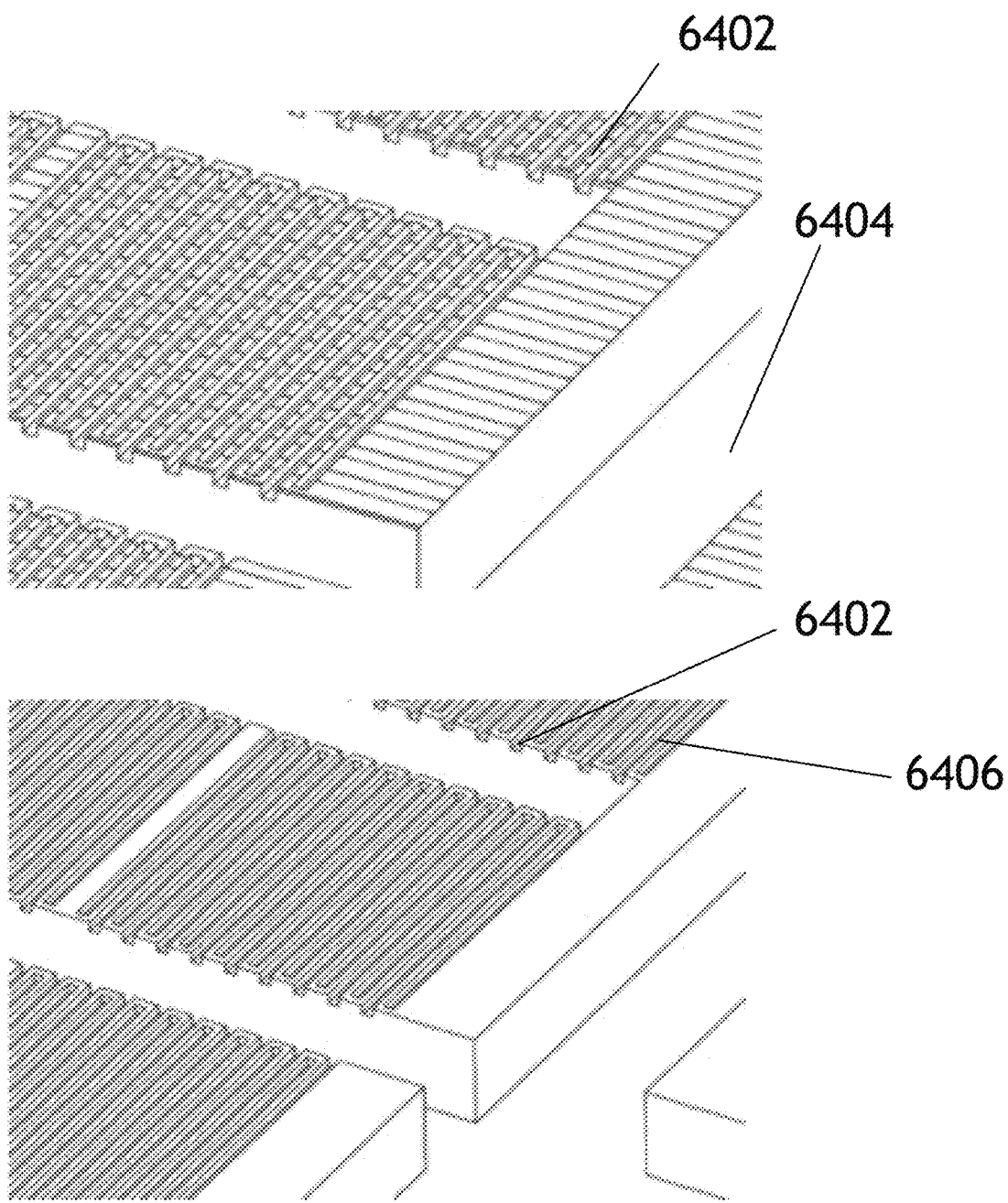
FIGS. 63-65 collective illustrate a process for creating thin bars which form the filter features of the microstructure filter.
Figure 65:
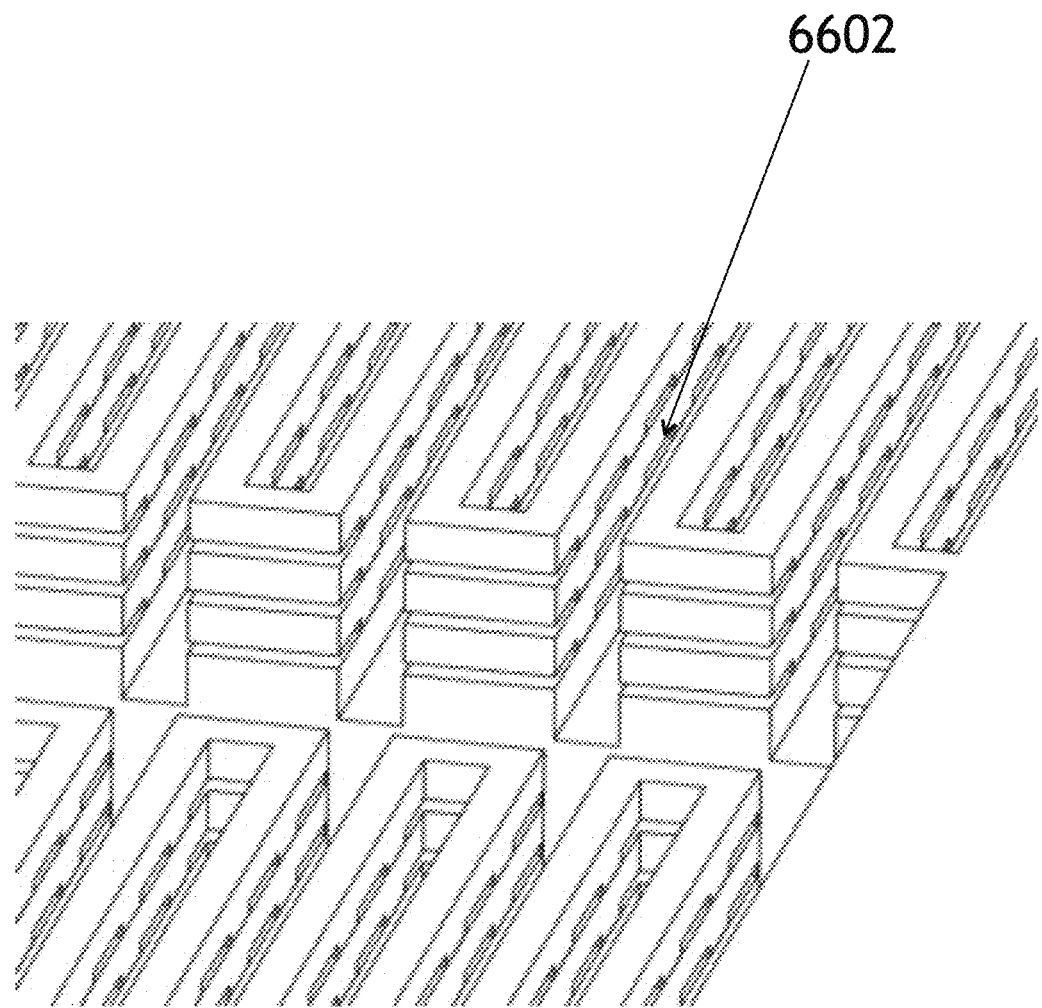

FIGS. 63-65 illustrate a layer deposition process for creating the sidewalls. In FIG. 63, thin bars 6402 are printed or coated onto a support surface 6404. The material used in this deposition process can be a sacrificial material. A second layer 6406 is deposited onto the bars 6402 and can be created from a structural material.

Additional bars of structural and/or sacrificial material can be applied to the bars 6402 as illustrated FIG. 64.

A view of a section of a completed filter disk is illustrated in FIG. 65. To be sure, when sacrificial layers are removed filter orifices 6602 (filter features) are created. Again, the surface of these bars and surfaces can be coated as needed.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A filter device, comprising:
a microstructure filter comprising a plurality of layers of structural material which are spaced apart to create inlet channels and outlet channels, wherein adjacent ones of the inlet channels and the outlet channels are spaced apart from one another by cross channels that filter a fluid from the inlet channels to the outlet channels, the cross channels comprising filter features formed by removing a portion of the plurality of layers of the structural material; and
a housing configured to receive the microstructure filter, the housing being configured to connect to a chromatograph device to test the fluid, wherein the housing comprises an inlet notch on a first end and an outlet notch on a second end, wherein the microstructure filter is disposed between the inlet notch and the outlet notch, the inlet notch being associated with an upper fluid pathway, the upper fluid pathway having a widest point proximate the inlet notch and tapering to a terminal end proximate the second end of the housing above the microstructure filter, the outlet notch being associated with a lower fluid pathway, the lower fluid pathway having a widest point proximate the outlet notch and tapering to a terminal end proximate the first end of the housing below the microstructure filter, the plurality of layers of structural material of the microstructure filter filling a space between the upper fluid pathway and the lower fluid pathway, wherein all of the fluid passing into the upper fluid pathway enters the microstructure filter and exits to the lower fluid pathway and out of the outlet notch.

2. The filter device according to claim 1, wherein the filter features comprise openings that are sized to capture particles present in the fluid.

3. The filter device according to claim 1, wherein the microstructure filter comprises a plurality of spacer areas that provide structural support between adjacent ones of the plurality of layers of structural material, wherein the filter features are disposed between adjacent ones of the plurality of spacer areas.

4. The filter device according to claim 3, wherein adjacent ones of the plurality of spacer areas are offset from one another to stagger the filter features of adjacent layers of the plurality of layers.

5. The filter device according to claim 1, wherein the filter device is nested into the housing such that fluid enters a first end of the microstructure filter and exits a second end of the microstructure filter.

6. The filter device according to claim 1, wherein the microstructure filter comprises an etched inlet section and an etched outlet section.

7. The filter device according to claim 1, wherein the housing is a tubular case that comprises an inner shell that includes a notch for receiving the microstructure filter.

8. The filter device according to claim 1, wherein at least a portion of the filter features are provided with a nanoscale surface treatment to increase surface area of the filter features and thus an attractive force exerted by the filter features onto particles in the fluid.

9. The filter device according to claim 1, wherein the housing comprises a first connector that delivers fluid to the microstructure filter, wherein the first connector is configured to filter the fluid prior to entry into the microstructure filter.

10. The filter device according to claim 9, wherein the first connection is a frit comprising an outer peripheral sidewall that encircles a plurality of sections of passages.

11. The filter device according to claim 10, wherein the plurality of sections of passages are disposed in a ringed configuration and arranged such that passages of sections near a center of the frit have smaller diameter passages than passages of sections near the outer peripheral sidewall.

12. The filter device according to claim 10, wherein the plurality of sections of passages each comprise passages with unique spacing or diameter.

* * * * *